United States Patent
Herzog et al.

(10) Patent No.: US 10,556,932 B2
(45) Date of Patent: *Feb. 11, 2020

(54) COMPOSITIONS AND METHODS FOR SUPPRESSION OF INHIBITOR FORMATION AGAINST COAGULATION FACTORS IN HEMOPHILIA PATIENTS

(71) Applicants: THE TRUSTEES OF THE UNIVERSITY OF PENNSYLVANIA, Philadelphia, PA (US); UNIVERSITY OF FLORIDA RESEARCH FOUNDATION, INC., Gainesville, FL (US)

(72) Inventors: Roland W. Herzog, Gainesville, FL (US); Henry Daniell, Media, PA (US)

(73) Assignees: The Trustees of the University of Pennsylvania, Philadelphia, PA (US); University of Florida Research Foundation, Inc., Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/299,928

(22) Filed: Mar. 12, 2019

(65) Prior Publication Data

US 2019/0194265 A1  Jun. 27, 2019

Related U.S. Application Data

(60) Division of application No. 15/037,045, filed on May 16, 2016, now Pat. No. 10,233,216, which is a continuation-in-part of application No. PCT/US2014/065994, filed on Nov. 17, 2014.

(60) Provisional application No. 61/905,069, filed on Nov. 15, 2013, provisional application No. 61/905,071, filed on Nov. 15, 2013.

(51) Int. Cl.
| | |
|---|---|
| *C07K 14/00* | (2006.01) |
| *C07K 14/28* | (2006.01) |
| *C12N 15/82* | (2006.01) |
| *A61K 38/36* | (2006.01) |
| *A61K 38/37* | (2006.01) |
| *A61K 38/47* | (2006.01) |
| *C07K 14/755* | (2006.01) |
| *A61K 38/45* | (2006.01) |
| *A61K 36/00* | (2006.01) |

(52) U.S. Cl.
CPC .............. *C07K 14/28* (2013.01); *A61K 38/36* (2013.01); *A61K 38/37* (2013.01); *A61K 38/45* (2013.01); *A61K 38/47* (2013.01); *C07K 14/755* (2013.01); *C12N 15/8214* (2013.01); *C12N 15/8257* (2013.01); *C12Y 204/00* (2013.01); *C12Y 302/0102* (2013.01); *C12Y 302/01022* (2013.01); *A61K 36/00* (2013.01); *C07K 2319/00* (2013.01); *Y02A 50/471* (2018.01)

(58) Field of Classification Search
None
See application file for complete search history.

(56) References Cited

U.S. PATENT DOCUMENTS

| | | |
|---|---|---|
| 2011/0179530 A1 | 7/2011 | Daniell |
| 2011/0311513 A1 | 12/2011 | Steed et al. |

FOREIGN PATENT DOCUMENTS

| | | |
|---|---|---|
| WO | 2013/106789 A1 | 1/2013 |

OTHER PUBLICATIONS

Lei, Tie Chi et al., "Induction of tolerance to factor VIII inhibitors by gene therapy with immunodominant A1 and C2 domains presented by B cells as Ig fusion proteins",Blood, 105: 4865-4870 (2005).
Sherman, Alexandra et al., "Suppression of inhibitor formation against FVIII in a murine model of hemophilia A by oral delivery of antigens bioencapsulated in plant cells", Blood, 124(10): 1659-1668 (2014).
Verma, Dheeraj et al., "Oral delivery of bioencapsulated coagulation factor IX prevents inhibitor formation and fatal anaphylaxis in hemophilia B mice", Proceedings of the National Academy of Sciences of the United States of America, 107(15): 7101-7106 (2010).
Wang, Xiaomei et al., "Plant-based oral tolerance to hemophilia therapy employs a complex immune regulatory response including LAP+ CD+ T cells", Blood, 125(15): 2418-2427 (2015).
Extended European Search Report, dated Mar. 27, 2017, issued in corresponding European Patent Application No. 14862042.0.
(Continued)

*Primary Examiner* — Jeanette M Lieb
(74) *Attorney, Agent, or Firm* — Kathleen D. Rigaut; Howson & Howson LLP

(57) ABSTRACT

Protein replacement therapy for patients with hemophilia or other inherited protein deficiencies is often complicated by pathogenic antibody responses, including antibodies that neutralize the therapeutic protein or that predispose to potentially life-threatening anaphylactic reactions by formation of IgE. Using murine and canine hemophilia as a model, we have developed a prophylactic protocol against such responses that is non-invasive and does not include immune suppression or genetic manipulation of the patient's cells. Oral delivery of a coagulation factor expressed in chloroplasts, bioencapsulated in plant cells, effectively blocked formation of inhibitory antibodies in protein replacement therapy. Inhibitor titers were mostly undetectable and up to 100-fold lower in treated subjects when compared to controls. Moreover, this treatment eliminated fatal anaphylactic reactions that occurred after four to six exposures to intravenous coagulation factor protein. Finally, the method can effectively be used to reverse or reduce undesirable pre-existing inhibitor titers.

Figure 1A:
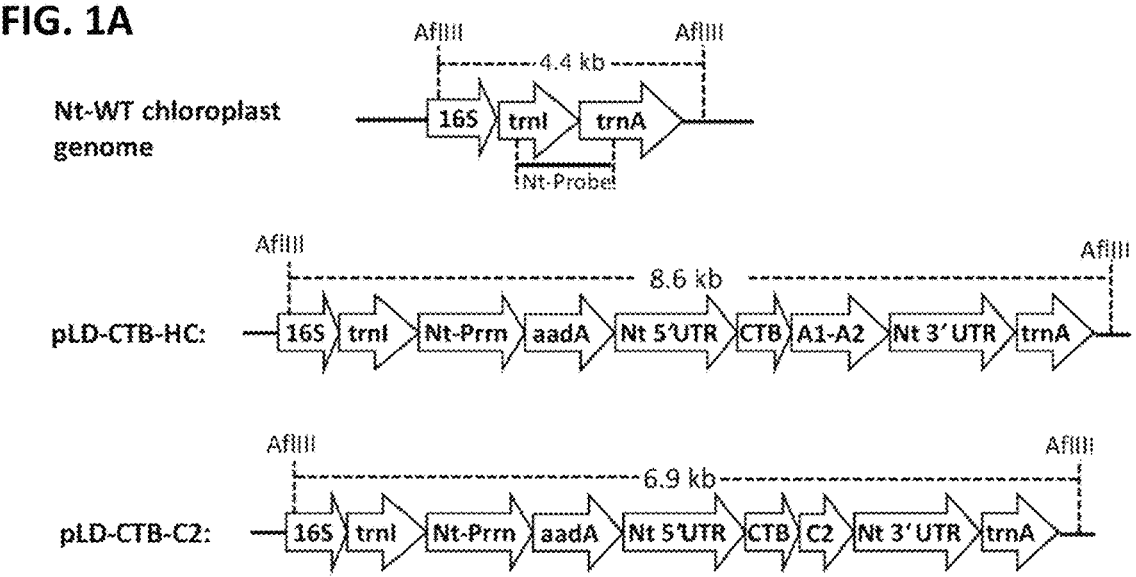

15 Claims, 33 Drawing Sheets
Specification includes a Sequence Listing.

(56) References Cited

OTHER PUBLICATIONS

International Search Report/Written Opinion, dated Apr. 9, 2015, issued in corresponding PCT/US2014/065994, filed Nov. 17, 2014.
Adair, Patrick et al., "Tolerance Induction in Hemophilia A Animal Models: Battling Inhibitors with Antigen-specific Immunotherapies", Discovery Medicine, 15(84): pp. n-n (2013).
Berntorp, Erik et al., "Modern haemophilia care", The Lancet, 379: 1447-1456 (2012).
Boyhan, Diane et al., "Low-cost production of proinsulin in tobacco and lettuce chloroplasts for injectable or oral delivery of functional insulin and C-peptide", Plant Biotechnol. J., 9(5): 585-598 (2011).
Cao, Ou et al., "Impact of the Underlying Mutation and the Route of Vector Administration on Immune Responses to Factor IX in Gene Therapy for Hemophilia B", Molecular Therapy, 17(10): 1733-1742 (2009).
Cao, Ou et al., "Induction and role of regulatory CD4+CD25+ T cells in tolerance to the transgene product following hepatic in vivo gene transfer", Blood, 110(4): 1132-1140 (2007).
Cao, Ou et al., "Immune deviation by mucosal antigen administration suppresses gene-transfer-induced inhibitor formation to factor IX", Blood, 108(2): 480-486 (2006).
Clarke, Jihong et al., "Plastid biotechnology for crop production: present status and future perspectives", Plant Mol. Biol., 76: 211-220 (2011).
Daniell, Henry et al., "Plant-made vaccine antigens and biopharmaceuticals", Trends Plant Sci., 14(12): 669-679 (2009).
Daniell, Henry et al., "Expression of the Native Cholera Toxin B Subunit Gene and Assembly as Functional Oligomers in Transgenic Tobacco Chloroplasts", J. Mol. Biol., 311(5): 1001-1009 (2001).
Dimichele, Donna M., "Immune tolerance in haemophilia: the long journey to the fork in the road", British Journal of Haematology, 159: 123-134 (2012).
Dorner, Andrew J. et al., "The Relationship of N-linked Glycosylation and Heavy Chain-binding Protein Association with the Secretion of Glycoproteins", The Journal of Cell Biology, 105: 2665-2674 (1987).
Ehrenforth, S. et al., "Incidence of development of factor VIII and factor IX inhibitors in haemophiliacs", Lancet, 339: 594 (1992).
Gagliani, Nicola et al., "Coexpression of CD49b and LAG-3 identifies human and mouse T regulatory type 1 cells", Nature Medicine, 19(6): 739-746 (2013).
Graw, Jochen et al., "Jaemophilia A: From Mutation Analysis to New Therapies", Nature, 6: 488-501 (2005).
DeHaan, L. et al., "Role of GM1 binding in the mucosal immunogenicity and adjuvant activity of the *Escherichia coli* heat-labile enterotoxin and its B subunit", Immunology, 94: 424-430 (1998).
Hoffman, Brad E. et al., "Nonredundant Roles of IL-10 and TGF-B in Suppression of Immune Responses to Hepatic AAV-Factor IX Gene Transfer", Molecular Therapy, 19(7): 1263-1272 (2011).
Jayadharan, Giridhara et al., "Hemophilia: Disease, Diagnosis and Treatment", J. Genet. Syndr. Gene Ther., S1 (2011).
Kohli, Neha et al., "Oral Delivery of Bioencapsulated Proteins Across Blood-Brain and Blood-Retinal Barriers", Molecular Therapy, 22(3): 535-546 (2014).
Kumar, Shashi et al., "Remodeling the isoprenoid pathway in tobacco by expressing the cytoplasmic mevalonate pathway in chloroplasts", Metabolic Engineering, 14: 19-28 (2012).
Kwon, Kwang-Chul et al., "Oral delivery of bioencapsulated exendin-4 expressed in chloroplasts lowers blood glucose level in mice and stimulates insulin secretion in beta-TC6 cells", Plant Biotechnology Journal, 11: 77-86 (2013).
Kwon, Kwang-Chul et al., "Oral delivery of human biopharmaceuticals, autoantigens and vaccine antige bioencapsulated in plant cells", Advanced Drug Delivery Reviews, 65: 782-799 (2013).
Lakshmi, Priya et al., "Low Cost Tuberculosis Vaccine Antigens in Capsules: Expression in Chloroplasts, Bio-Encapsulation, Stability and Functional Evaluation in Vitro", PLOS ONE, 8(1): e54708 (2013).

Lei, Tie et al., "Induction of tolerance to factor VIII inhibitors by gene therapy with immunodominant A2 and C2 domains presented by B cells as Ig fusion proteins", Blood, 105(12): 4865-4870 (2005).
Limaye, Arati et al., "Receptor-mediated oral delivery of a bioencapsulated green fluorescent protein expressed in transgenic chloroplasts into the mouse circulatory system", FASEB J., 20(7): 959-961 (2006).
Markovitz, Rebecca et al., "The diversity of the immune response to the A2 domain of human factor VIII", Blood, 121(14): 2785-2795 (2013).
Markusic, David M. et al., "Effective gene therapy for haemophilic mice with pathogenic factor IX antibodies", EMBO Mol. Med., 5: 1698-1709 (2013).
Meeks, Shannon L. et al., Antihuman factor VIII C2 domain antibodies in hemophilia A mice recognize a functionally complex continuous spectrum of epitopes dominated by inhibitors of factor VIII activation, Blood, 110: 4234-4242 (2007).
Miao, Carol H. et al., "Immunomodulation for inhibitors in hemophilia A: the important role of Treg cells", Expert Rev. Hematol., 3(4): 469-483 (2010).
Moghimi, B. et al., "Induction of tolerance to factor VIII by transient co-administration with rapamycin", J. Thromb. Haemost., 9: 1524-33 (2011).
Oliveira, Vanessa G. et al., "Adjuvant facilitates tolerance induction to factor VIII in hemophilic mice through a Foxp3-independent mechanism that relies on IL-10", Blood, 121(19): 3936-3945 (2013).
Pipe, S.W. et al., "Functional roles of the factor VIII B domain", Haemophilia, 15: 1187-1196 (2009).
Pratt, Kathleen P. et al., "B-Cell and T-Cell Tpitopes in Anti-factor VIII Immune Responses", Clinic Rev. Allerg. Immunol., 37: 80-95 (2009).
Pratt, Kathleen P., "Inhibitory antibodies in hemophilia A", Hematology, 19(5): 399-405 (2012).
Qadura, M. et al., "Immunoglobulin isotypes and functional anti-FVIII antibodies in response to FVIII treatment in Balb/c and C57BL/6 haemophilia A mice", Haemophilia, 17: 288-295 (2011).
Rawle, F.E. et al., "Induction of partial immune tolerance to factor VIII through prior mucosal exposure to the factor VIII C2 domain", J. Thromb. Haemost., 4: 2172-2179 (2006).
Roberts, Sean A., Engineering Factor Viii for Hemophilia Gene Therapy, J. Genet. Syndro. Gene Ther., S:1 (2011).
Sabatino, Denise E., "Animal Models in Hemophilia", Progress in Molecular Biology and Translational Science, 105: 151-209 (2012).
Sack, Brandon K. et al., "Transient B Cell Depletion or Improved Transgene Expression by Codon Optimization Promote Tolerance to Factor VIII in Gene Therapy", PLoS ONE, 7(5): e37671 (2012).
Scott, David W. et al., "Progress toward inducing immunologic tolerance to factor VIII", Blood, 121(22): 4449-4456 (2013).
Steinitz, Katharina et al., "CD4+ T-cell epitopes associated with antibody responses after intravenously and subcutaneously applied human FVIII in humanized hemophilic E17", Blood, 119(17): 4073-4082 (2012).
Tsuji, Takao et al., "Monomer of the B Subunit of Heat-Labile Enterotoxin from Enterotoxigenic *Escherichia coli* Has Little Ability to Bind to GM1 Ganglioside Compared to Its Coligenoid", Microbiol. Immunol., 39(10): 817-819 (1995).
Vehar, Gordon A. et al., "Structure of human factor VIII", Nature, 312: 337-342 (1984).
Verma, Dheeraj et al., "A protocol for expression of foreign genes in chloroplasts", Nature Protocols, 3(4): 739 (2008).
Verma, Dheeraj et al., "Oral delivery of bioencapsulated coagulation factor IX prevents inhibitor formation and fatal anaphylaxis in hemophilia B mice", PNAS, 107(15): 7101-7106 (2010).
Wang, Miaomei et al., "Mechanism of oral tolerance induction to therapeutic proteins", Advanced Drug Delivery Reviews, 65: 759-773 (2013).
Weiner, Howard L. et al., "Oral tolerance", Immunological Reviews, 241: 241-259 (2011).
Wroblewska, A. et al., "Dangerous liaisons: how the immune system deals with factor VIII", J. Thromb. Haemost., 11:47-55 (2013).
Ruhlman, Tracey et al., "Expression of cholera toxin B-proinsulin fusion protein in lettuce and tobacco chloroplasts—oral adminis-

(56) References Cited

OTHER PUBLICATIONS tration protects against development of insulitis in non-obese diabetic mice", Plant Biotechnology Journal, 5: 495-510 (2007).
Ruhlman, Tracey et al., "The Role of Heterologous Chloroplast Sequence Elements in Transgene Integration and Expression", Plant Physiology, 152: 2088-2104 (2010).
Daniell, Henry et al., "Optimization of codon composition and regulatory elements for expression of human insulin like growth factor-I in transgenic chloroplasts and evaluation of structural identity and function", BMC Biotechnology, 9: 33 (2009).

BALB/c

FIG. 7A
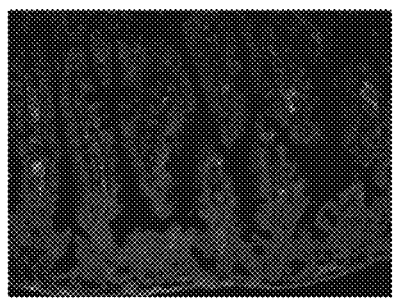
DAPI FVIII CD11c
FIG. 7B
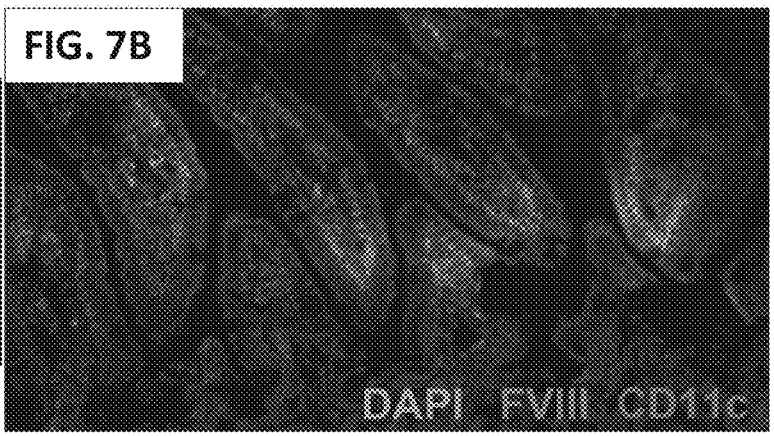
DAPI FVIII CD11c
FIG. 7C
FVIII
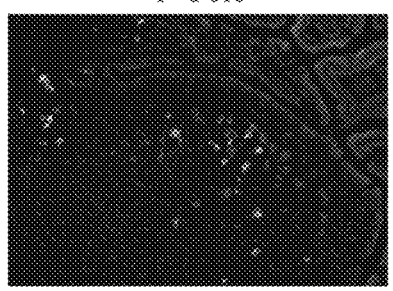
CD11c
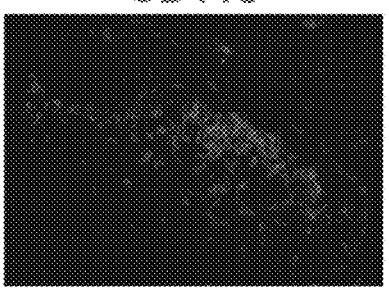
FVIII / CD11c
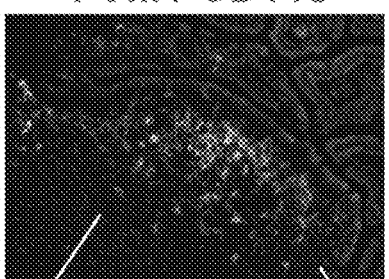
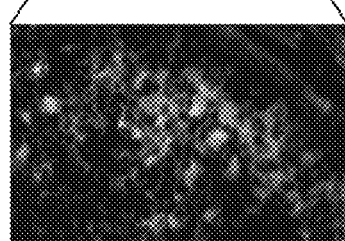
FIG. 7D
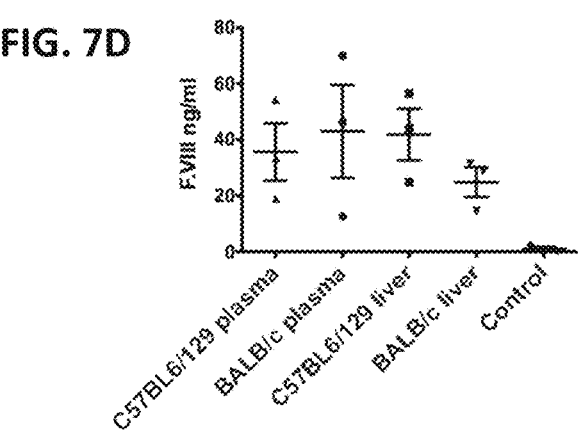

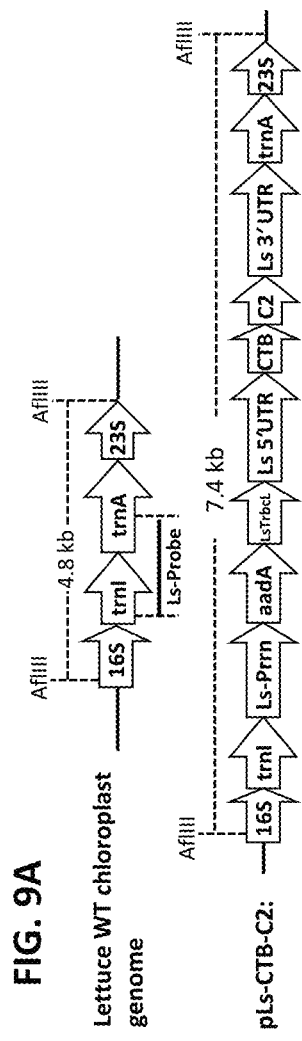
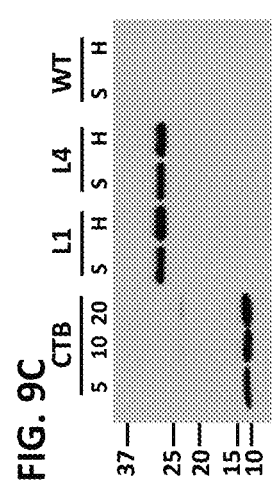
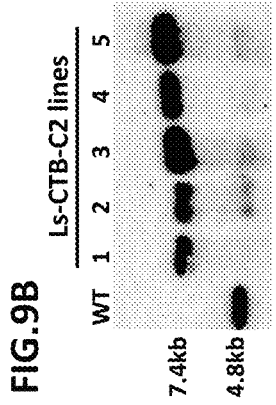
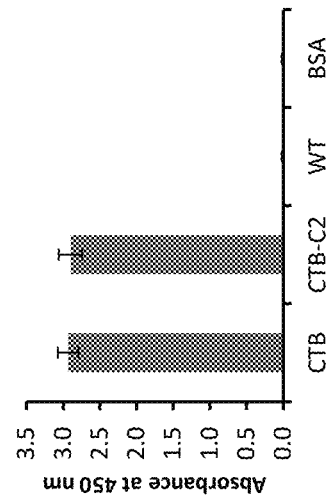
FIG. 9A
FIG. 9B
FIG. 9C
FIG. 9D

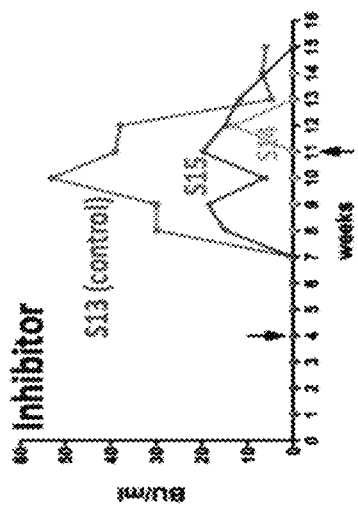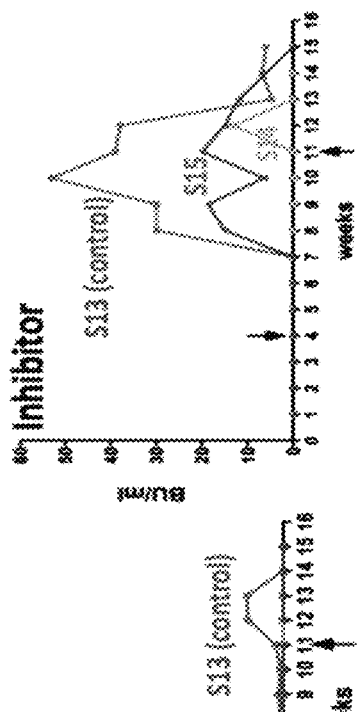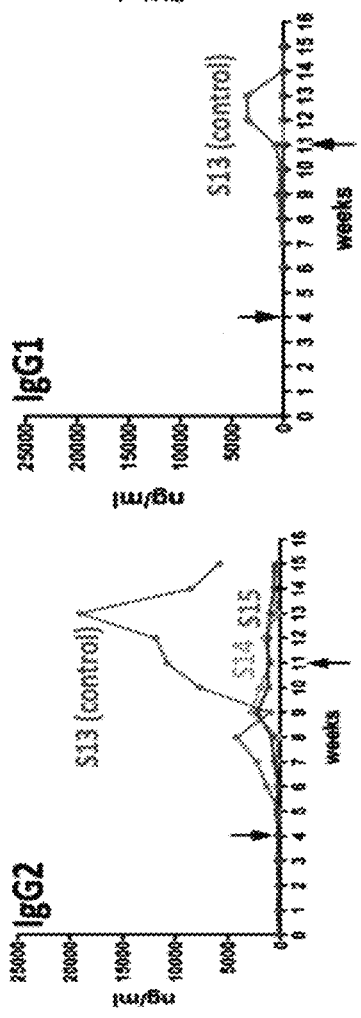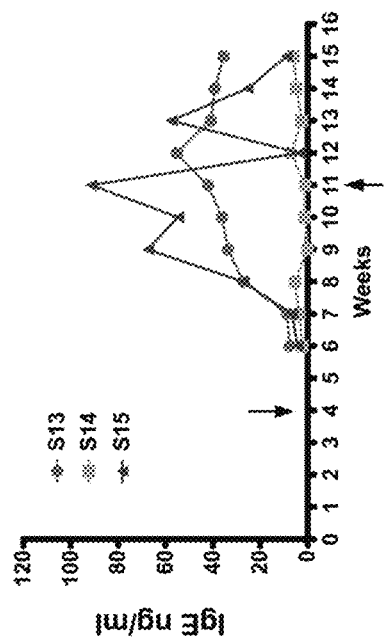

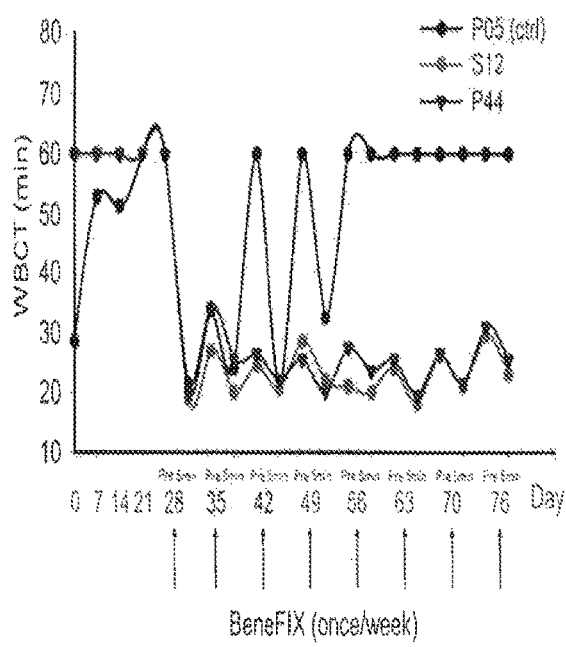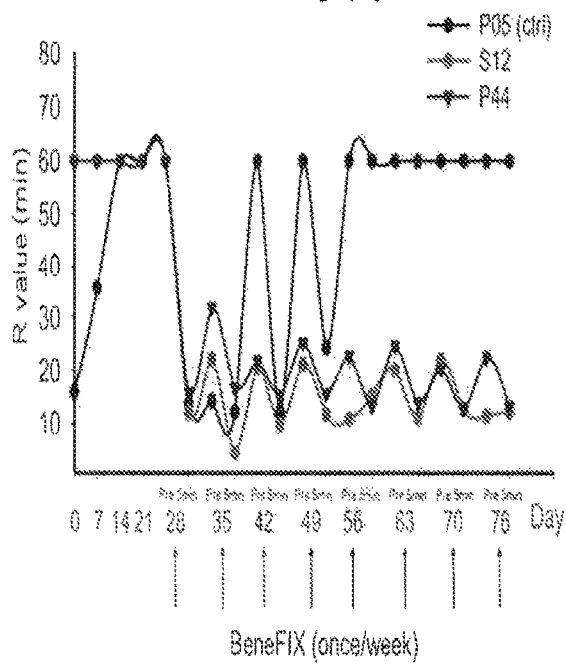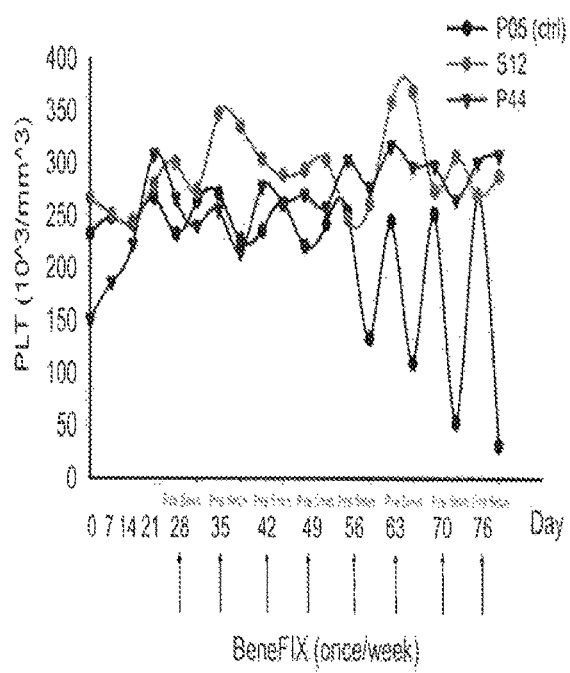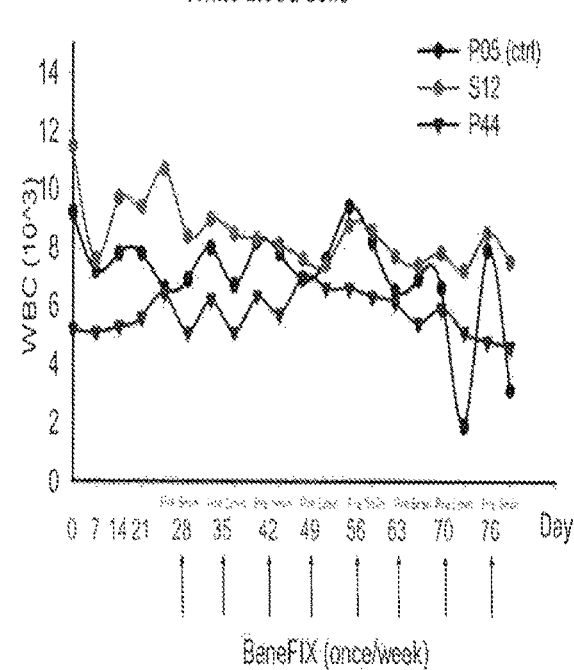

FIG. 18B

Expression cassette for native and codon optimized FVIII Light chain (LC)

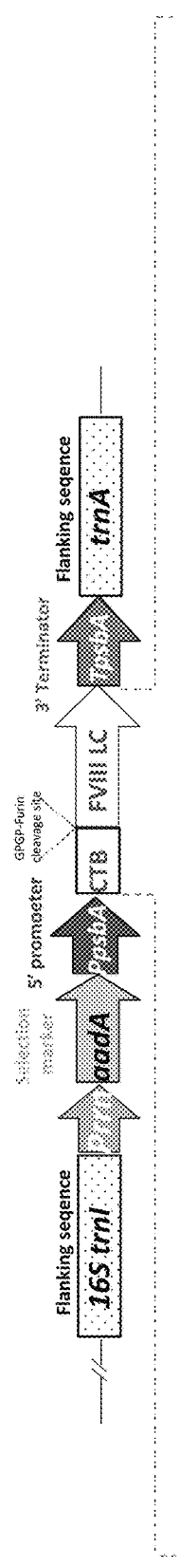

CTB: Native sequence of cholera non-toxic B subunit (312 bp)
FVIII LC: Human blood clotting factor 8 light chain (2055 bp)
Nat: Native sequence (2055 bp)
CO-N: Codon-optimized sequence (new algorithm of optimizer)
(GPGPRRKRSV): codon optimized GPGP-furin cleavage site -SV
Two amino acid (SV) were added behind furin cleavage site (RRKR) to facilitate the cleavage CTB-FVIII HC (N8, CO): 100 kDa
CTB-FVIII LC (CO): 92 kDa
CTB-FVIII SC (CO): 179 kDa

| Plant | Construct | Batch | Amount (g) for each batch | Total amount (g) |
|---|---|---|---|---|
| Lettuce (lyophilized, ground) | CTB-FVIII HC BDD (CO, LS) | L05182015<br>L06232015<br>L07122015<br>L07272015<br>L08152015<br>L12282015<br>L01122016-1<br>L01122016-2<br>L01292016

FIG. 26A

Sequence of the PTD-GPGP.Furin-Propeptide.FIX
Three point mutations "V10K, R338L, S77W were highlighted with rectangle.

```
5'  ctt aac GGT aag GTT GAT gct TTC TGT ggt gga TCC atc gta AAT GAA AAA TGG ATT GTA ACT GCT gca CAC
                                                                                                      792
3'  gaa ttg CCA ttc CAA CTA cga AAG ACA cca cct AGG tag cat TTA CTT TTT ACC TAA CAT TGA CGA cgt GTG
                                            FIX
    L   N   G   K   V   D   A   F   C   G   G   S   I   V   N   E   K   W   I   V   T   A   A   H 5'  TGT gta GAA aca GGT GTT AAA atc act gta gtt gct GGT GAA cac aac ATT gag gaa act gag CAT act gaa
                                                                                                      864
3'  ACA cat CTT tgt CCA CAA TTT tag tga cat caa cga CCA CTT gtg ttg TAA ctc ctt tga ctc GTA tga ctt
                                            FIX
    C   V   E   T   G   V   K   I   T   V   V   A   G   E   H   N   I   E   E   T   E   H   T   E 5'  CAA aaa cgt AAT gtt ATT cgt ATC ata cca CAC CAC AAC tat AAT gct gcc ATT AAC aaa tac aat cac gat
                                                                                                      936
3'  GTT ttt gca TTA caa TAA gca TAG tat ggt GTG GTG TTG ata TTA cga cgg TAA TTG ttt atg tta gtg cta
                                            FIX
    Q   K   R   N   V   I   R   I   I   P   H   H   N   Y   N   A   A   I   N   K   Y   N   H   D 5'  ata gcc cta ttg GAA cta gat GAA cct cta gtt ctt AAC agt tat gta acc cca ATC tgt ATT GCT gat aaa
                                                                                                      1008
3'  tat cgg gat aac CTT gat cta CTT gga gat caa gaa TTG tca ata cat tgg ggt TAG aca TAA CGA cta ttt
                                            FIX
    I   A   L   L   E   L   D   E   P   L   V   L   N   S   Y   V   T   P   I   C   I   A   D   K 5'  GAA tac acc aat ATC TTC ttg AAA ttc ggt TCT gga TAT gtt agc ggt TGG ggt cgt gtt TTC cat AAA ggt
                                                                                                      1080
3'  CTT atg tgg tta TAG AAG aac TTT aag cca AGA cct ATA caa tcg cca ACC cca gca caa AAG gta TTT cca
                                            FIX
    E   Y   T   N   I   F   L   K   F   G   S   G   Y   V   S   G   W   G   R   V   F   H   K   G 5'  cga tct GCT TTA gta CTT caa TAC ttg AGA gta cct tta gta gat cgt gct act TGT cta tta TCT act aaa
                                                                                                      1152
3'  gct aga CGA AAT cat GAA gtt ATG aac TCT cat gga aat cat cta gca cga tga ACA gat aat AGA tga ttt
                                            FIX
    R   S   A   L   V   L   Q   Y   L   R   V   P   L   V   D   R   A   T   C   L   L   S   T   K
                                                                                      R338L 5'  ttc ACC att tac AAC AAC ATG TTC TGT GCA ggc TTC CAT GAA gga GGT cgt GAT agt TGT CAA ggt GAT tct
                                                                                                      1224
3'  aag TGG taa atg TTG TTG TAC AAG ACA CGT ccg AAG GTA CTT cct CCA gca CTA tca ACA GTT cca CTA aga
                                            FIX
    F   T   I   Y   N   N   M   F   C   A   G   F   H   E   G   G   R   D   S   C   Q   G   D   S 5'  gga ggt cct cac GTT ACT gag gtt GAA ggt act TGG ttt tta acc ggt atc ATT tct TGG GGT GAA gaa TGT
                                                                                                      1296
3'  cct cca gga gtg CAA TGA ctc caa CTT cca tga ACC aaa aat tgg cca tag TAA aga ACC CCA CTT ctt ACA
                                            FIX
    G   G   P   H   V   T   E   V   E   G   T   W   F   L   T   G   I   S   W   G   E   E   C
                                                S377W 5'  gct ATG AAA ggt AAA tac GGC att TAT act aaa gtt tct cgt tac gta aat TGG ATT aaa GAA AAG act aaa
                                                                                                      1368
3'  cga TAC TTT cca TTT atg CCG taa ATA tga ttt caa aga gca atg cat tta ACC TAA ttt CTT TTC tga ttt
                                            FIX
    A   M   K   G   K   Y   G   I   Y   T   K   V   S   R   Y   V   N   W   I   K   E   K   T   K 5'  tta acc TAA
                                                                                                      1377
3'  aat tgg ATT
    FIX
    L   T
```

Propep-FIX-Rv: gaTCTAGA tta ggt taa ttt agt ctt ttc  FIG. 26B

Fig. 26C

DNA sequence (codon optimized) of the Propeptide.FIX.KLW

ATGactgtaTTTttgGATCATGAAaatgctAACAAAATTcttaaccgccctaaacgtTATaactctGGTAAAttaGAAgagttcA
AAcagggaaatttggagcgcGAATGCATGGAGGAAaaaTGTtctttcGAAgaggctcgtGAAGTTTTTGAGAACACTGAA
cgaaccaccGAAttcTGGaaaCAGTATgtaGATggcGACcaaTGTgaatccaacccttgtctaAATGGCggtagttgtaaagacga
tATTaacagctacGAATGCTGGTGTccttttggtttcGAAggcaaaaatTGTGAActaGATGTAactTGTAACATTaaaAATgg
tcgttgcgaacaattcTGTAAAaactccGCTgacaataaagtagtttgctctTGTACTgaaggtTATcgtCTTgctGAAaatcaaaaaa
gtTGTgagcctgcagttccttcCCATGTggtcgtgtaagtGTTtctcagACTagcaaactaacaagaGCTgaaaccgtattcCCTGATg
ttgacTATGTAAATagtACTGAGGCTGAAacaATCTTGGATaacattaccCAAagcactCAAtctttcAATgatTTTACTcgtgt
aGTTGGTggcGAAGATgcaaagCCAGGTCAATTCCCTTGGcaagtagttcttaacGGTaagGTTGATgctTTCTGTggtgg
aTCCatcgtaAATGAAAAATGGATTGTAACTGCTgcaCACTGTgtaGAAacaGGTGTTAAAatcactgtagttgctGGTG
AAcacaacATTgaggaaactgagCATactgaaCAAaaacgtAATgttATTcgtATCataccaCACCACAACtatAATgctgccATT
AACaaatacaatcacgatatagccctattgGAActagatGAAcctctagttcttAACagttatgtaaccccaATCtgtATTGCTgataaa
GAAtacaccaatATCTTCcttgAAAttcggtTCTggaTATgttagcggtTGGggtcgtgttTTCcatAAAggtcgatctGCTTTAgtaC
TTcaaTACttgAGAgtaccttagtagatcgtgctactTGTctattaTCTactaaattcACCatttacAACAACATGTTCTGTGCAgg
cTTCCATGAAggaGGTcgtGATagtTGTCAAggtGATtctggaggtcctcacGTTACTgaggttGAAggtactTGGtttttaaccg
gtatcATTtctTGGGGTGAAgaaTGTgctATGAAAggtAAAtacGGCattTATactaaagtttctcgttacgtaaatTGGATTaaa
GAAAAGactaaattaaccTAA

FIG. 26D

Protein Sequence of the Propeptide.FIX.KLW

MTVFLDHENANKILNRPKRYNSGKLEEFKQGNLERECMEEKCSFEEAREVFENTER
TTEFWKQYVDGDQCESNPCLNGGSCKDDINSYECWCPFGFEGKNCELDVTCNIKN
GRCEQFCKNSADNKVVCSCTEGYRLAENQKSCEPAVPFPCGRVSVSQTSKLTRAET
VFPDVDYVNSTEAETILDNITQSTQSFNDFTRVVGGEDAKPGQFPWQVVLNGKVD
AFCGGSIVNEKWIVTAAHCVETGVKITVVAGEHNIEETEHTEQKRNVIRIIPHHNYN
AAINKYNHDIALLELDEPLVLNSYVTPICIADKEYTNIFLKFGSGYVSGWGRVFHKGRS
ALVLQYLRVPLVDRATCLLSTKFTIYNNMFCAGFHEGGRDSCQGDSGGPHVTEVEG
TWFLTGIISWGEECAMKGKYGIYTKVSRYVNWIKEKTKLT

FIG. 26E

Protein Sequence of the PTD-GPGP.Furin-Propeptide.FIX.KLW

MRHIKIWFQNRRMKWKKGPGPRRKRTVFLDHENANKILNRPKRYNSGKLEEFKQ
GNLERECMEEKCSFEEAREVFENTERTTEFWKQYVDGDQCESNPCLNGGSCKDDI
NSYECWCPFGFEGKNCELDVTCNIKNGRCEQFCKNSADNKVVCSCTEGYRLAENQ
KSCEPAVPFPCGRVSVSQTSKLTRAETVFPDVDYVNSTEAETILDNITQSTQSFNDFT
RVVGGEDAKPGQFPWQVVLNGKVDAFCGGSIVNEKWIVTAAHCVETGVKITVVA
GEHNIEETEHTEQKRNVIRIIPHHNYNAAINKYNHDIALLELDEPLVLNSYVTPICIAD
KEYTNIFLKFGSGYVSGWGRVFHKGRSALVLQYLRVPLVDRATCLLSTKFTIYNNMFC
AGFHEGGRDSCQGDSGGPHVTEVEGTWFLTGIISWGEECAMKGKYGIYTKVSRYV
NWIKEKTKLT

SEQUENCE LISTING

<160> NUMBER OF SEQ ID NOS: 22

<210> SEQ ID NO 1
<211> LENGTH: 2351
<212> TYPE: PRT
<213> ORGANISM: Homo sapiens

<400> SEQUENCE: 1

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365
```

```
Leu Thr Asp Ser Glu Met Asp Val Val Arg Phe Asp Asp Asn Ser
    370             375             380

Pro Ser Phe Ile Gln Ile Arg Ser Val Ala Lys Lys His Pro Lys Thr
385             390             395             400

Trp Val His Tyr Ile Ala Ala Glu Glu Asp Trp Asp Tyr Ala Pro
            405             410             415

Leu Val Leu Ala Pro Asp Asp Arg Ser Tyr Lys Ser Gln Tyr Leu Asn
            420             425             430

Asn Gly Pro Gln Arg Ile Gly Arg Lys Tyr Lys Val Arg Phe Met
        435             440             445

Ala Tyr Thr Asp Glu Thr Phe Lys Thr Arg Glu Ala Ile Gln His Glu
    450             455             460

Ser Gly Ile Leu Gly Pro Leu Leu Tyr Gly Glu Val Gly Asp Thr Leu
465             470             475             480

Leu Ile Ile Phe Lys Asn Gln Ala Ser Arg Pro Tyr Asn Ile Tyr Pro
            485             490             495

His Gly Ile Thr Asp Val Arg Pro Leu Tyr Ser Arg Arg Leu Pro Lys
            500             505             510

Gly Val Lys His Leu Lys Asp Phe Pro Ile Leu Pro Gly Glu Ile Phe
            515             520             525

Lys Tyr Lys Trp Thr Val Thr Val Glu Asp Gly Pro Thr Lys Ser Asp
            530             535             540

Pro Arg Cys Leu Thr Arg Tyr Tyr Ser Ser Phe Val Asn Met Glu Arg
545             550             555             560

Asp Leu Ala Ser Gly Leu Ile Gly Pro Leu Leu Ile Cys Tyr Lys Glu
                565             570             575

Ser Val Asp Gln Arg Gly Asn Gln Ile Met Ser Asp Lys Arg Asn Val
            580             585             590

Ile Leu Phe Ser Val Phe Asp Glu Asn Arg Ser Trp Tyr Leu Thr Glu
            595             600             605

Asn Ile Gln Arg Phe Leu Pro Asn Pro Ala Gly Val Gln Leu Glu Asp
    610             615             620

Pro Glu Phe Gln Ala Ser Asn Ile Met His Ser Ile Asn Gly Tyr Val
625             630             635             640

Phe Asp Ser Leu Gln Leu Ser Val Cys Leu His Glu Val Ala Tyr Trp
            645             650             655

Tyr Ile Leu Ser Ile Gly Ala Gln Thr Asp Phe Leu Ser Val Phe Phe
            660             665             670

Ser Gly Tyr Thr Phe Lys His Lys Met Val Tyr Glu Asp Thr Leu Thr
            675             680             685

Leu Phe Pro Phe Ser Gly Glu Thr Val Phe Met Ser Met Glu Asn Pro
    690             695             700

Gly Leu Trp Ile Leu Gly Cys His Asn Ser Asp Phe Arg Asn Arg Gly
705             710             715             720

Met Thr Ala Leu Leu Lys Val Ser Ser Cys Asp Lys Asn Thr Gly Asp
                725             730             735

Tyr Tyr Glu Asp Ser Tyr Glu Asp Ile Ser Ala Tyr Leu Leu Ser Lys
            740             745             750

Asn Asn Ala Ile Glu Pro Arg Ser Phe Ser Gln Asn Ser Arg His Pro
        755             760             765

Ser Thr Arg Gln Lys Gln Phe Asn Ala Thr Thr Ile Pro Glu Asn Asp
770             775             780

Ile Glu Lys Thr Asp Pro Trp Phe Ala His Arg Thr Pro Met Pro Lys
```

-continued

```
            785                 790                 795                 800
Ile Gln Asn Val Ser Ser Ser Asp Leu Leu Met Leu Arg Gln Ser
                    805                 810                 815

Pro Thr Pro His Gly Leu Ser Leu Ser Asp Leu Gln Glu Ala Lys Tyr
                820                 825                 830

Glu Thr Phe Ser Asp Asp Pro Ser Pro Gly Ala Ile Asp Ser Asn Asn
            835                 840                 845

Ser Leu Ser Glu Met Thr His Phe Arg Pro Gln Leu His His Ser Gly
        850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
        915                 920                 925

Pro Val His Tyr Asp Ser Gln Leu Asp Thr Thr Leu Phe Gly Lys Lys
    930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro Ala Leu Leu Thr Lys Asp Asn Ala
        995                 1000                1005

Leu Phe Lys Val Ser Ile Ser Leu Leu Lys Thr Asn Lys Thr Ser Asn
    1010                1015                1020

Asn Ser Ala Thr Asn Arg Lys Thr His Ile Asp Gly Pro Ser Leu Leu
1025                1030                1035                1040

Ile Glu Asn Ser Pro Ser Val Trp Gln Asn Ile Leu Glu Ser Asp Thr
                1045                1050                1055

Glu Phe Lys Lys Val Thr Pro Leu Ile His Asp Arg Met Leu Met Asp
            1060                1065                1070

Lys Asn Ala Thr Ala Leu Arg Leu Asn His Met Ser Asn Lys Thr Thr
        1075                1080                1085

Ser Ser Lys Asn Met Glu Met Val Gln Gln Lys Lys Glu Gly Pro Ile
    1090                1095                1100

Pro Pro Asp Ala Gln Asn Pro Asp Met Ser Phe Phe Lys Met Leu Phe
1105                1110                1115                1120

Leu Pro Glu Ser Ala Arg Trp Ile Gln Arg Thr His Gly Lys Asn Ser
                1125                1130                1135

Leu Asn Ser Gly Gln Gly Pro Ser Pro Lys Gln Leu Val Ser Leu Gly
            1140                1145                1150

Pro Glu Lys Ser Val Glu Gly Gln Asn Phe Leu Ser Glu Lys Asn Lys
        1155                1160                1165

Val Val Val Gly Lys Gly Glu Phe Thr Lys Asp Val Gly Leu Lys Glu
    1170                1175                1180

Met Val Phe Pro Ser Ser Arg Asn Leu Phe Leu Thr Asn Leu Asp Asn
1185                1190                1195                1200

Leu His Glu Asn Asn Thr His Asn Gln Glu Lys Lys Ile Gln Glu Glu
                1205                1210                1215
```

Ile Glu Lys Lys Glu Thr Leu Ile Gln Glu Asn Val Val Leu Pro Gln
                1220                1225                1230

Ile His Thr Val Thr Gly Thr Lys Asn Phe Met Lys Asn Leu Phe Leu
                1235                1240                1245

Leu Ser Thr Arg Gln Asn Val Glu Gly Ser Tyr Asp Gly Ala Tyr Ala
                1250                1255                1260

Pro Val Leu Gln Asp Phe Arg Ser Leu Asn Asp Ser Thr Asn Arg Thr
1265                1270                1275                1280

Lys Lys His Thr Ala His Phe Ser Lys Lys Gly Glu Glu Asn Leu
            1285                1290                1295

Glu Gly Leu Gly Asn Gln Thr Lys Gln Ile Val Glu Lys Tyr Ala Cys
                1300                1305                1310

Thr Thr Arg Ile Ser Pro Asn Thr Ser Gln Gln Asn Phe Val Thr Gln
                1315                1320                1325

Arg Ser Lys Arg Ala Leu Lys Gln Phe Arg Leu Pro Leu Glu Glu Thr
1330                1335                1340

Glu Leu Glu Lys Arg Ile Ile Val Asp Asp Thr Ser Thr Gln Trp Ser
1345                1350                1355                1360

Lys Asn Met Lys His Leu Thr Pro Ser Thr Leu Thr Gln Ile Asp Tyr
                1365                1370                1375

Asn Glu Lys Glu Lys Gly Ala Ile Thr Gln Ser Pro Leu Ser Asp Cys
                1380                1385                1390

Leu Thr Arg Ser His Ser Ile Pro Gln Ala Asn Arg Ser Pro Leu Pro
                1395                1400                1405

Ile Ala Lys Val Ser Ser Phe Pro Ser Ile Arg Pro Ile Tyr Leu Thr
                1410                1415                1420

Arg Val Leu Phe Gln Asp Asn Ser Ser His Leu Pro Ala Ala Ser Tyr
1425                1430                1435                1440

Arg Lys Lys Asp Ser Gly Val Gln Glu Ser Ser His Phe Leu Gln Gly
                1445                1450                1455

Ala Lys Lys Asn Asn Leu Ser Leu Ala Ile Leu Thr Leu Glu Met Thr
                1460                1465                1470

Gly Asp Gln Arg Glu Val Gly Ser Leu Gly Thr Ser Ala Thr Asn Ser
                1475                1480                1485

Val Thr Tyr Lys Lys Val Glu Asn Thr Val Leu Pro Lys Pro Asp Leu
                1490                1495                1500

Pro Lys Thr Ser Gly Lys Val Glu Leu Leu Pro Lys Val His Ile Tyr
1505                1510                1515                1520

Gln Lys Asp Leu Phe Pro Thr Glu Thr Ser Asn Gly Ser Pro Gly His
                1525                1530                1535

Leu Asp Leu Val Glu Gly Ser Leu Leu Gln Gly Thr Glu Gly Ala Ile
                1540                1545                1550

Lys Trp Asn Glu Ala Asn Arg Pro Gly Lys Val Pro Phe Leu Arg Val
                1555                1560                1565

Ala Thr Glu Ser Ser Ala Lys Thr Pro Ser Lys Leu Leu Asp Pro Leu
                1570                1575                1580

Ala Trp Asp Asn His Tyr Gly Thr Gln Ile Pro Lys Glu Glu Trp Lys
1585                1590                1595                1600

Ser Gln Glu Lys Ser Pro Glu Lys Thr Ala Phe Lys Lys Lys Asp Thr
                1605                1610                1615

Ile Leu Ser Leu Asn Ala Cys Glu Ser Asn His Ala Ile Ala Ala Ile
                1620                1625                1630

Asn Glu Gly Gln Asn Lys Pro Glu Ile Glu Val Thr Trp Ala Lys Gln
        1635                1640                1645

Gly Arg Thr Glu Arg Leu Cys Ser Gln Asn Pro Val Leu Lys Arg
    1650                1655                1660

His Gln Arg Glu Ile Thr Arg Thr Thr Leu Gln Ser Asp Gln Glu Glu
1665                1670                1675                1680

Ile Asp Tyr Asp Asp Thr Ile Ser Val Glu Met Lys Lys Glu Asp Phe
            1685                1690                1695

Asp Ile Tyr Asp Glu Asp Glu Asn Gln Ser Pro Arg Ser Phe Gln Lys
        1700                1705                1710

Lys Thr Arg His Tyr Phe Ile Ala Ala Val Glu Arg Leu Trp Asp Tyr
    1715                1720                1725

Gly Met Ser Ser Ser Pro His Val Leu Arg Asn Arg Ala Gln Ser Gly
    1730                1735                1740

Ser Val Pro Gln Phe Lys Lys Val Val Phe Gln Glu Phe Thr Asp Gly
1745                1750                1755                1760

Ser Phe Thr Gln Pro Leu Tyr Arg Gly Glu Leu Asn Glu His Leu Gly
            1765                1770                1775

Leu Leu Gly Pro Tyr Ile Arg Ala Glu Val Glu Asp Asn Ile Met Val
        1780                1785                1790

Thr Phe Arg Asn Gln Ala Ser Arg Pro Tyr Ser Phe Tyr Ser Ser Leu
    1795                1800                1805

Ile Ser Tyr Glu Glu Asp Gln Arg Gln Gly Ala Glu Pro Arg Lys Asn
    1810                1815                1820

Phe Val Lys Pro Asn Glu Thr Lys Thr Tyr Phe Trp Lys Val Gln His
1825                1830                1835                1840

His Met Ala Pro Thr Lys Asp Glu Phe Asp Cys Lys Ala Trp Ala Tyr
            1845                1850                1855

Phe Ser Asp Val Asp Leu Glu Lys Asp Val His Ser Gly Leu Ile Gly
        1860                1865                1870

Pro Leu Leu Val Cys His Thr Asn Thr Leu Asn Pro Ala His Gly Arg
    1875                1880                1885

Gln Val Thr Val Gln Glu Phe Ala Leu Phe Phe Thr Ile Phe Asp Glu
    1890                1895                1900

Thr Lys Ser Trp Tyr Phe Thr Glu Asn Met Glu Arg Asn Cys Arg Ala
1905                1910                1915                1920

Pro Ser Asn Ile Gln Met Glu Asp Pro Thr Phe Lys Glu Asn Tyr Arg
            1925                1930                1935

Phe His Ala Ile Asn Gly Tyr Ile Met Asp Thr Leu Pro Gly Leu Val
        1940                1945                1950

Met Ala Gln Asp Gln Arg Ile Arg Trp Tyr Leu Leu Ser Met Gly Ser
    1955                1960                1965

Asn Glu Asn Ile His Ser Ile His Phe Ser Gly His Val Phe Thr Val
    1970                1975                1980

Arg Lys Lys Glu Glu Tyr Lys Met Ala Leu Tyr Asn Leu Tyr Pro Gly
1985                1990                1995                2000

Val Phe Glu Thr Val Glu Met Leu Pro Ser Lys Ala Gly Ile Trp Arg
            2005                2010                2015

Val Glu Cys Leu Ile Gly Glu His Leu His Ala Gly Met Ser Thr Leu
        2020                2025                2030

Phe Leu Val Tyr Ser Asn Lys Cys Gln Thr Pro Leu Gly Met Ala Ser
    2035                2040                2045

Gly His Ile Arg Asp Phe Gln Ile Thr Ala Ser Gly Gln Tyr Gly Gln

-continued

```
                2050                2055                2060

Trp Ala Pro Lys Leu Ala Arg Leu His Tyr Ser Gly Ser Ile Asn Ala
2065                2070                2075                2080

Trp Ser Thr Lys Glu Pro Phe Ser Trp Ile Lys Val Asp Leu Leu Ala
            2085                2090                2095

Pro Met Ile Ile His Gly Ile Lys Thr Gln Gly Ala Arg Gln Lys Phe
            2100                2105                2110

Ser Ser Leu Tyr Ile Ser Gln Phe Ile Ile Met Tyr Ser Leu Asp Gly
                2115                2120                2125

Lys Lys Trp Gln Thr Tyr Arg Gly Asn Ser Thr Gly Thr Leu Met Val
            2130                2135                2140

Phe Phe Gly Asn Val Asp Ser Ser Gly Ile Lys His Asn Ile Phe Asn
2145                2150                2155                2160

Pro Pro Ile Ile Ala Arg Tyr Ile Arg Leu His Pro Thr His Tyr Ser
            2165                2170                2175

Ile Arg Ser Thr Leu Arg Met Glu Leu Met Gly Cys Asp Leu Asn Ser
                2180                2185                2190

Cys Ser Met Pro Leu Gly Met Glu Ser Lys Ala Ile Ser Asp Ala Gln
            2195                2200                2205

Ile Thr Ala Ser Ser Tyr Phe Thr Asn Met Phe Ala Thr Trp Ser Pro
            2210                2215                2220

Ser Lys Ala Arg Leu His Leu Gln Gly Arg Ser Asn Ala Trp Arg Pro
2225                2230                2235                2240

Gln Val Asn Asn Pro Lys Glu Trp Leu Gln Val Asp Phe Gln Lys Thr
                2245                2250                2255

Met Lys Val Thr Gly Val Thr Thr Gln Gly Val Lys Ser Leu Leu Thr
            2260                2265                2270

Ser Met Tyr Val Lys Glu Phe Leu Ile Ser Ser Ser Gln Asp Gly His
                2275                2280                2285

Gln Trp Thr Leu Phe Phe Gln Asn Gly Lys Val Lys Val Phe Gln Gly
            2290                2295                2300

Asn Gln Asp Ser Phe Thr Pro Val Val Asn Ser Leu Asp Pro Pro Leu
2305                2310                2315                2320

Leu Thr Arg Tyr Leu Arg Ile His Pro Gln Ser Trp Val His Gln Ile
            2325                2330                2335

Ala Leu Arg Met Glu Val Leu Gly Cys Glu Ala Gln Asp Leu Tyr
            2340                2345                2350

<210> SEQ ID NO 2
<211> LENGTH: 4
<212> TYPE: PRT
<213> ORGANISM: Artificial Sequence
<220> FEATURE:
<223> OTHER INFORMATION: hinge sequence

<400> SEQUENCE: 2

Gly Pro Gly Pro
1

<210> SEQ ID NO 3
<211> LENGTH: 4
<212> TYPE: PRT
<213> ORGANISM: Artificial Sequence
<220> FEATURE:
<223> OTHER INFORMATION: furin cleavage site

<400> SEQUENCE: 3
```

Arg Arg Lys Arg
1

<210> SEQ ID NO 4
<211> LENGTH: 30
<212> TYPE: DNA
<213> ORGANISM: Artificial Sequence
<220> FEATURE:
<223> OTHER INFORMATION: NdeI-CTB-Fw primer

<400> SEQUENCE: 4
ttcatatgac acctcaaaat attactgatt                                   30

<210> SEQ ID NO 5
<211> LENGTH: 31
<212> TYPE: DNA
<213> ORGANISM: Artificial Sequence
<220> FEATURE:
<223> OTHER INFORMATION: XbaI-FIX-Rv primer

<400> SEQUENCE: 5
gatctagatt aagtgagctt tgtttttttcc t                                31

<210> SEQ ID NO 6
<211> LENGTH: 312
<212> TYPE: DNA
<213> ORGANISM: Artificial Sequence
<220> FEATURE:
<223> OTHER INFORMATION: cholera non-toxic B subunit

<400> SEQUENCE: 6
atgacacctc aaaatattac tgatttgtgt gcagaatacc acaacacaca aatacatacg   60
ctaaatgata agatattttc gtatacagaa tctctagctg aaaaagaga gatggctatc  120 attactttta agaatggtgc aacttttcaa gtagaagtac caggtagtca acatatagat  180
tcacaaaaaa aagcaattga aaggatgaag gataccctga ggattgcata tcttactgaa  240
gctaaagtcg aaaagttatg tgtatggaat aataaaacgc tcatgcgat tgccgcaatt  300 agtatggcaa at                                                     312

<210> SEQ ID NO 7
<211> LENGTH: 30
<212> TYPE: DNA
<213> ORGANISM: Artificial Sequence
<220> FEATURE:
<223> OTHER INFORMATION: GPGP-furin cleavage site-SV

<400> SEQUENCE: 7
gggcccgggc cccggcgtaa acgttctgtt                                   30

<210> SEQ ID NO 8
<211> LENGTH: 2265
<212> TYPE: DNA
<213> ORGANISM: Homo sapien

<400> SEQUENCE: 8
gccaccagaa gatactacct gggtgcagtg gaactgtcat gggactatat gcaaagtgat   60
ctcggtgagc tgcctgtgga cgcaagattt cctcctagag tgccaaaatc ttttccattc  120
aacacctcag tcgtgtacaa aaagactctg tttgtagaat tcacggatca ccttttcaac  180
atcgctaagc caaggccacc ctggatgggt ctgctaggtc ctaccatcca ggctgaggtt  240
tatgatacag tggtcattac acttaagaac atggcttccc atcctgtcag tcttcatgct  300

```
gttggtgtat cctactggaa agcttctgag ggagctgaat atgatgatca gaccagtcaa        360
agggagaaag aagatgataa agtcttccct ggtggaagcc atacatatgt ctggcaggtc        420
ctgaaagaga atggtccaat ggcctctgac ccactgtgcc ttacctactc atatctttct        480
catgtggacc tggtaaaaga cttgaattca ggcctcattg gagccctact agtatgtaga        540
gaagggagtc tggccaagga aaagacacag accttgcaca aatttatact actttttgct        600
gtatttgatg aagggaaaag ttggcactca gaaacaaaga actccttgat gcaggatagg        660
gatgctgcat ctgctcgggc ctggcctaaa atgcacacag tcaatggtta tgtaaacagg        720
tctctgccag gtctgattgg atgccacagg aaatcagtct attggcatgt gattggaatg        780
ggcaccactc ctgaagtgca ctcaatattc ctcgaaggtc acacatttct tgtgaggaac        840
catcgccagg cgtccttgga aatctcgcca ataactttcc ttactgctca aacactcttg        900
atggaccttg acagtttct actgttttgt catatctctt cccaccaaca tgatggcatg        960
gaagcttatg tcaaagtaga cagctgtcca gaggaacccc aactacgaat gaaaaataat       1020
gaagaagcgg aagactatga tgatgatctt actgattctg aaatggatgt ggtcaggttt       1080
gatgatgaca actctccttc ctttatccaa attcgctcag ttgccaagaa gcatcctaaa       1140
acttgggtac attacattgc tgctgaagag gaggactggg actatgctcc cttagtcctc       1200
gcccccgatg acagaagtta taaaagtcaa tatttgaaca atggccctca gcggattggt       1260
aggaagtaca aaaaagtccg atttatggca tacacagatg aaacctttaa gactcgtgaa       1320
gctattcagc atgaatcagg aatcttggga ccttttacttt atggggaagt tggagacaca       1380
ctgttgatta tatttaagaa tcaagcaagc agaccatata acatctaccc tcacggaatc       1440
actgatgtcc gtccttttgta ttcaaggaga ttaccaaaag gtgtaaaaca tttgaaggat       1500
tttccaattc tgccaggaga aatattcaaa tataaatgga cagtgactgt agaagatggg       1560
ccaactaaat cagatcctcg gtgcctgacc cgctattact ctagtttcgt taatatggag       1620
agagatctag cttcaggact cattggcccct ctcctcatct gctacaaaga atctgtagat       1680
caaagaggaa accagataat gtcagacaag aggaatgtca tcctgttttc tgtatttgat       1740
gagaaccgaa gctggtacct cacagagaat atacaacgct tctctcccaa tccagctgga       1800
gtgcagcttg aggatccaga gttccaagcc tccaacatca tgcacagcat caatggctat       1860 gttttgata gtttgcagtt gtcagtttgt ttgcatgagg tggcatactg gtacattcta       1920
agcattggag cacagactga cttcctttct gtcttcttct ctggatatac cttcaaacac       1980
aaaatggtct atgaagacac actcacccta ttcccattct caggagaaac tgtcttcatg       2040
tcgatggaaa acccaggtct atggattctg ggtgccaca actcagactt tcggaacaga       2100
ggcatgaccg ccttactgaa ggtttctagt tgtgacaaga acactggtga ttattacgag       2160
gacagttatg aagatatttc agcatacttg ctgagtaaaa acaatgccat tgaaccaaga       2220
agcttctccc agaatccacc agtcttgaaa cgccatcaac gctaa                      2265

<210> SEQ ID NO 9
<211> LENGTH: 30
<212> TYPE: DNA
<213> ORGANISM: Artificial Sequence
<220> FEATURE:
<223> OTHER INFORMATION: codon optimized GPGP-furin cleavage site-SV

<400> SEQ

```
<210> SEQ ID NO 10
<211> LENGTH: 2265
<212> TYPE: DNA
<213> ORGANISM: Artificial Sequence
<220> FEATURE:
<223> OTHER INFORMATION: codon optimized FVIII HC

<400> SEQUENCE: 10
gcaactcgtc gttactatct aggagctgtt gaactaagtt gggattatat gcaatctgat      60
ctaggtgaat tacctgtaga cgctcgtttc cctcctcgtg ttcctaaatc ttttccttt     120 aacacttctg ttgtttacaa aaagactcta tttgttgagt tcacagatca cctattcaac     180
attgctaaac cacgtcctcc ttggatgggt ctacttggcc ctactattca agctgaagta     240
tatgatactg ttgtaattac cctaaaaaac atggcttctc accctgtttc tttacatgca     300
gttggtgttt cttactggaa agctagtgag gtgctgaat acgatgatca gacttcccaa     360
cgtgaaaaag aagatgataa agttttccct ggtggttctc acacctacgt tggcaagtt     420 ttaaaagaaa acggacctat ggcttctgat ccattatgtc taacttacag ttatctatct     480
catgttgatt tggttaaaga tttgaatagt ggtctaattg gtgctctact agtatgtcgt     540
gaaggttctc ttgcaaaaga aaaaactcaa actcttcaca aattcattct tttatttgct     600
gtatttgatg aaggaaaaag ctggcacagt gaaactaaaa attctttgat gcaagatcgt     660
gatgctgcat ctgctcgcgc ttggccaaaa atgcacactg taaatggtta cgtaaataga     720
tctctacctg gtcttattgg ttgtcaccgt aaaagtgtat attggcatgt aatcggtatg     780
ggtactactc ctgaggtaca ctctatcttc ttagaaggac ataccttctt agtacgcaat     840
cacagacagg cttctcttga aatttctcca atcactttcc ttactgctca gaccttgtta     900
atggacttag acaattctt actatttgt cacatctctt ctcatcaaca tgacggtatg     960
gaggcatacg taaaggttga tagctgccca gaggaacctc aattgcgtat gaaaaacaac    1020
gaagaagcag aagattatga cgatgatcta accgattctg agatggatgt tgttcgtttc    1080
gatgatgata attctccttc tttcatccaa attagaagcg tagcaaaaaa acatccaaaa    1140
acttgggtac actacattgc tgcagaagaa gaggattggg attatgctcc tttggttctt    1200
gctccagacg atcgtagtta taatctcaa tatttgaaca cggtcctca acgcatcggt    1260 cgtaaataca aaaagttag attcatggct tacaccgatg aaactttcaa gacccgtgaa    1320
gctattcagc atgaatctgg aattctaggt cctctattat atggtgaagt tggtgatact    1380
cttctaatta tttttcaagaa ccaagctagc cgtccttaca catttatcc tcatggtatc    1440 actgatgtac gccctttgta ttctcgacgt ttacctaaag gagtaaaaca cttaaaggat    1500
ttccctatcc ttccaggtga gatttttcaaa tataaatgga ccgtaaccgt agaggatggt    1560
ccaaccaaat ctgaccctcg ctgtctaact cgttactact ctagcttcgt aaatatggaa    1620
cgtgatcttg ctagtggttt gatcggtcca ttactaatct gttacaaaga gtctgttgac    1680
caaagaggca accaaattat gagtgataaa cgtaatgtta tcctattcag tgttttcgat    1740
gaaaatcgtt cttggtatct aactgaaaat attcaacgat tctacctaa ccctgctggt    1800 gttcaactag aggatcctga attccaagct agtaatatca tgcattccat caatggatat    1860
gtattcgata gtttacaatt aagtgtttgt ttgcatgaag ttgcttactg gtatattcta    1920
tctatcggtg ctcaaactga cttcctatct gtattcttct ggttatacac ttcaaacac    1980 aaaatggtat acgaggatac cttgaccctt tttcctttca gtggtgaaac cgttttcatg    2040
agtatggaaa accctggtct ttggatccta ggttgtcaca attctgattt ccgtaatagg    2100
```

| | | |
|---|---|---|
| ggtatgactg ctttgctaaa agtctcttct tgtgataaaa acactggtga ttactatgag | 2160 |
| gatagttatg aagatatttc tgcttatttg ctatctaaaa acaatgctat tgagcctcgt | 2220 |
| tctttctctc aaaatccacc tgttttaaaa cgtcaccaac gctaa | 2265 |

<210> SEQ ID NO 11
<211> LENGTH: 63
<212> TYPE: DNA
<213> ORGANISM: Artificial Sequence
<220> FEATURE:
<223> OTHER INFORMATION: N8 B domain

<400> SEQUENCE: 11

| | |
|---|---|
| tctttctctc aaaattctcg tcatccgagt caaaatccac ctgttttaaa acgtcaccaa | 60 |
| cgc | 63 |

<210> SEQ ID NO 12
<211> LENGTH: 10
<212> TYPE: PRT
<213> ORGANISM: Artificial Sequence
<220> FEATURE:
<223> OTHER INFORMATION: GPGP-furin cleavage site

<400> SEQUENCE: 12

Gly Pro Gly Pro Arg Arg Lys Arg Ser Val
1               5                   10

<210> SEQ ID NO 13
<211> LENGTH: 2055
<212> TYPE: DNA
<213> ORGANISM: Homo sapien

<400> SEQUENCE: 13

| | |
|---|---|
| gaaataactc gtactactct tcagtcagat caagaggaaa ttgactatga tgataccata | 60 |
| tcagttgaaa tgaagaagga agattttgac atttatgatg aggatgaaaa tcagagcccc | 120 |
| cgcagctttc aaaagaaaac acgacactat tttattgctg cagtggagag gctctgggat | 180 |
| tatgggatga gtagctcccc acatgttcta agaaacaggg ctcagagtgg cagtgtccct | 240 |
| cagttcaaga agttgttttt ccaggaattt actgatggct cctttactca gcccttatac | 300 |
| cgtggagaac taaatgaaca tttgggactc ctggggccat atataagagc agaagttgaa | 360 |
| gataatatca tggtaacttt cagaaatcag gcctctcgtc cctattcctt ctattctagc | 420 |
| cttatttctt atgaggaaga tcagaggcaa ggagcagaac tagaaaaaa ctttgtcaag | 480 |
| cctaatgaaa ccaaaactta cttttggaaa gtgcaacatc atatggcacc cactaaagat | 540 |
| gagtttgact gcaaagcctg ggcttatttc tctgatgttg acctggaaaa agatgtgcac | 600 |
| tcaggcctga ttggacccct tctggtctgc cacactaaca cactgaaccc tgctcatggg | 660 |
| agacaagtga cagtacagga atttgctctg ttttttcacca tctttgatga gaccaaaagc | 720 |
| tggtacttca ctgaaaatat ggaaagaaac tgcagggctc cctgcaatat ccagatggaa | 780 |
| gatcccactt ttaagagaa ttatcgcttc catgcaatca atggctacat aatggataca | 840 |
| ctacctggct tagtaatggc tcaggatcaa aggattcgat ggtatctgct cagcatgggc | 900 |
| agcaatgaaa acatccattc tattcatttc agtggacatg tgttcactgt acgaaaaaaa | 960 |
| gaggagtata aaatggcact gtacaatctc tatccaggtg ttttgagac agtggaaatg | 1020 |
| ttaccatcca agctggaat ttggcgggtg gaatgcctta ttggcgagca tctacatgct | 1080 |
| gggatgagca cactttttct ggtgtacagc aataagtgtc agactcccct ggaatggct | 1140 |

```
tctggacaca ttagagattt tcagattaca gcttcaggac aatatggaca gtgggcccca    1200
aagctggcca gacttcatta ttccggatca atcaatgcct ggagcaccaa ggagccctt    1260 tcttggatca aggtggatct gttggcacca atgattattc acggcatcaa gacccaggt    1320 gcccgtcaga agttctccag cctctacatc tctcagttta tcatcatgta tagtcttgat    1380
gggaagaagt ggcagactta tcgaggaaat tccactggaa ccttaatggt cttctttggc    1440
aatgtggatt catctgggat aaaacacaat attttttaacc ctccaattat tgctcgatac    1500
atccgtttgc acccaactca ttatagcatt cgcagcactc ttcgcatgga gttgatgggc    1560
tgtgatttaa atagttgcag catgccattg gaatggaga gtaaagcaat atcagatgca    1620
cagattactg cttcatccta ctttaccaat atgtttgcca cctggtctcc ttcaaaagct    1680
cgacttcacc tccaagggag gagtaatgcc tggagacctc aggtaataa tccaaaagag    1740 tggctgcaag tggacttcca gaagacaatg aaagtcacag gagtaactac tcagggagta    1800
aaatctctgc ttaccagcat gtatgtgaag gagttcctca tctccagcag tcaagatggc    1860
catcagtgga ctctcttttt tcagaatggc aaagtaaagg ttttttcaggg aaatcaagac    1920 tccttcacac ctgtggtgaa ctctctagac ccaccgttac tgactcgcta ccttcgaatt    1980
cacccccaga gttgggtgca ccagattgcc ctgaggatgg aggttctggg ctgcgaggca    2040
caggacctct actaa                                                    2055
```

<210> SEQ ID NO 14
<211> LENGTH: 2055
<212> TYPE: DNA
<213> ORGANISM: Artificial Sequence
<220> FEATURE:
<223> OTHER INFORMATION: copon optimized FVIII LC

<400> SEQUENCE: 14

```
gaaattactc gcaccactct acaatctgat caagaagaga tcgattatga tgatactatt      60
agtgtagaaa tgaaaaaaga gattttgac atttacgatg aagatgaaaa ccaaagtcct     120
cgctccttcc aaaaaaaaac tagacattat ttcattgctg ctgtagagcg tttatgggat     180
tacggtatgt ctagttctcc tcacgtttta cgtaaccgtg cacaaagcgg ctctgtacct     240
caattcaaaa aagtagtatt ccaagagttc actgatggaa gtttcacaca accattgtac     300
cgcggagaac ttaatgaaca cctaggtcta ttaggtcctt acatcgagc agaagtagaa     360 gataacatta tggttacctt ccgtaaccaa gcctctcgtc cttattcctt ttacagctct     420
ctaatcagtt acgaagaaga ccagagacaa ggtgcagagc cacgtaaaaa tttcgttaaa     480
ccaaacgaaa ctaaaaccta tttctggaaa gttcagcatc acatggctcc tacaaaagat     540
gaatttgact gcaaggcttg gcttattttt tctgatgttg atcttgaaaa agatgttcat     600
tctggtctaa taggtccttt gcttgtatgt cataccaata ctctaaatcc tgctcacggt     660
cgtcaggtta ctgtacaaga gttcgctcta ttccttcacca ttttcgatga actaaaaagc     720
tggtatttca cagagaatat ggaacgtaac tgtagagctc catgtaatat tcaaatggaa     780
gatcctactt tcaaagaaaa ctatcgtttt catgccatca acggctacat catggatact     840
cttccaggtt tggtaatggc acaagatcaa agaattcgtt ggtacttgct atctatgggt     900
tctaacgaga atattcactc cattcacttt tctggacatg ttttcactgt tcgtaagaaa     960
gaagaataca aaatggcttt atataacttg tatcctggtg tatttgagac tgtagaaatg    1020
ttaccgtcta agctggaat ctggcgtgta gaatgttga ttggtgaaca cttacatgca    1080
ggtatgagta ccttgttct tgtatatagc aataagtgtc aaaccccact aggtatggcc    1140
```

| | |
|---|---|
| tccggacaca ttcgcgattt tcaaattact gcttctggcc aatatggtca gtgggcacct | 1200 |
| aaacttgctc gattacacta ttctggttct atcaacgctt ggtctacaaa agaaccattc | 1260 |
| agctggatca aagttgatct attagctcct atgattatac acggcattaa gactcaaggt | 1320 |
| gctcgtcaaa aattctcttc cctttacatc agtcagttca ttattatgta cagtcttgat | 1380 |
| ggtaaaaagt ggcaaactta ccgcggtaac tctaccggaa ctttaatggt attcttcggc | 1440 |
| aatgttgaca gctctggtat caaacataat atcttcaatc ctcctatcat tgcacgttat | 1500 |
| attagactac atccgaccca ttacagtatt cgtagtactc tacgtatgga acttatgggt | 1560 |
| tgtgatttaa attcttgttc tatgcctttg ggaatggaaa gcaaagctat ctctgatgct | 1620 |
| cagatcactg cttcctctta cttcaccaac atgtttgcta cttggtctcc tagtaaagca | 1680 |
| cgcctacact tgcagggacg atctaacgct tggcgtcctc aagttaacaa tcctaaagaa | 1740 |
| tggttgcaag ttgacttcca gaaaactatg aaagtaactg gtgtaactac tcaaggtgta | 1800 |
| aaatctctac taactagcat gtatgttaaa gaattcctta tttcctctag tcaagatggt | 1860 |
| catcaatgga ccttattctt tcagaacggt aaagtaaagg tattccaagg taatcaagat | 1920 |
| tctttcactc cagtagttaa tagtttagat cctcctttat taactcgtta tttacgtatt | 1980 |
| catcctcaat cctgggttca tcaaattgct ttgcgtatgg aggtacttgg ttgtgaagct | 2040 |
| caagacttgt attaa | 2055 |

```
<210> SEQ ID NO 15
<211> LENGTH: 4659
<212> TYPE: DNA
<213> ORGANISM: Artificial Sequence
<220> FEATURE:
<223> OTHER INFORMATION: Synthetic Sequence

<400> SEQUENCE: 15
```

| | |
|---|---|
| atgacacctc aaaatattac tgatttgtgt gcagaatacc acaacacaca aatacatacg | 60 |
| ctaaatgata agatattttc gtatacagaa tctctagctg gaaaagaga gatggctatc | 120 |
| attactttta agaatggtgc aacttttcaa gtagaagtac caggtagtca acatatagat | 180 |
| tcacaaaaaa aagcaattga aaggatgaag gataccctga ggattgcata tcttactgaa | 240 |
| gctaaagtcg aaaagttatg tgtatggaat aataaaacgc ctcatgcgat tgccgcaatt | 300 |
| agtatggcaa atggtcctgg accacgtcgt aaacgctctg ttgcaactcg tcgttactat | 360 |
| ttaggagccg ttgaactaag ttgggattat atgcaatctg atctaggtga attaccagta | 420 |
| gacgctcgtt ccctcctcg tgttcctaaa tcttttcctt ttaacacatc cgttgtttac | 480 |
| aaaaagactc tatttgttga gttcactgat cacctattca acattgctaa accacgtcct | 540 |
| ccatggatgg gcctacttgg ccctactatt caagctgaag tatatgatac tgttgtaatt | 600 |
| accctaaaga acatggcttc ccaccctgtt tctttacatg cagttggtgt ttcttactgg | 660 |
| aaagctagtg agggtgctga atacgatgat cagacttccc aacgagaaaa agaagatgat | 720 |
| aaagttttcc ctggtggctc tcacacctac gtttggcaag ttttaaaaga aaacggacct | 780 |
| atggcctccg atccattatg tctaacttac agttatctat ctcatgttga tttggttaaa | 840 |
| gatttgaata gtggtctaat tggtgctcta ttagtatgtc gtgaaggttc tcttgcaaaa | 900 |
| gaaaaaacac aaactcttca caattcatc cttttatttg ctgtatttga tgaaggaaaa | 960 |
| agctggcaca gtgaaactaa aaattctttg atgcaagatc gtgatgctgc aagcgctcgc | 1020 |
| gcttggccaa aaatgcacac tgtaaatggt tacgtaaata gatctttgcc tggtcttatt | 1080 |

```
ggctgtcacc gtaaaagcgt atattggcat gtaattggta tgggtaccac tcctgaggta    1140
cactccatct tcttagaagg acatactttc ttagtacgca atcacagaca ggcttctctt    1200
gaaatttctc caatcacttt tcttacagct cagaccttgt taatggactt aggacagttc    1260
ttactatttt gtcacatcag ctctcatcaa catgacggta tggaagcata cgtaaaggtt    1320
gatagctgcc cagaggaacc tcaattgcgt atgaaaaaca acgaagaagc tgaagattat    1380
gacgatgatc taactgattc tgagatggat gttgttcgtt tcgatgatga caattctcca    1440
agcttcatac aaattagaag cgtagcaaag aaacatccaa aaacttgggt acactacatt    1500
gctgcagaag aagaggattg ggattatgcc cctttggttc ttgctccaga cgatcgtagt    1560
tataaatctc aatatttgaa caacggtcct caacgcatcg gtcgaaaata caaaaaagtt    1620
agatttatgg cttacaccga tgaaactttc aagacccgtg aagctattca gcatgaatct    1680
ggaattcttg gtcctctatt atatggtgaa gttggtgata ctcttctaat tattttcaag    1740
aaccaagcta gccgtcctta caacatttat cctcatggca tcactgatgt acgccctttg    1800
tattctcgac gtttacctaa aggagtaaaa cacttaaagg atttccctat ccttccaggt    1860
gaaattttca aatataaatg gaccgtaacc gtagaggatg gtccaaccaa atctgaccct    1920
cgctgtctaa ctcgttacta ctctagcttc gtaaatatgg aacgtgatct tgctagtggt    1980
ttgatcggtc cattactaat ctgttacaaa gagtccgttg accaaagagg caaccaaatt    2040
atgagtgata aacgtaatgt tatactattc agtgttttcg atgaaaatcg ttcttggtat    2100
ctaactgaaa atattcaacg atttttacct aaccctgctg gtgttcaact agaggatcct    2160
gaattccaag ccagtaatat catgcatagc attaatggat atgtattcga tagtttacaa    2220
ttatccgttt gtttgcatga agttgcttac tggtatattc tatctatcgg tgctcaaact    2280
gacttcctat ctgtattctt ctctggttat accttcaaac acaaaatggt atacgaggat    2340
accttgaccc tttttccttt cagtggtgaa acagttttca tgagtatgga aacccaggc    2400 ctttggatcc taggttgtca caattctgat ttccgtaatc gcggtatgac tgctttgcta    2460
aaagtatctt cttgcgataa aaacactggt gattactatg aggatagtta tgaagatata    2520
tctgcttatt tgctatccaa aaacaatgct attgagcctc gttctttctc tcaaaatcca    2580
cctgttttaa aacgtcacca acgcgaaatt actcgcacca ctctacaatc tgatcaagaa    2640
gagatcgatt atgatgatac tattagtgta gaaatgaaaa aagaagattt tgacatttac    2700
gatgaagatg aaaaccaaag tcctcgctcc ttccaaaaaa aaactagaca ttatttcatt    2760
gctgctgtag agcgtttatg ggattacggt atgtctagtt ctcctcacgt tttacgtaac    2820
cgtgcacaaa gcggctctgt acctcaattc aaaaaagtag tattccaaga gttcactgat    2880
ggaagtttca cacaaccatt gtaccgcgga gaacttaatg aacacctagg tctattaggt    2940
ccttacatac gagcagaagt agaagataac attatggtta ccttccgtaa ccaagcctct    3000
cgtccttatt cctttacag ctctctaatc agttacgaag aagaccagag acaaggtgca    3060
gagccacgta aaaatttcgt taaaccaaac gaaactaaaa cctatttctg gaaagttcag    3120
catcacatgg ctcctacaaa agatgaattt gactgcaagg cttgggctta ttttctgat    3180 gttgatcttg aaaagatgt tcattctggt ctaataggtc ctttgcttgt atgtcatacc    3240
aatactctaa atcctgctca cggtcgtcag gttactgtac aagagttcgc tctattcttc    3300 accatttcg atgaaactaa aagctggtat tcacagaga atatggaacg taactgtaga    3360
gctccatgta atattcaaat ggaagatcct actttcaaag aaaactatcg ttttcatgcc    3420
atcaacggct acatcatgga tactcttcca ggtttggtaa tggcacaaga tcaaagaatt    3480
```

```
cgttggtact tgctatctat gggttctaac gagaatattc actccattca ctttctgga    3540 catgttttca ctgttcgtaa gaaagaagaa tacaaaatgg ctttatataa cttgtatcct    3600
ggtgtatttg agactgtaga aatgttaccg tctaaagctg gaatctggcg tgtagaatgt    3660
ttgattggtg aacacttaca tgcaggtatg agtaccttgt ttcttgtata tagcaataag    3720
tgtcaaaccc cactaggtat ggcctccgga cacattcgcg attttcaaat tactgcttct    3780
ggccaatatg tcagtgggc acctaaactt gctcgattac actattctgg ttctatcaac    3840
gcttggtcta caaaagaacc attcagctgg atcaaagttg atctattagc tcctatgatt    3900
atacacggca ttaagactca aggtgctcgt caaaaattct cttcccttta catcagtcag    3960
ttcattatta tgtacagtct tgatggtaaa aagtggcaaa cttaccgcgg taactctacc    4020
ggaactttaa tggtattctt cggcaatgtt gacagctctg gtatcaaaca taatatcttc    4080
aatcctccta tcattgcacg ttatattaga ctacatccga cccattacag tattcgtagt    4140
actctacgta tggaacttat gggttgtgat ttaaattctt gttctatgcc tttgggaatg    4200
gaaagcaaag ctatctctga tgctcagatc actgcttcct cttacttcac caacatgttt    4260
gctacttggt ctcctagtaa agcacgccta cacttgcagg gacgatctaa cgcttggcgt    4320
cctcaagtta acaatcctaa agaatggttg caagttgact tccagaaaac tatgaaagta    4380
actggtgtaa ctactcaagg tgtaaaatct ctactaacta gcatgtatgt taaagaattc    4440
cttatttcct ctagtcaaga tggtcatcaa tggaccttat tctttcagaa cggtaaagta    4500
aaggtattcc aagtaatca agattctttc actccagtag ttaatagttt agatcctcct    4560
ttattaactc gttatttacg tattcatcct caatcctggg ttcatcaaat tgctttgcgt    4620
atggaggtac ttggttgtga agctcaagac ttgtattaa                           4659
```

<210> SEQ ID NO 16
<211> LENGTH: 42
<212> TYPE: DNA
<213> ORGANISM: Artificial Sequence
<220> FEATURE:
<223> OTHER INFORMATION: B domain

<400> SEQUENCE: 16

```
tctttctctc aaaatccacc tgttttaaaa cgtcaccaac gc                       42
```

<210> SEQ ID NO 17
<211> LENGTH: 29
<212> TYPE: DNA
<213> ORGANISM: Artificial Sequence
<220> FEATURE:
<223> OTHER INFORMATION: Propep-FIX-Fw primer

<400> SEQUENCE: 17

```
gacatatgac tgtatttttg gatcatgaa                                      29
```

<210> SEQ ID NO 18
<211> LENGTH: 1377
<212> TYPE: DNA
<213> ORGANISM: Artificial Sequence
<220> FEATURE:
<223> OTHER INFORMATION: PTD-GPGP.Furin-Propeptide.FIX

<400> SEQUENCE: 18

```
atgcgtcata tcaaaatttg gtttcaaaat cgtcgcatga agtggaagaa aggtcctgga    60
ccaagacgca aacgtactgt attttttggat catgaaaatg ctaacaaaat tcttaaccgc    120
```

```
cctaaacgtt ataactctgg taaattagaa gagttcaaac agggaaattt ggagcgcgaa      180
tgcatggagg aaaaatgttc tttcgaagag gctcgtgaag ttttgagaa cactgaacga       240
accaccgaat tctggaaaca gtatgtagat ggcgaccaat gtgaatccaa cccttgtcta      300
aatggcggta gttgtaaaga cgatattaac agctacgaat gctggtgtcc ttttggtttc     360
gaaggcaaaa attgtgaact agatgtaact tgtaacatta aaaatggtcg ttgcgaacaa     420
ttctgtaaaa actccgctga caataaagta gtttgctctt gtactgaagg ttatcgtctt     480
gctgaaaatc aaaaagttg tgagcctgca gttccttccc catgtggtcg tgtaagtgtt      540
tctcagacta gcaaactaac aagagctgaa accgtattcc ctgatgttga ctatgtaaat     600
agtactgagg ctgaaacaat cttggataac attacccaaa gcactcaatc tttcaatgat    660
tttactcgtg tagttggtgg cgaagatgca aagccaggtc aattcccttg gcaagtagtt    720
cttaacggta aggttgatgc tttctgtggt ggatccatcg taaatgaaaa atggattgta    780
actgctgcac actgtgtaga aacaggtgtt aaaatcactg tagttgctgg tgaacacaac    840
attgaggaaa ctgagcatac tgaacaaaaa cgtaatgtta ttcgtatcat accacaccac    900
aactataatg ctgccattaa caaatacaat cacgatatag ccctattgga actagatgaa    960
cctctagttc ttaacagtta tgtaaccca atctgtattg ctgataaaga atacaccaat   1020
atcttcttga aattcggttc tggatatgtt agcggttggg gtcgtgtttt ccataaaggt    1080
cgatctgctt tagtacttca atacttgaga gtacctttag tagatcgtgc tacttgtcta    1140
ttatctacta aattcaccat ttacaacaac atgttctgtg caggcttcca tgaaggaggt    1200
cgtgatagtt gtcaaggtga ttctggaggt cctcacgtta ctgaggttga aggtacttgg    1260
ttttaaccg gtatcatttc ttggggtgaa gaatgtgcta tgaaaggtaa atacggcatt     1320
tatactaaag tttctcgtta cgtaaattgg attaagaaa agactaaatt aacctaa      1377
```

<210> SEQ ID NO 19
<211> LENGTH: 458
<212> TYPE: PRT
<213> ORGANISM: Artificial Sequence
<220> FEATURE:
<223> OTHER INFORMATION: PTD-GPGP.Furin-Propeptide.FIX

<400> SEQUENCE: 19

```
Met Arg His Ile Lys Ile Trp Phe Gln Asn Arg Arg Met Lys Trp Lys
1               5                   10                  15

Lys Gly Pro Gly Pro Arg Arg Lys Arg Thr Val Phe Leu Asp His Glu
            20                  25                  30

Asn Ala Asn Lys Ile Leu Asn Arg Pro Lys Arg Tyr Asn Ser Gly Lys
        35                  40                  45

Leu Glu Glu Phe Lys Gln Gly Asn Leu Glu Arg Glu Cys Met Glu Glu
    50                  55                  60

Lys Cys Ser Phe Glu Glu Ala Arg Glu Val Phe Glu Asn Thr Glu Arg
65                  70                  75                  80

Thr Thr Glu Phe Trp Lys Gln Tyr Val Asp Gly Asp Gln Cys Glu Ser
                85                  90                  95

Asn Pro Cys Leu Asn Gly Gly Ser Cys Lys Asp Asp Ile Asn Ser Tyr
            100                 105                 110

Glu Cys Trp Cys Pro Phe Gly Phe Glu Gly Lys Asn Cys Glu Leu Asp
        115                 120                 125

Val Thr Cys Asn Ile Lys Asn Gly Arg Cys Glu Gln Phe Cys Lys Asn
    130                 135                 140
```

Ser Ala Asp Asn Lys Val Val Cys Ser Cys Thr Glu Gly Tyr Arg Leu
145                 150                 155                 160

Ala Glu Asn Gln Lys Ser Cys Glu Pro Ala Val Pro Phe Pro Cys Gly
            165                 170                 175

Arg Val Ser Val Ser Gln Thr Ser Lys Leu Thr Arg Ala Glu Thr Val
        180                 185                 190

Phe Pro Asp Val Asp Tyr Val Asn Ser Thr Glu Ala Glu Thr Ile Leu
    195                 200                 205

Asp Asn Ile Thr Gln Ser Thr Gln Ser Phe Asn Asp Phe Thr Arg Val
210                 215                 220

Val Gly Glu Asp Ala Lys Pro Gly Gln Phe Pro Trp Gln Val Val
225                 230                 235                 240

Leu Asn Gly Lys Val Asp Ala Phe Cys Gly Gly Ser Ile Val Asn Glu
            245                 250                 255

Lys Trp Ile Val Thr Ala Ala His Cys Val Glu Thr Gly Val Lys Ile
        260                 265                 270

Thr Val Val Ala Gly Glu His Asn Ile Glu Glu Thr Glu His Thr Glu
    275                 280                 285

Gln Lys Arg Asn Val Ile Arg Ile Ile Pro His His Asn Tyr Asn Ala
290                 295                 300

Ala Ile Asn Lys Tyr Asn His Asp Ile Ala Leu Leu Glu Leu Asp Glu
305                 310                 315                 320

Pro Leu Val Leu Asn Ser Tyr Val Thr Pro Ile Cys Ile Ala Asp Lys
            325                 330                 335

Glu Tyr Thr Asn Ile Phe Leu Lys Phe Gly Ser Gly Tyr Val Ser Gly
        340                 345                 350

Trp Gly Arg Val Phe His Lys Gly Arg Ser Ala Leu Val Leu Gln Tyr
    355                 360                 365

Leu Arg Val Pro Leu Val Asp Arg Ala Thr Cys Leu Leu Ser Thr Lys
370                 375                 380

Phe Thr Ile Tyr Asn Asn Met Phe Cys Ala Gly Phe His Glu Gly Gly
385                 390                 395                 400

Arg Asp Ser Cys Gln Gly Asp Ser Gly Gly Pro His Val Thr Glu Val
            405                 410                 415

Glu Gly Thr Trp Phe Leu Thr Gly Ile Ile Ser Trp Gly Glu Glu Cys
        420                 425                 430

Ala Met Lys Gly Lys Tyr Gly Ile Tyr Thr Lys Val Ser Arg Tyr Val
    435                 440                 445

Asn Trp Ile Lys Glu Lys Thr Lys Leu Thr
450                 455

<210> SEQ ID NO 20
<211> LENGTH: 29
<212> TYPE: DNA
<213> ORGANISM: Artificial Sequence
<220> FEATURE:
<223> OTHER INFORMATION: Propep-FIX-Rv primer

<400> SEQUENCE: 20
gatctagatt aggttaattt agtcttttc                                29

<210> SEQ ID NO 21
<211> LENGTH: 1305
<212> TYPE: DNA
<213> ORGANISM: Artificial Sequence
<220> FEATURE:
<223> OTHER INFORMATION: Propepeptide.FIX.KLW

<400> SEQUENCE: 21

```
atgactgtat ttttggatca tgaaaatgct aacaaaattc ttaaccgccc taaacgttat      60
aactctggta aattagaaga gttcaaacag ggaaatttgg agcgcgaatg catggaggaa     120
aaatgttctt cgaagaggc tcgtgaagtt tttgagaaca ctgaacgaac caccgaattc     180
tggaaacagt atgtagatgg cgaccaatgt gaatccaacc cttgtctaaa tggcggtagt     240
tgtaaagacg atattaacag ctacgaatgc tggtgtcctt ttggtttcga aggcaaaaat     300
tgtgaactag atgtaacttg taacattaaa aatggtcgtt gcgaacaatt ctgtaaaaac     360
tccgctgaca taaagtagt ttgctcttgt actgaaggtt atcgtcttgc tgaaaatcaa     420
aaaagttgtg agcctgcagt tccttttccca tgtggtcgtg taagtgtttc tcagactagc     480
aaactaacaa gagctgaaac cgtattccct gatgttgact atgtaaatag tactgaggct     540
gaaacaatct tggataacat acccaaagc actcaatctt tcaatgattt tactcgtgta     600
gttggtggcg aagatgcaaa gccaggtcaa ttcccttggc aagtagttct taacggtaag     660
gttgatgctt tctgtggtgg atccatcgta aatgaaaaat ggattgtaac tgctgcacac     720
tgtgtagaaa caggtgttaa atcactgta gttgctggtg aacacaacat tgaggaaact     780
gagcatactg aacaaaaacg taatgttatt cgtatcatac cacaccacaa ctataatgct     840
gccattaaca atacaatca cgatatagcc ctattggaac tagatgaacc tctagttctt     900
aacagttatg taaccccaat ctgtattgct gataaagaat acaccaatat cttcttgaaa     960
ttcggttctg gatatgttag cggttggggt cgtgttttcc ataaaggtcg atctgctta    1020
gtacttcaat acttgagagt acctttagta gatcgtgcta cttgtctatt atctactaaa    1080
ttcaccattt acaacaacat gttctgtgca ggcttccatg aaggaggtcg tgatagttgt    1140
caaggtgatt ctggaggtcc tcacgttact gaggttgaag tacttggtt tttaaccggt    1200
atcatttctt ggggtgaaga atgtgctatg aaaggtaaat acggcattta tactaaagtt    1260
tctcgttacg taaattggat taagaaaag actaaattaa cctaa                    1305
```

<210> SEQ ID NO 22
<211> LENGTH: 434
<212> TYPE: PRT
<213> ORGANISM: Artificial Sequence
<220> FEATURE:
<223> OTHER INFORMATION: Propepeptide.FIX.KLW

<400> SEQUENCE: 22

```
Met Thr Val Phe Leu Asp His Glu Asn Ala Asn Lys Ile Leu Asn Arg
1               5                   10                  15

Pro Lys Arg Tyr Asn Ser Gly Lys Leu Glu Glu Phe Lys Gln Gly Asn
            20                  25                  30

Leu Glu Arg Glu Cys Met Glu Glu Lys Cys Ser Phe Glu Glu Ala Arg
        35                  40                  45

Glu Val Phe Glu Asn Thr Glu Arg Thr Thr Glu Phe Trp Lys Gln Tyr
    50                  55                  60

Val Asp Gly Asp Gln Cys Glu Ser Asn Pro Cys Leu Asn Gly Gly Ser
65                  70                  75                  80

Cys Lys Asp Asp Ile Asn Ser Tyr Glu Cys Trp Cys Pro Phe Gly Phe
                85                  90                  95

Glu Gly Lys Asn Cys Glu Leu Asp Val Thr Cys Asn Ile Lys Asn Gly
            100                 105                 110

Arg Cys Glu Gln Phe Cys Lys Asn Ser Ala Asp Asn Lys Val Val Cys
```

-continued

```
            115                 120                 125
Ser Cys Thr Glu Gly Tyr Arg Leu Ala Glu Asn Gln Lys Ser Cys Glu
    130                 135                 140

Pro Ala Val Pro Phe Pro Cys Gly Arg Val Ser Val Ser Gln Thr Ser
145                 150                 155                 160

Lys Leu Thr Arg Ala Glu Thr Val Phe Pro Asp Val Asp Tyr Val Asn
                165                 170                 175

Ser Thr Glu Ala Glu Thr Ile Leu Asp Asn Ile Thr Gln Ser Thr Gln
                180                 185                 190

Ser Phe Asn Asp Phe Thr Arg Val Val Gly Gly Glu Asp Ala Lys Pro
            195                 200                 205

Gly Gln Phe Pro Trp Gln Val Val Leu Asn Gly Lys Val Asp Ala Phe
        210                 215                 220

Cys Gly Gly Ser Ile Val Asn Glu Lys Trp Ile Val Thr Ala Ala His
225                 230                 235                 240

Cys Val Glu Thr Gly Val Lys Ile Thr Val Val Ala Gly Glu His Asn
                245                 250                 255

Ile Glu Glu Thr Glu His Thr Glu Gln Lys Arg Asn Val Ile Arg Ile
                260                 265                 270

Ile Pro His His Asn Tyr Asn Ala Ala Ile Asn Lys Tyr Asn His Asp
            275                 280                 285

Ile Ala Leu Leu Glu Leu Asp Glu Pro Leu Val Leu Asn Ser Tyr Val
        290                 295                 300

Thr Pro Ile Cys Ile Ala Asp Lys Glu Tyr Thr Asn Ile Phe Leu Lys
305                 310                 315                 320

Phe Gly Ser Gly Tyr Val Ser Gly Trp Gly Arg Val Phe His Lys Gly
                325                 330                 335

Arg Ser Ala Leu Val Leu Gln Tyr Leu Arg Val Pro Leu Val Asp Arg
            340                 345                 350

Ala Thr Cys Leu Leu Ser Thr Lys Phe Thr Ile Tyr Asn Asn Met Phe
        355                 360                 365

Cys Ala Gly Phe His Glu Gly Gly Arg Asp Ser Cys Gln Gly Asp Ser
    370                 375                 380

Gly Gly Pro His Val Thr Glu Val Glu Gly Thr Trp Phe Leu Thr Gly
385                 390                 395                 400

Ile Ile Ser Trp Gly Glu Glu Cys Ala Met Lys Gly Lys Tyr Gly Ile
                405                 410                 415

Tyr Thr Lys Val Ser Arg Tyr Val Asn Trp Ile Lys Glu Lys Thr Lys
            420                 425                 430

Leu Thr
```

COMPOSITIONS AND METHODS FOR SUPPRESSION OF INHIBITOR FORMATION AGAINST COAGULATION FACTORS IN HEMOPHILIA PATIENTS

CROSS REFERENCE TO RELATED APPLICATIONS

This application is a Continuation Application of U.S. patent application Ser. No. 15/037,045, filed 16 May 2016, which is a continuation-in-part of International Application No. PCT/US14/65994 filed Nov. 17, 2015 which claims priority to U.S. Provisional Application Nos. 61/905,069 and 61/905,071, both filed Nov. 15, 2013, the entire disclosures of each of the aforementioned applications being incorporated herein by reference as though set forth in full.

This invention was made with government support under grant numbers R01HL 107904 and R01 HL109442 awarded by the National Institutes of Health. The government has certain rights in the invention.

FIELD OF THE INVENTION

The present invention relates to the fields of recombinant plants and the treatment of disorders for which induction of oral tolerance to therapeutically delivered antigens is desired. More specifically, the invention provides compositions and methods for inducing oral tolerance to Factor VIII, Factor IX and other coagulation factors thereby improving therapeutic outcomes.

BACKGROUND OF THE INVENTION

Several publications and patent documents are cited throughout the specification in order to describe the state of the art to which this invention pertains. Each of these citations is incorporated herein by reference as though set forth in full.

Hemophilia is the X-linked bleeding disorder caused by mutations in coagulation factor IX (FIX, hemophilia B) or its co-factor, factor VIII (FVIII, hemophilia A). Since the serine protease FIX has very low activity in the absence of FVIII, mutations in either protein can cause the coagulation defect. Hemophilia A disease affects 1 in 7,500 male births worldwide, whereas hemophilia B affects 1 in 30,000.[1-3] Hence, the majority of hemophilia patients are FVIII-deficient. Current standard treatment is based on intravenous (IV) infusion of plasma-derived or recombinant factor concentrate. A major complication of this therapy is the formation of inhibitory antibodies ("inhibitors"), which occurs in 20-30% of patients with severe hemophilia A (as defined by <1% coagulation activity) and in ~5% of severe hemophilia B patients.[1,4-6] Inhibitors seriously complicate treatment and increase morbidity and mortality of this disease. Increased factor doses may be able to restore hemostasis in patients with low-titer inhibitors (<5 Bethesda Units, BU), while bypass factors are required to treat a bleed in the presence of high-titer inhibitors. However, these treatments are expensive and have to be carefully dosed. Clinical protocols for reversal of the antibody response via immune tolerance induction (ITI) consist of frequent high-dose factor administrations for prolonged periods (months to >1 year), are very expensive (>$1,000,000), and ~30% of FVIII inhibitor patients fail to respond.[4]

While the overall incidence of inhibitors is lower in hemophilia B (1-4%), 9-23% of patients with severe disease form inhibitors. These are typically high-titer and are almost exclusively confined to subjects with gene deletions or early stop codons. ITI protocols are less effective for treatment of inhibitors to coagulation factor IX (F.IX). Importantly, studies found that up to 50% of patients with F.IX inhibitors may experience potentially life-threatening anaphylactic reactions to F.IX, which also preclude the subject from home treatment and severely hinder ITI protocols.

SUMMARY OF THE INVENTION

In accordance with the present invention, a composition comprising lyophilized plant material is provided. In a preferred embodiment, the material comprises a coagulation protein, or immunogenic fragments thereof, produced in chloroplasts within said plant wherein the coagulation protein or immunogenic fragment retains immunogenicity in lyophilized form, which upon oral administration to a mammal in need thereof is effective to produce oral tolerance to the protein. The coagulation factors may include for example, F.II, F.III, F.IV, F.V, F.VI, F.VII, F.VIII, F.IX, F.X, F.XI, F.XII, and/or F.XIII, or a polypeptides having at least 90 percent identity therewith. In a particularly preferred embodiment, the plant material comprises leaves containing transgenic chloroplasts, and the therapeutic protein is a fusion protein comprising Factor VIII and/or at least one immunogenic domain fragment thereof, and cholera non toxic B subunit (CTB), wherein the material is effective to induce tolerance to said protein or fragment in said mammal upon oral administration. The at least one immunogenic domain fragment is a domain of FVIII selected from the group consisting of A1, A2, A3, B, C1, C2 or heavy chain (HC) fragments. In a particularly preferred embodiment, the therapeutic protein is at least one immunological fragment of FVIII consisting of a C2 domain and/or a HC domain, or an immunological fragment of FIX each fused to cholera non toxic B subunit (CTB), wherein the orally administered fragments induce tolerance to said coagulation protein by suppressing inhibitory antibody formation. Also preferred are compositions effective to induce expression of TGF-β producing CD4$^+$CD25$^-$LAP$^+$ regulatory T cells in spleen, MLN, and Peyer's patches. A variety of plants may be employed in accordance with the present invention. Such plants include without limitation, lettuce, carrots, cauliflower, cabbage, low-nicotine tobacco, spinach, kale, and cilantro.

In certain embodiments one, two, three, four, five or six domains of FVIII are administered together. Exemplary compositions and methods include those where a C2-CTB and an HC-CTB fusion protein are administered together. The present inventors have discovered that the compositions disclosed herein are effective to reduce inhibitor formation against FVIII in hemophilia A subjects or FIX in hemophilia B subjects. Thus, the invention also provides a method for the treatment of Hemophilia A or Hemophilia B in a subject in need thereof comprising administration of an effective amount of the compositions described above to a subject in need thereof, said composition being effective to suppress formation of inhibitors of FVIII or FIX in said subject and induce expression of TGF-β producing CD4$^+$CD25$^-$LAP$^+$ regulatory T cells in spleen, MLN, and Peyer's patches.

The present invention also provided codon optimized FVIII and FIX nucleic acid sequences which exhibit increased expression in plant chloroplasts when compared to expression levels observed in plants expressing the native human nucleic acid sequences.

Also provided is a method of treating a subject having a genetic disease and at risk for development of an anaphylactic reaction in response to protein replacement therapy, said method comprising administering an effective amount of a composition comprising a lyophilized tolerance factor and a plant remnant, the tolerance factor being a protein or immunological fragment thereof, wherein loss or mutation of said protein is causative of said disease. In certain embodiments, the tolerance factor is coagulation factor, such as FVIII or FXI, an acid alpha-glucosidase, alpha-galactosidase A, Glucocerebrosidase, alpha-L-iduronidase, or sphingomyelinase, or variants having at least a 90 percent identity therewith. In a preferred embodiment the therapeutic tolerance factor is conjugated to cholera toxin B. Diseases to be treated using the compositions of the invention, include, for example, hemophilia A, hemophilia B, Pompe disease, Fabry disease, Gaucher disease, Mucopolysaccharidosis I, or Niemann-Pick disease. The compositions and methods of the invention can also be used to reverse or reduce preexisting undesirable antibody inhibitor titers, thereby improving therapeutic outcomes.

BRIEF DESCRIPTION OF THE DRAWINGS

FIGS. 1A-1B. Chloroplast transformation vectors and integration of transgenes into the chloroplast genome. (FIG. 1A) Tobacco chloroplast expression vectors. Homologous chloroplast genome flanking sequences comprising of 16S 3,' trnI, trnA gene sequences; Prrn, ribosomal RNA operon promoter with GGAGG ribosome binding site; aadA, aminoglycoside 3'-adenylytransferase gene to confer spectinomycin resistance; 5' UTR, promoter and 5' UTR of tobacco psbA gene; 3' UTR, 3' UTR of tobacco psbA gene; CTB, cholera toxin B subunit. In both vectors a Gly Pro Gly Pro (GPGP) hinge and furin cleavage site (RRKR) is included between CTB and the FVIII domain sequence. WT, untransformed wild type. Nt, *Nicotiana tabacum*. The restriction site of AflIII and the sizes of Southern blot fragments are indicated. (FIG. 1B) Southern blot, tobacco CTB-HC, WT (untransformed), 1-3 transplastomic lines. Tobacco total genomic DNA was digested with AflIII and probed with 0.81 kb trnI/trnA flanking region fragment. (FIG. 1C) Southern blot, tobacco CTB-C2, WT (untransformed wild type), 1-4 transplastomic lines.

FIGS. 2A-2F. Characterization of CTB-HC and CTB-C2 expression in tobacco chloroplasts. (FIG. 2A) Detection of heavy chain fusion protein probed with the CTB antibody. CTB standard: 6.25 ng, 12.5 ng, 25 ng. WT: untransformed wild type. 1-4, transplastomic lines. Five μg total protein of homogenate fraction per lane was loaded. (FIG. 2B) Detection of heavy chain probed with the A2 antibody. CTB: 25 ng. 1-4, transplastomic lines. Five μg total protein of homogenate fraction per lane was loaded. (FIG. 2C) Detection of C2 fusion protein probed with the CTB antibody. CTB standard: 5 ng, 10 ng, 20 ng. S: supernatant fraction; H: homogenate fraction. Two μg total protein of supernatant or homogenate fraction per lane was loaded. (FIG. 2D) Quantitation of CTB-HC and CTB-C2 expression in tobacco chloroplasts. Proteins were extracted from mature leaves at different time points on the same day. TLP, total leaf protein. (FIG. 2E) Ganglioside GM1 ELISA binding assay. CTB standard (0.1 ng); tobacco CTB-HC (5 μg); tobacco CTB-C2 (1 μg); untransformed tobacco wild type (5 μg); BSA, bovine serum albumin (5 μg). (FIG. 2F) Blue Native Gel Electrophoresis and western blot analysis to evaluate pentamer assembly. Pentamer sizes: CTB: 57.5 kDa; CTB-C2: 155 kDa; CTB-HC: 490 kDa. Samples loaded: CTB standard, 100 ng; WT, 40 μg; CTB-HC, 40 μg; CTB-C2, 10 μg.

FIGS. 3A-3G. Suppression of inhibitor formation against FVIII in hemophilia A C57BL6/129 mice by oral administration of a 1:1 mixture of bioencapsulated CTB-C2 and CTB-HC FVIII antigens. (FIG. 3A) Time line of oral antigen administration and intravenous treatment with BDD-FVIII. Number in circle indicates time point for tail bleed. (FIG. 3B) Inhibitor titers (in BU/ml) after four weekly IV injections of FVIII in non-fed animals ("no plant") or mice fed with WT or FVIII containing plant material. IgG1 (FIG. 3C), IgG2a (FIG. 3D), and IgG2b (FIG. 3E) titers against FVIII for the same experimental groups. Data in FIG. 3B-3E are shown for individual mice and as averages±SEM. (FIG. 3F) Following the blood draw, mice were sacrificed and spleens collected. Splenocyte cultures for individual mice (n=3 to 5 per group) were stimulated in vitro with 10 μg/ml of BDD-FVIII for 48 hours. Subsequently, cells were harvested and subjected to quantitative RT-PCR analysis. "Fold increase" is change in RNA transcripts of FVIII versus mock-stimulated cultures. The dotted horizontal line indicates the minimally required increase of 2.5 fold for a statistically significant difference. (FIG. 3G) Spenocytes derived from the same experimental mice were subjected to ELISPOT analysis for frequency of IL-10 secreting cell population. All data are shown for individual mice and as averages±SEM. Unpaired two-tailed Student's t-tests were used to calculate p-values (*** $p<0.01$).

FIGS. 4A-4E. Suppression of inhibitor formation against FVIII in hemophilia A BALB/c mice by oral administration of a 1:1 mixture of bioencapsulated CTB-C2 and CTB-HC FVIII antigens. (FIG. 4A) Feeding and FVIII treatment schedule. Number in circle indicates time-point for tail bleed. (FIG. 4B) Inhibitor titers (in BU/ml) after four weekly IV injections of BDD-FVIII in "No plant", "WT plant", and "FVIII plant" fed groups. IgG1 (FIG. 4C), IgG2a (FIG. 4D), IgG2b (FIG. 4E) titers against FVIII for the same experimental groups. All data are shown for individual mice and as averages±SEM. Unpaired two-tailed Student's t-tests were used to calculate p-values (* $p<0.05$, ** $p<0.01$).

FIGS. 5A-5F. Long-term control and reversal of inhibitor formation in hemophilia A BALB/c mice. (FIG. 5A) Feeding (HC and C2 material) and FVIII administration schedule for prevention of inhibitor formation. Numbers in circles indicate time-points for blood collections. Inhibitor titers in BU/ml (FIG. 5B) and IgG1 titers against FVIII (FIG. 5C) at weeks 8, 12, and 21 of the experiment for FVIII fed mice (n=5, back square symbols) are compared to control mice (which were fed with WT plant material, n=7, gray diamonds). Statistically significant differences between these groups for specific time points are indicated (* $p<0.05$,  $p<0.01$, and * $p<0.001$, as calculated by unpaired two-tailed Student's t-test; data are averages±SEM). A third group of mice (n=7) was also fed with FVIII material, and FVIII was administered IV once/week starting one month after initiation of the oral tolerance regimen. However, FVIII feeding and treatment was continued for the remaining duration of the experiment (i.e., 20 weeks of FVIII feeding; these mice are labeled as "FVIII continuously fed" and graphed with black triangle symbols and dotted line in FIGS. 5B and 5C; data are averages±SEM). (FIG. 5D) FVIII administration and feeding schedule for reversal of inhibitor formation. Inhibitor formation was induced by repeated weekly IV injections of FVIII as indicated. Mice were divided into 2 groups with similar average inhibitor titers. Control mice (n=5) did not receive any further treatment. The second group ("FVIII fed", n=4) was fed with FVIII plant material twice per week for the following three months. Inhibitor titers in BU/ml (FIG. 5E) and IgG1 titers against FVIII (FIG. 5F) are graphed for weeks 5, 9, 13, and 17 of the experiment as explained above.

Figure 5A:
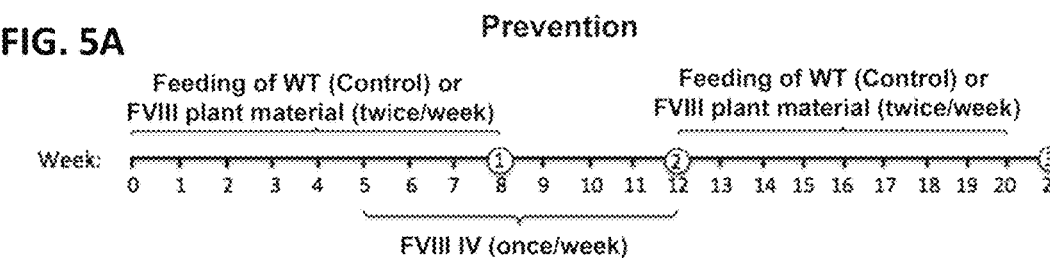
Figure 6A:
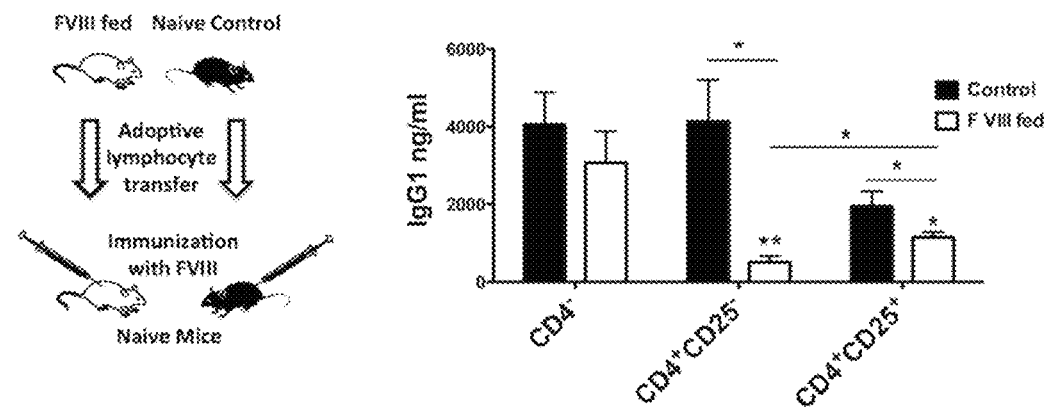
Figure 6B:
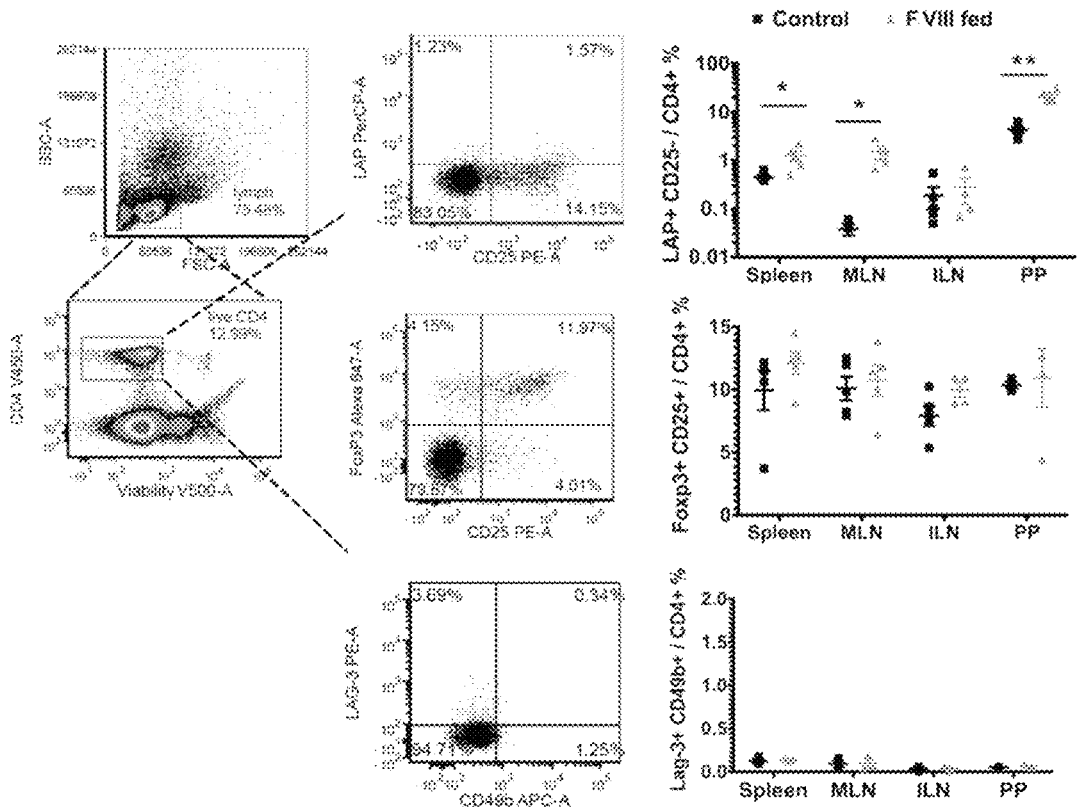

FIGS. 6A-6B. Active suppression of antibody formation against FVIII by induction of regulatory T cells. (FIG. 6A) Adoptive transfer experiments. CD4⁻, CD4⁺CD25⁻, and CD4⁺CD25⁺ cells were purified via magnetic sorting from spleens and mesenteric lymph nodes (MLN) of FVIII fed mice (n=3) at time point 3 indicated in FIG. 5A and pooled (with a final ratio of approximately 30% spleen and 70% MLN-derived CD4⁺ T cells). Cells ($10^6$ per mouse) were adoptively transferred into naïve BALB/c mice via tail vein injection. Control cells were from unchallenged naïve mice of the same strain. Twenty-four hours later, all recipient mice (n=5 per group) were challenged with 1 IU FVIII in adjuvant via subcutaneous injection. IgG titers against FVIII were determined 3 weeks later. All data are shown as averages±SEM; * p<0.05, ** p<0.01. (FIG. 6B) Frequencies of Treg subsets in FVIII fed and control hemophilia A BALB/c mice. Cells derived from spleens, mesenteric lymph nodes (MLN), inguinal lymph nodes (ILN), and Peyer's patches (PP) were isolated from mice that had either been fed with FVIII (HC+C2, "FVIII fed") or WT plant material ("control") followed by IV treatment with FVIII ("FVIII fed"). Stained cells were first gated for live CD4⁺ cells (positive CD4-eFluor 450 and negative viability dye eFluor 506 staining). The frequencies of CD4⁺CD25⁻LAP⁺ cells, CD4⁺CD25⁺Foxp3⁺ cells, and Tr1 cells (CD4⁺LAG-3⁺CD49b⁺) were calculated using flow cytometric analysis. Data for individual animals as well as averages±SEM are shown (n=3-5/group). Unpaired two-tailed Student's t-tests were used to calculate p values for all panels.

FIGS. 7A-7D. Delivery of FVIII antigen to the GALT and into circulation. (FIG. 7A-7D) Immunostains (original magnification 200×) of ileum cryo-sections from unfed (FIG. 7A, negative control) or CTB-C2 fed lamina propria (FIG. 7B) and Peyer's patch (FIG. 7C) from BALB/c hemophilia A mice. Stains are for C2 domain of FVIII (green), CD11c (red), and nuclei (DAPI; blue). (FIG. 7D) Human FVIII antigen levels were measured in plasma or liver protein extract of the CTB-HC fed C57BL6/129 and BALB/c hemophilia A mice and WT fed control mice of the same strain using HC-specific ELISA. All data are shown for individual mice and as averages±SEM.

Figure 8A:
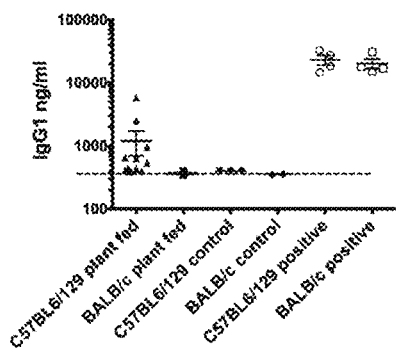
Figure 8B:
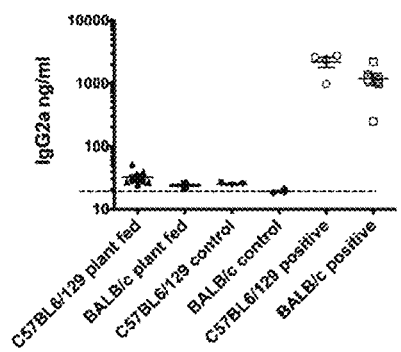
Figure 8C:
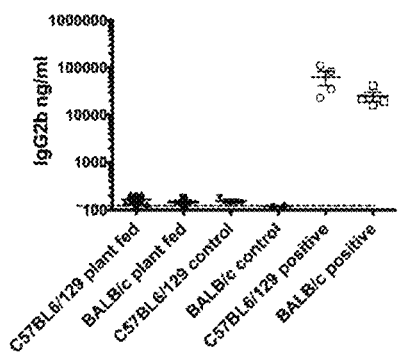

FIGS. 8A-8C. Antibody responses against CTB protein in hemophilia A mice fed with FVIII chloroplast transgenic plant material. IgG1 (FIG. 8A), IgG2a (FIG. 8B), and IgG2b (FIG. 8C) serum titers against CTB following 8 weeks of feeding with a mixture of CTB-HC and CTB-C2 transgenic tobacco material. Sera from mice of the same strain two weeks after challenging with g CTB in adjuvant served as positive controls. Unchallenged naïve mice of the same strain served as negative controls. The dotted horizontal line indicates the background of the assay (average readings for negative controls). All data are shown for individual mice and as averages ±SEM.

FIGS. 9A-9G. Generation and characterization of CTB-C2 transplastomic lettuce plants. (FIG. 9A) Lettuce CTB-C2 expression vector and a portion of native chloroplast genome. 16S trnI and trnA 23S, lettuce homologous chloroplast genome flanking sequences comprising of 16S 3' (or 23 5') end sequences and complete trnI, trnA genes; Prrn, ribosomal RNA operon promoter with GGAGG ribosome binding site; aadA, aminoglycoside 3'-adenylytransferase gene for spectinomycin resistance; 5' UTR, promoter and 5' UTR of psbA gene from lettuce; 3' UTR, 3' UTR of psbA gene from lettuce; CTB, cholera toxin B subunit. A Gly Pro Gly Pro (GPGP) hinge and furin cleavage site (RRKR) is included between CTB and the C2 sequence. WT, wild type. The restriction site of AflIII and the sizes of Southern blot positive bands are indicated. (FIG. 9B) Southern blot. WT (untransformed wild type), 1-5: transplastomic lines, lettuce genomic DNA was digested with AflIII and probed with 1.12-kb lettuce flanking region. The 7.4-kb positive band contains the CTB-C2 insertion fragment in the transplastomic lines. The absence of WT fragment (4.8-kb) in transplastomic lines 1 and 4 clearly demonstrate homoplasmy. (FIG. 9C) Western blot. Probe, anti-CTB pAb. CTB standard: 5 ng, 10 ng, 20 ng. S: supernatant fraction; H: homogenate fraction. Molecular weight of CTB-C2: 31 kDa. CTB: 12 kDa. 2.5 µg total protein of supernatant or homogenate fraction per lane was loaded. (FIG. 9D) Ganglioside GM1 ELISA binding assay. CTB standard (0.1 ng); CTB-C2 (1 µg); untransformed lettuce wild type (1 µg); BSA, bovine serum albumin (5 µg). (FIG. 9E) CTB-C2 expression levels (average ±standard deviation) in µg/g of fresh and lyophilized leaves. Lyophilized leaf materials from T0 plants: 2004±136; Fresh: 94±6. (FIG. 9F) Comparison of protein concentrations between the lyophilized leaf and fresh leaf samples. Equal amount of lyophilized or fresh leaf material was used for this analysis. 1, undiluted CTB-C2 extract (60 µg leaf powder); 1:10, 10 times dilution (6 µg leaf powder); 1:20, 20 times dilution (3 µg leaf powder). WT, wild type lettuce. CTB standard: 7.5 ng and 15 ng per lane loaded for quantitation. (FIG. 9G) Preparation of capsules: lyophilized and powdered lettuce leaves expressing CTB-C2 fusion protein for use as oral antigen.

Figure 10A:
Figure 10B:
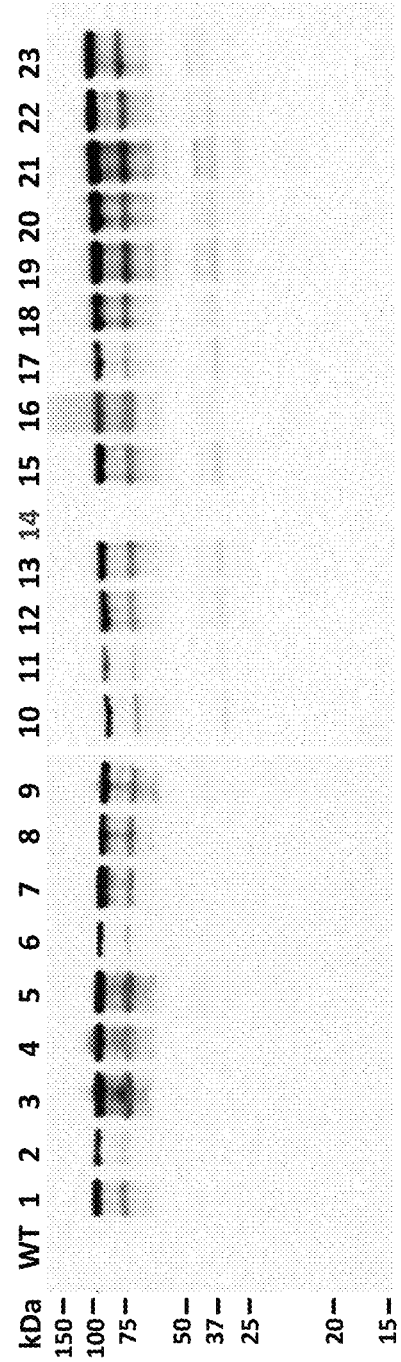

FIGS. 10A-10B. Screening for CTB-HC lettuce plants (T1) (FIG. 10A) by western blot analysis (FIG. 10B). Probe: anti-CTB; CTB-HC=97.7 kDa. All individual plants except plant #14 showed expression of CTB-HC fusion protein.

Figure 11A:
Figure 11B:
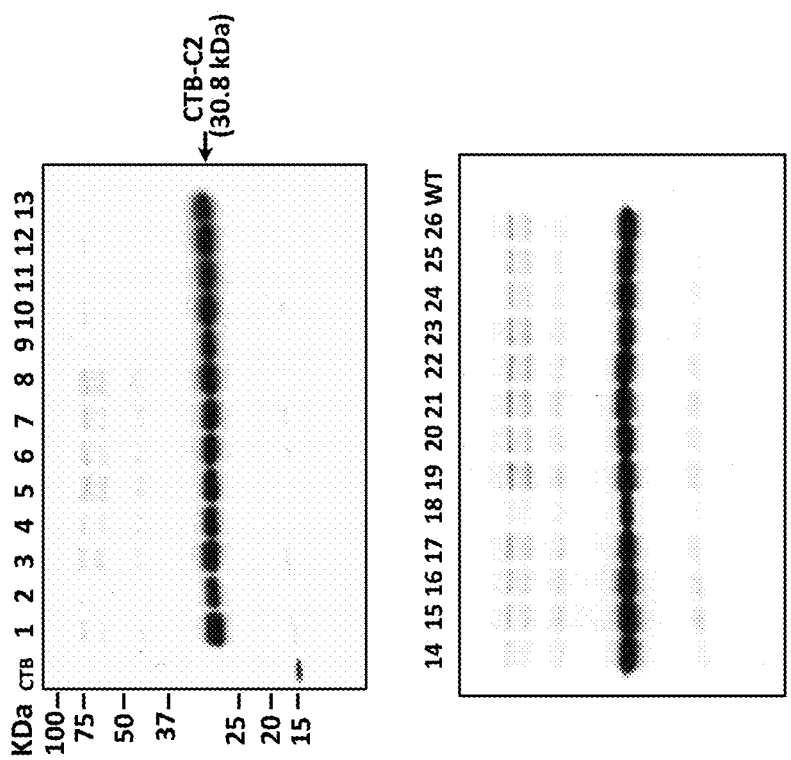

FIG. 11A-11B. Screening for CTB-C2 lettuce plants (T1) (FIG. 11A) by western blot analysis (FIG. 11B). All individual plants showed expression of CTB-HC fusion protein.

Figure 12A:
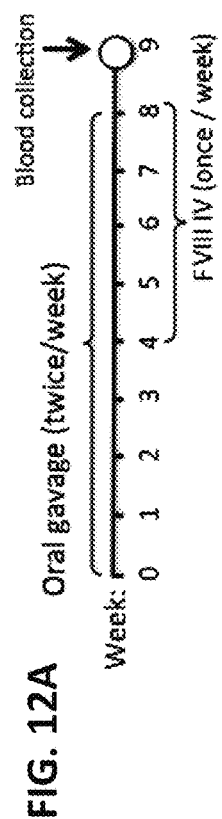
Figure 12B:
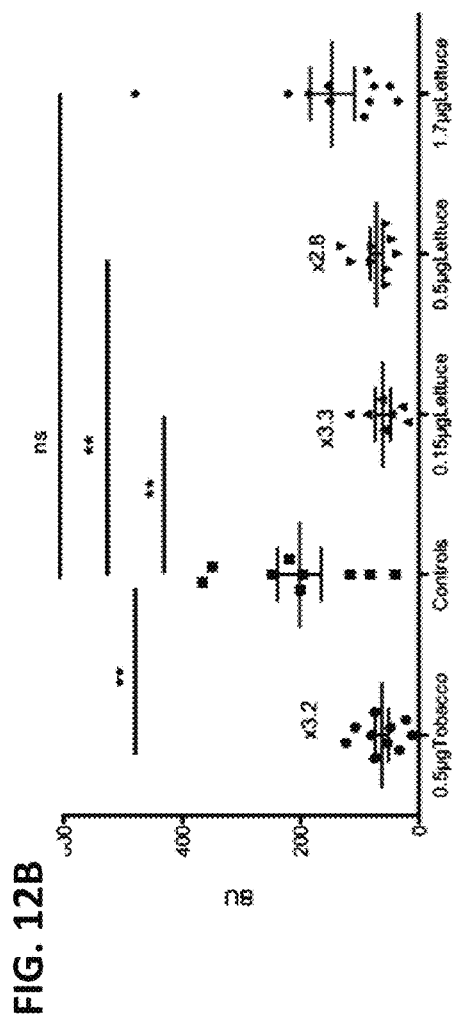
Figure 12C:
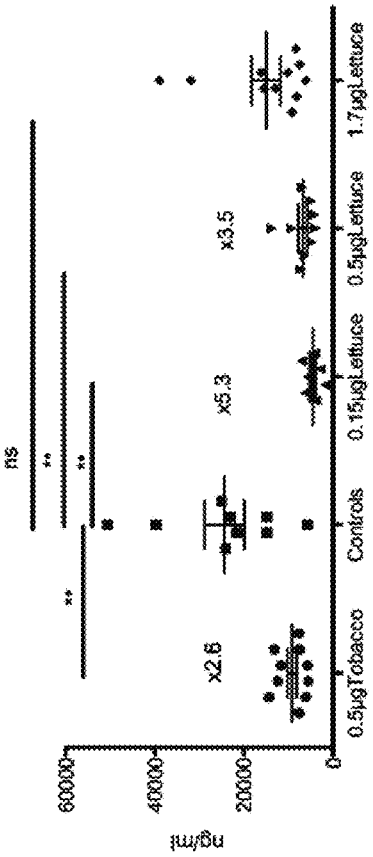

FIGS. 12A-12C. Tolerance induction in dose response studies with lyophilized CTB-C2 and CTB-HC mixtures with doses ranging from 0.15 µg/mouse to 1.7 µg/mouse. (FIG. 12A) Experimental time line. (FIG. 12B-12C) Antibody formation against FVIII. (FIG. 12B) Inhibitor titers (in BU per milliliters) after four weekly IV injections of BDD-FVIII in all dose escalation groups. (FIG. 12C) IgG1 titers in ng/ml.

FIGS. 13A-13D. Reversal of inhibitors against FVIII. Hemophilia A mice that developed inhibitors after IV treatment with recombinant FVIII received no further treatment (controls) or oral administration of lyophilized lettuce CTB-HC/CTB-C2 (0.5 µg each). (FIG. 13A) Inhibitor titers in control mice. (FIG. 13B) IgG1 anti-FVIII titers in control mice. (FIG. 13C) Inhibitor titers in lettuce fed mice. (FIG. 13D) IgG1 anti-FVIII titers in lettuce fed mice.

FIGS. 14A-14C. Suppression of inhibitor formation in hemophilia B dogs by oral delivery of lyophilized lettuce material containing CTB-FIX. Oral delivery was twice per week for weeks 0-13. Control dog S 13 did not receive lettuce. All dogs were injected IV with recombinant human FIX once per week during weeks 4-11, as indicated by the arrows. (FIG. 14A) IgG2 formation against FIX (in ng/ml). (FIG. 14B) IgG1 formation against FIX (in ng/ml). (FIG. 14C) Inhibitor formation against FIX (in BU/ml).

FIG. 15. Elevated anti-FIX IgE in hemophilia B dogs S13 and S15 in response to IV delivery of FIX. Arrows indicated start and end of weekly IV injections of recombinant FIX.

FIGS. 16A-16D. Suppression of inhibitor formation in hemophilia B dogs by oral delivery of lyophilized lettuce material, containing CTB-FIX. Oral delivery was twice per week for weeks 0-13. Control dog P05 did not receive lettuce. All dogs were injected IV with recombinant human FIX once per week during weeks 4-11, as indicated by the arrows. (FIG. 16A) IgG2 formation against FIX (in ng/ml). (FIG. 16B) Inhibitor formation against FIX (in BU/ml). (FIG. 16C) IgG1 formation against FIX (in ng/ml). (FIG. 16D) IgE formation against FIX (in ng/ml).

FIGS. 17A-17D. Correction of whole blood clotting time and thromboelastogram values in hemophilia B dogs by oral delivery of lyophilized lettuce material containing CTB-FIX. Dogs were fed with CTB-FIX lettuce twice per week for eleven weeks. Dog P05 was an unfed control. All dogs received an IV injection of recombinant human FIX once per week during weeks 4-11, as indicated by arrows. Hemological parameters were recorded weekly over eleven weeks. (FIG. 17A) Whole blood clotting time. (FIG. 17B) Thromboelastogram values. (FIG. 17C) Platelet counts. (FIG. 17D) White blood cell counts.

Figure 18A:
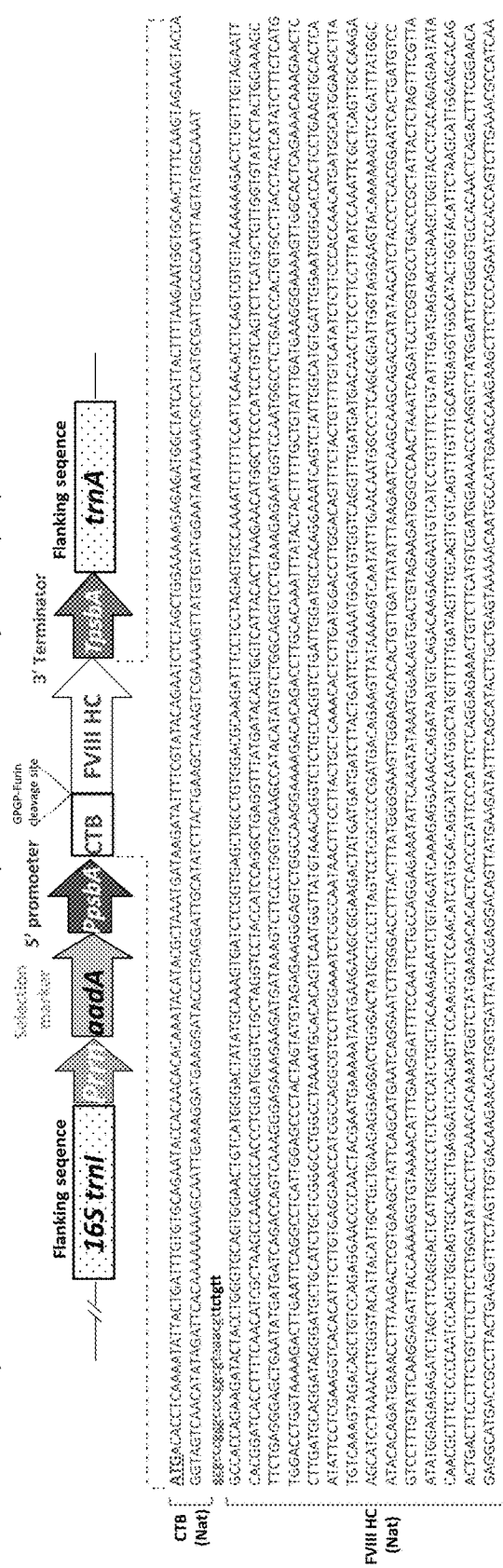
Figure 18C:
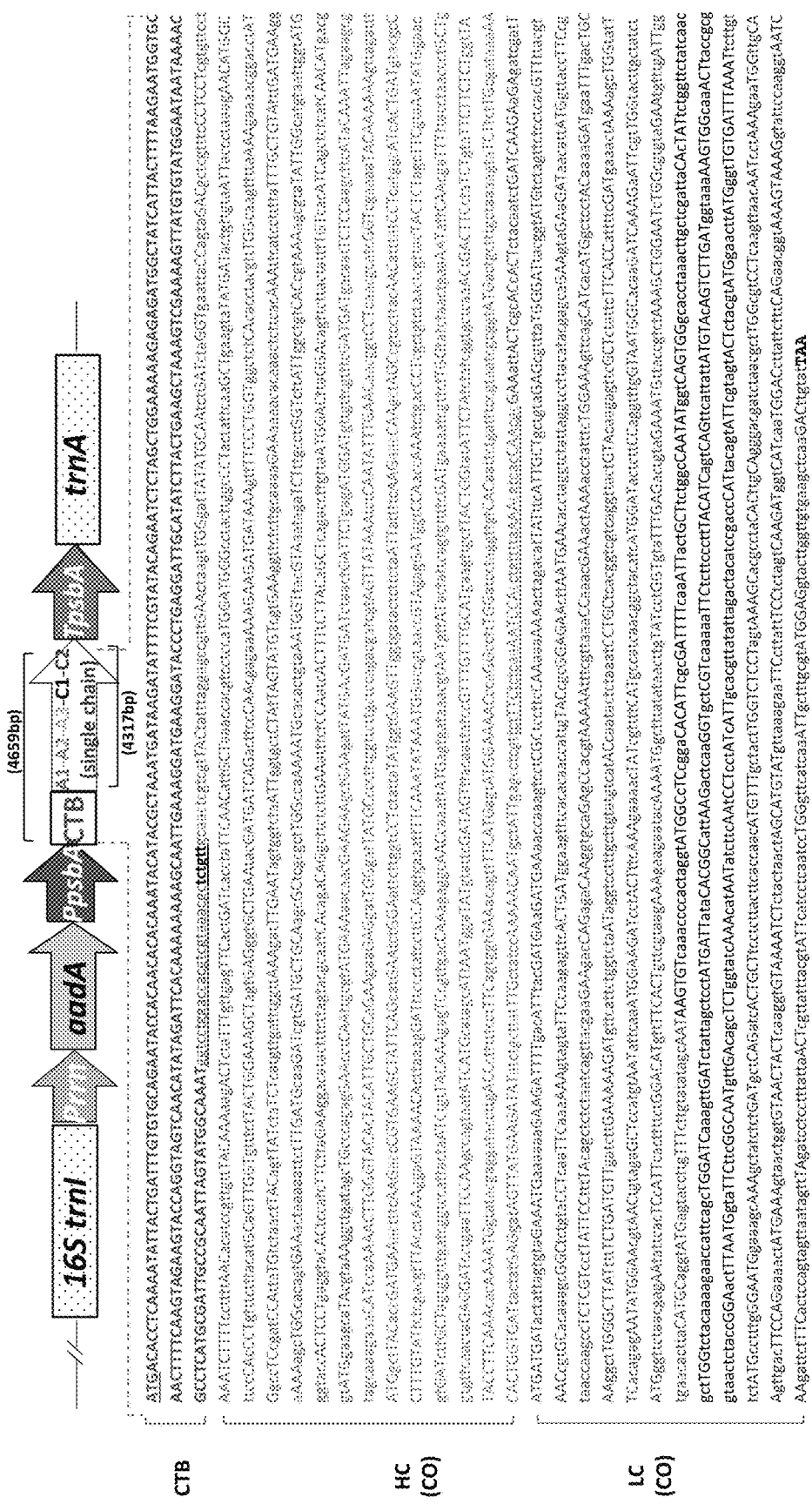

FIGS. 18A-18C. Sequences of native and codon optimized FVIII HC and LC genes, and codon optimized FVIII single chain (SC) construct. (FIG. 18A) Nucleotide sequences of native and codon optimized (CO) FVIII HC genes. (FIG. 18B) Nucleotide sequences of native and codon optimized FVIII LC genes. (FIG. 18C) Nucleotides sequence of codon optimized FVIII SC gene. CTB: Native sequence of cholera non-toxic B subunit; Nat: native sequence; CO: codon optimized sequence obtained from algorithm of optimizer for chloroplast expression.

Figure 19:
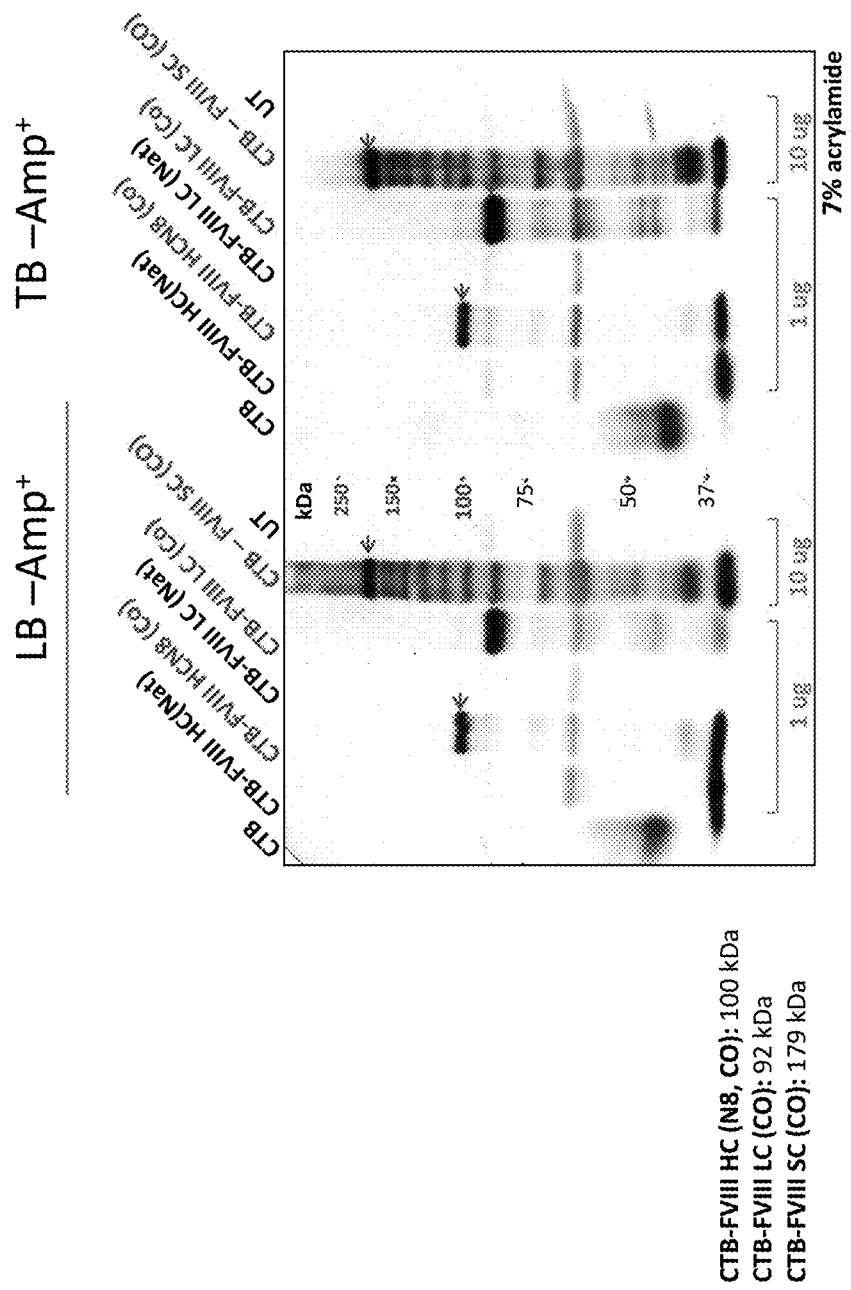

FIG. 19. Western blot assay for expression of native or codon optimized sequences for HC, LC and SC in E. coli. Total proteins were extracted from E. coli transformed with chloroplast expression vectors containing native or codon optimized sequences for FVIII HC, LC and SC. Proteins were loaded as indicated and probed with anti-CTB antibody. The transformed and untransformed (UT) E. coli were incubated in media as indicated at 37° C. overnight. Arrows indicate proteins expected in corresponding sizes.

Figure 20A:
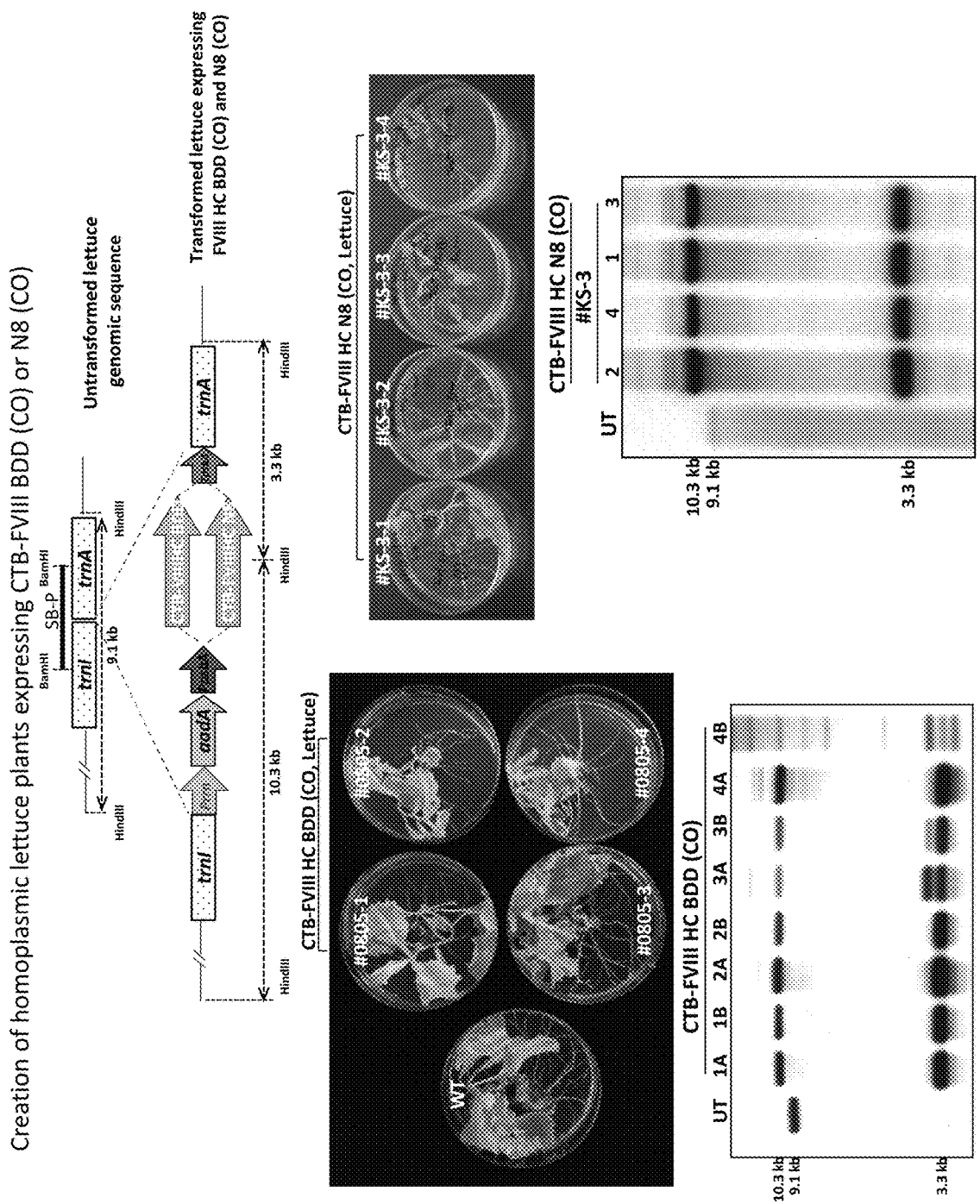
Figure 20B:
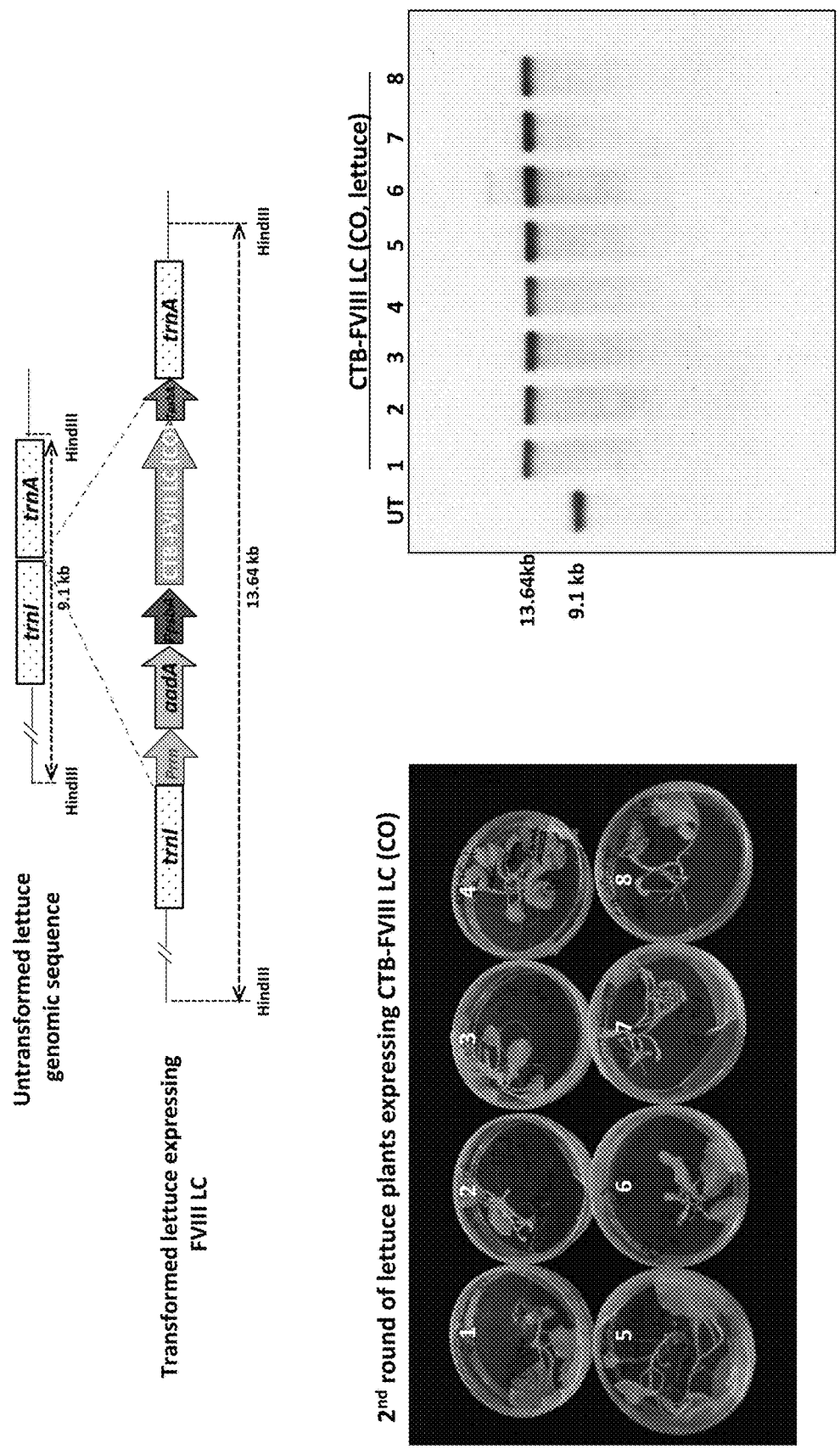
Figure 20C:
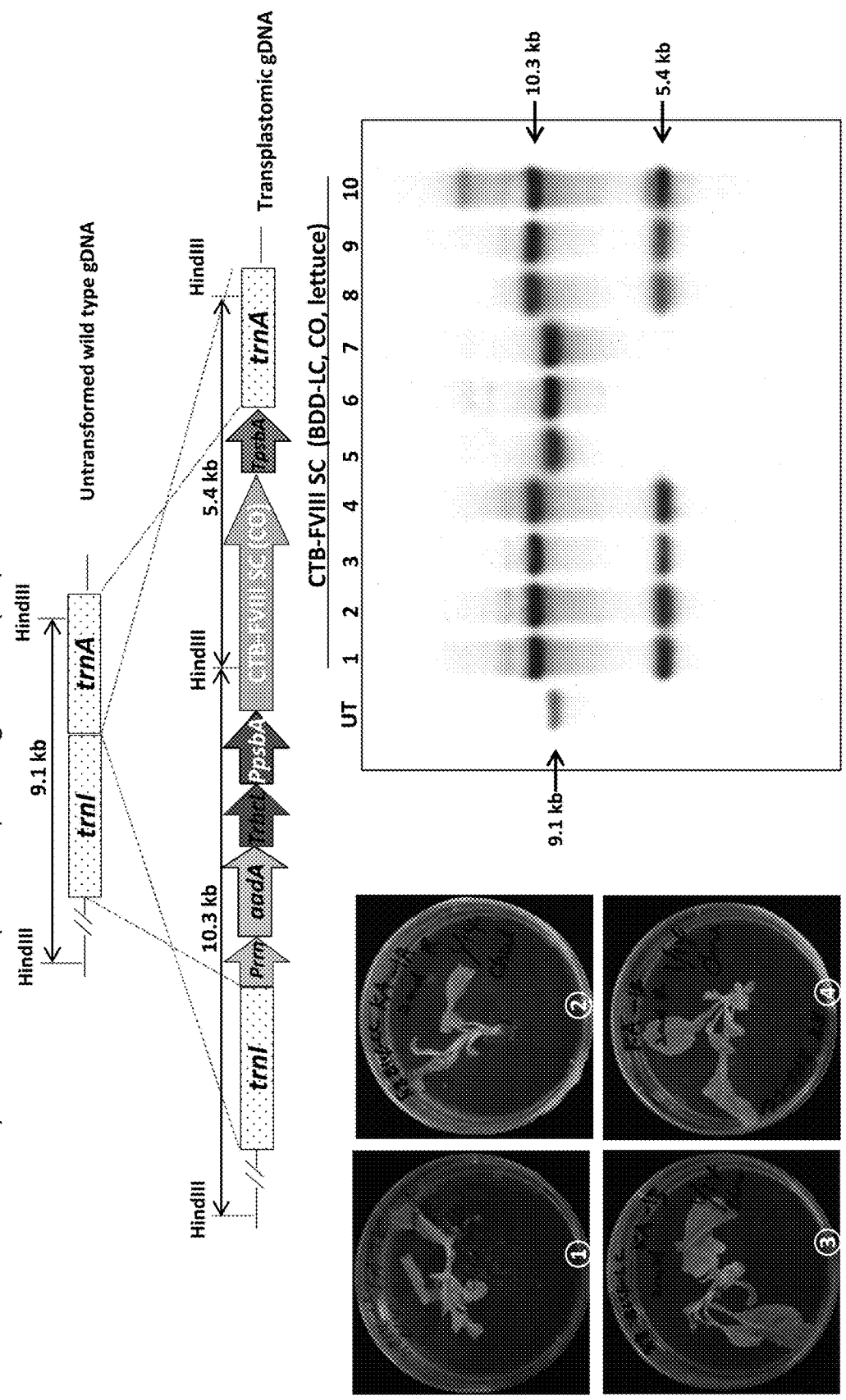

FIGS. 20A-20C. Construction of chloroplast transformation vectors with native and codon optimized genes and confirmation of homoplasmic lines. (FIG. 20A) Lettuce chloroplast vector maps and Southern blot analysis for FVIII HC (BDD and N8). Prrn, rRNA operon promoter; aadA, aminoglycoside 3'-adenylytransferase gene; PpsbA, promoter and 5'-UTR of psbA gene; CTB, coding sequence of cholera non-toxic B subunit; FVIII HC (N), factor 8 heavy chain native sequence; FVIII HC (CO), factor 8 heavy chain codon-optimized sequence; TpsbA, 3'-UTR of the psbA gene; trnI, isoleucyl-tRNA; trnA, alanyl-tRNA. BamHI was used to generate Southern blot probe (SB-P) and HindIII was used for the digestion of genomic DNA. (FIG. 20B) Lettuce chloroplast vector maps and Southern blot analysis for FVIII LC (CO). (FIG. 20C) Lettuce chloroplast vector maps and Southern blot analysis for FVIII SC (CO). Total lettuce genomic DNA (3 µg) was digested with HindIII and separated on a 0.8% agarose gel and blotted onto a Nytran membrane. UT, untransformed wild type plant, FIG. 21. Comparison of expression between native and codon optimized genes of CTB-FVIII HC in lettuce by western blot. Total leaf proteins extracted from lettuce were loaded as indicated and resolved on gradient (4%-20%) SDS-PAGE. The separated protein on the nitrocellulose membrane was probed with anti-CTB antibody. UT, untransformed wild type; Nat, native sequence of FVIII HC; CO, codon-optimized sequence of FVIII HC. For native CTB-FVIII HC, 1 µl is equal to 3.40 µg (Nat), while codon-optimized FVIII HC, 1 ul is 3.86 µg (CO). CTB standard proteins were loaded for quantification as indicated.

Figure 22:
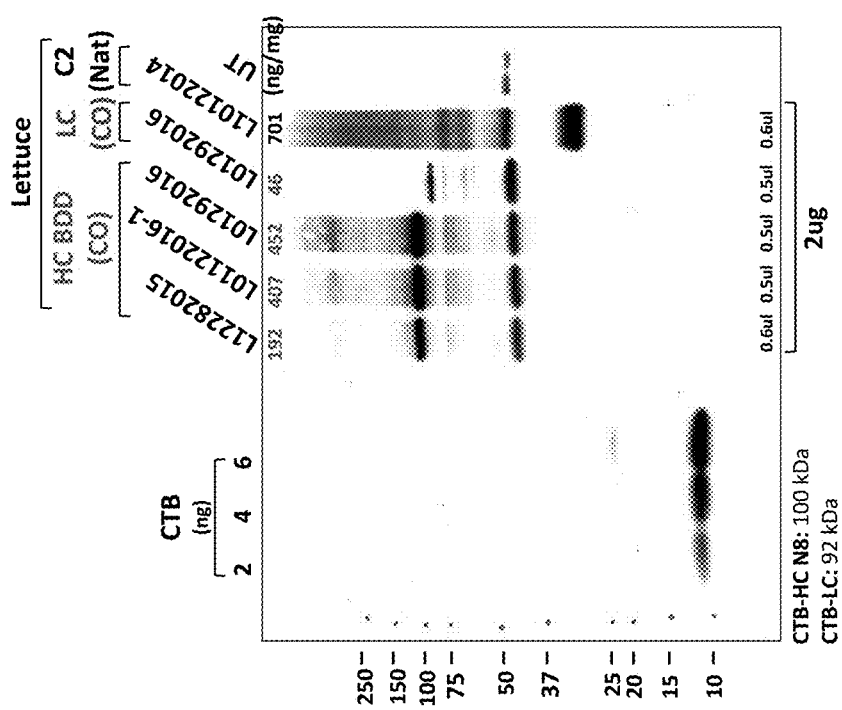

FIG. 22. Comparison of expression between codon optimized FVIII HC, LC and native C2 in lettuce by western blot. Total leaf proteins (10 mg in 500 µl extraction buffer) extracted lyophilized transplastomic plants expressing FVIII HC (CO), LC (CO) and C2 (Nat) were loaded as indicated and resolved on gradient (4%-20%) SDS-PAGE. Anti-CTB antibody was used to probe the FVIII proteins. UT, untransformed wild type (UT); Nat, native sequence; CO, codon-optimized sequence. CTB standards were loaded as indicted for quantification and the calculated results of quantification were indicated below each batch.

Figure 23:
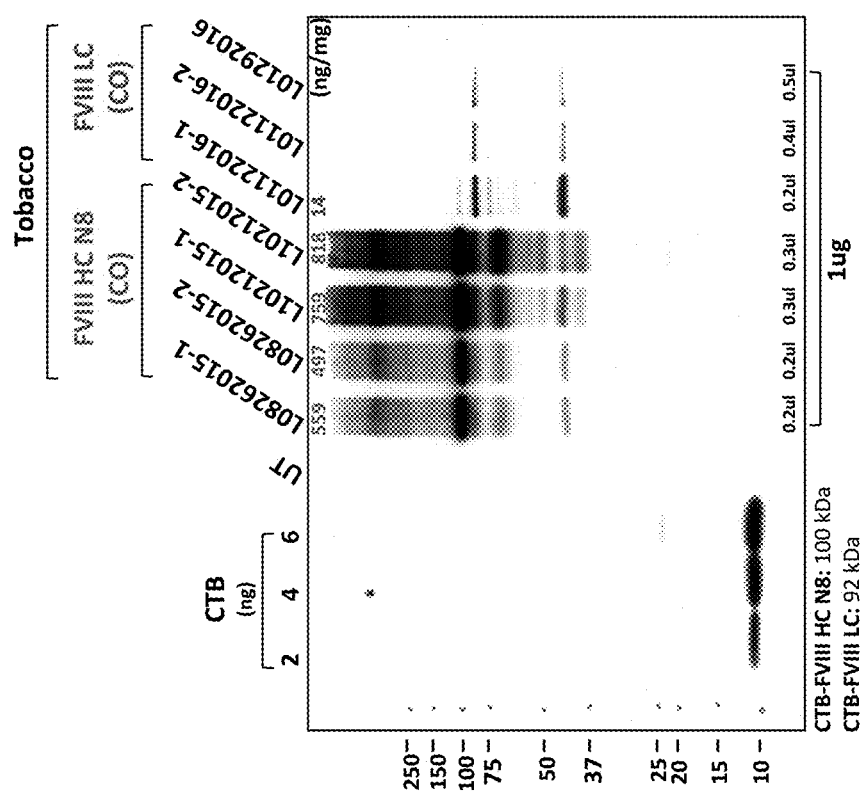

FIG. 23. Comparison of expression between codon optimized FVIII HC and LC in tobacco by western blot. Total leaf proteins (10 mg in 500 µl extraction buffer) extracted lyophilized homoplasmic tobacco plants expressing FVIII HC (CO) and LC (CO) were loaded as indicated and resolved on gradient (4%-20%) SDS-PAGE. Anti-CTB antibody was used to probe the FVIII proteins. UT, untransformed wild type; Nat, native sequence; CO, codon-optimized sequence. CTB standards were loaded as indicted for quantification and the calculated results of quantification were indicated below each batch.

FIG. 24. List of amounts of plant leaf materials. The mature leaves of each homoplasmic plant grown in greenhouse were harvested, lyophilized and powdered. Each batch is labeled based on the day of the lyophilization and the amounts obtained after grinding of lyophilized leaf materials were indicated as in the table.

Figure 25:
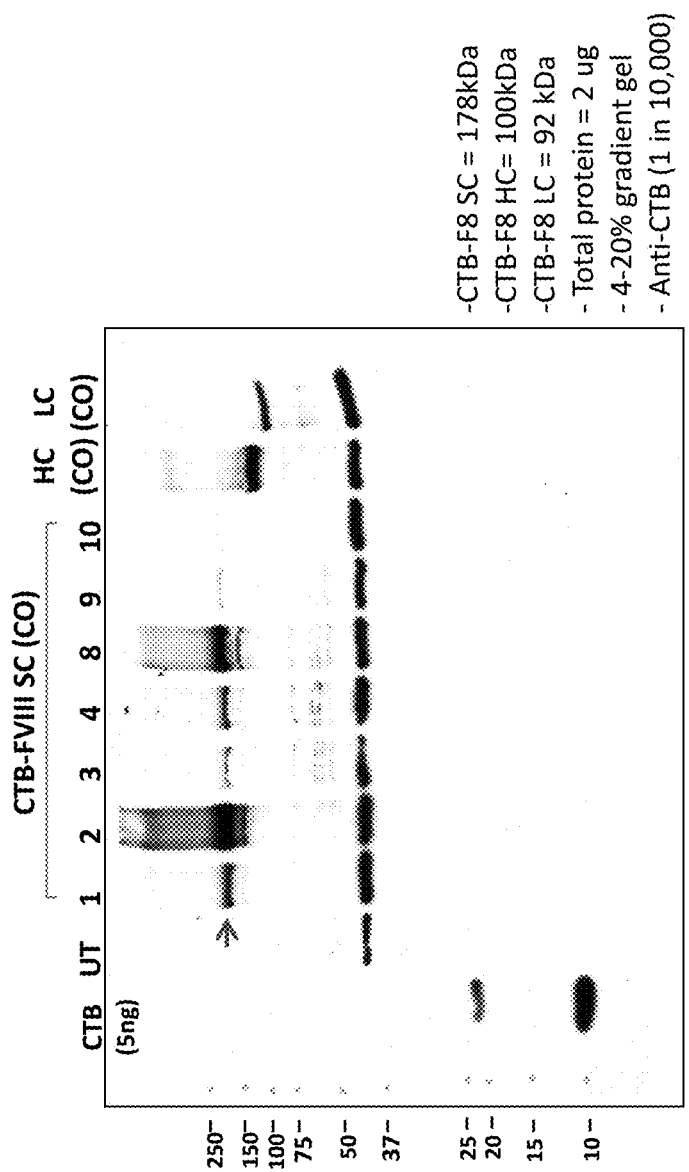

FIG. 25. Evaluation of expression of CTB-FVIII SC (CO) lettuce plants. Total leaf proteins (2 ug) extracted from the homoplasmic lettuce lines (7 lines, fresh leaf materials) expressing CTB-FVIII SC were loaded and immunoprobed with anti-CTB antibody. For comparison of expression level with HC and LC, lyophilized lettuce lines expressing codon-optimized HC and LC were also loaded for western blot assay. UT, untransformed wild type lettuce. Arrow indicated the CTB-FVIII SC (~180 kDa).

FIGS. 26A-26E. Codon optimized FIX. Nucleic acid and amino acid sequence for codon optimized PTD-GPGP.Furin-Propeptide.FIX construct (FIGS. 26A-26B). Codon optimized DNA sequence of Propeptide.FIX.KLW (FIG. 26C). Protein sequence of Propeptide.FIX.KLW (FIG. 26D). Protein Sequence of PTD-GPGP-Furin-Propeptid.FIX.KLW (FIG. 26E).

DETAILED DESCRIPTION OF THE INVENTION

Hemophilia A is an X-linked bleeding disorder due to deficiency of coagulation factor VIII (FVIII). To address serious complications of inhibitory antibody formation in current replacement therapy, we created tobacco and lettuce transplastomic lines expressing FVIII antigens, heavy chain (HC) and C2, fused with the transmucosal carrier, cholera toxin B subunit (CTB). CTB-HC and CTB-C2 fusion proteins expressed up to 80 or 370 µg/g in fresh leaves, assembled into pentameric forms, and bound to GM1 receptors. We also created chloroplast vectors for expressing FIX in lettuce chloroplasts. Protection of FVIII antigen or FIX antigen through bioencapsulation in plant cells and oral delivery to the gut immune system was confirmed by immunostaining. Feeding of HC/C2 mixture of FVIII substantially suppressed T helper cell responses and inhibitor formation against FVIII in hemophilia A mice of two different strain backgrounds. Prolonged oral delivery was required to control inhibitor formation long-term. Substantial reduction of inhibitor titers in pre-immune mice demonstrated that the protocol could also reverse inhibitor formation. Gene expression and flow cytometry analyses showed up-regulation of immune suppressive cytokines (TGF-β/LAP and IL-10). Adoptive transfer experiments confirmed an active suppression mechanism and revealed induction of $CD4^+CD25^+$ and $CD4^+CD25^-$ T cells that potently suppressed anti-FVIII formation. In sum, these data support plant cell-based oral tolerance for suppression of inhibitor formation against FVIII. Additional studies showing prevention of inhibitor formation against FIX expressed in lettuce chloroplasts in a dog model of hemophilia B are also described. The invention also encompasses codon optimized FVIII and FIX sequences which have been optimized for expression in plant chloroplasts.

Unless otherwise defined, all technical and scientific terms used herein have the same meaning as commonly understood by one of ordinary skill in the art of molecular biology.

Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory Press, New York (1982) and Sambrook et al., Molecular Cloning: A Laboratory Manual, Cold Spring Harbor Laboratory Press, New York (1989); Methods in Plant Molecular Biology, Maliga et al, Eds., Cold Spring Harbor Laboratory Press, New York (1995); *Arabidopsis*, Meyerowitz et al, Eds., Cold Spring Harbor Laboratory Press, New York (1994) and the various references cited therein.

Methods, vectors, and compositions for transforming plants and plant cells are taught for example in WO 01/72959; WO 03/057834; and WO 04/005467. WO 01/64023 discusses use of marker free gene constructs.

Proteins expressed in accord with certain embodiments taught herein may be used in vivo by administration to a subject, human or animal, in a variety of ways. The pharmaceutical compositions may be administered orally or parenterally, i.e., subcutaneously, intramuscularly or intravenously. Thus, this invention provides compositions for parenteral administration which comprise a solution of the fusion protein (or derivative thereof) or a cocktail thereof dissolved in an acceptable carrier, preferably an aqueous carrier. A variety of aqueous carriers can be used, e.g., water, buffered water, 0.4% saline, 0.3% glycerine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of fusion protein (or portion thereof) in these formulations can vary widely depending on the specific amino acid sequence of the subject proteins and the desired biological activity, e.g., from less than about 0.5%, usually at or at least about 1% to as much as 15 or 20% by weight and will be selected primarily based on fluid volumes, viscosities, etc., in accordance with the particular mode of administration selected.

Therapeutic compositions produced by embodiments of the present invention can be administrated by the consumption of the foodstuff that has been manufactured with the transgenic plant producing the therapeutic protein. The edible part of the plant is used as a dietary component while the therapeutic protein is administrated in the process.

Thus, in one embodiment, the invention pertains to an administrable tolerance inducing composition that comprises an oral tolerance factor, such as a coagulation factor, having been expressed by a plant and a plant remnant. A plant remnant may include one or more molecules (such as, but not limited to, proteins and fragments thereof, minerals, nucleotides and fragments thereof, plant structural components (such as cellular compartments), etc.) derived from the plant in which the antigen was expressed. Accordingly, a vaccine pertaining to whole plant material (e.g., whole or portions of plant leafs, stems, fruit, etc.) or crude plant extract would certainly contain a high concentration of plant remnants, as well as a composition comprising purified antigen that and one or more detectable plant remnant.

The tolerance inducing compositions of certain embodiments of the present invention may be formulated with a pharmaceutical vehicle or diluent for oral, intravenous, subcutaneous, intranasal, intrabronchial or rectal administration. The pharmaceutical composition can be formulated in a classical manner using solid or liquid vehicles, diluents and additives appropriate to the desired mode of administration. Orally, the composition can be administered in the form of tablets, capsules, granules, powders and the like with at least one vehicle, e.g., starch, calcium carbonate, sucrose, lactose, gelatin, etc. The preparation may also be emulsified. The active immunogenic ingredient is often mixed with excipients which are pharmaceutically acceptable and compatible with the active ingredient. Suitable excipients are, e.g., water, saline, dextrose, glycerol, ethanol or the like and combination thereof. In addition, if desired, the vaccine may contain minor amounts of auxiliary substances such as wetting or emulsifying agents, pH buffering agents, or adjuvants which enhance the effectiveness of the vaccines. The preparation for parental administration includes sterilized water, suspension, emulsion, and suppositories. For the emulsifying agents, propylene glycol, polyethylene glycol, olive oil, ethyloleate, etc. may be used. For suppositories, traditional binders and carriers may include polyalkene glycol, triglyceride, witepsol, macrogol, tween 61, cocoa butter, glycerogelatin, etc. In addition, pharmaceutical grades of mannitol, lactose, starch, magnesium stearate, sodium saccharine, cellulose, magnesium carbonate and the like can be used as excipients.

Oral tolerance factors may be administered by the consumption of the foodstuff that has been manufactured with the transgenic plant and the edible part of the plant expressing the antigen is used directly as a dietary component while the vaccine is administrated in the process.

Examples of readily edible plants that may be transformed to express the constructs described herein include, but are not limited to, apple, berries such as strawberries and raspberries, citrus fruits, tomato, banana, carrot, celery, cauliflower; broccoli, collard greens, cucumber, muskmelon, watermelon, pepper, pear, grape, peach, radish and kale.

The tolerance inducing proteins may be provided with the juice of the transgenic plants for the convenience of administration. For said purpose, the plants to be transformed are preferably selected from the edible plants consisting of tomato, carrot and apple, which are consumed usually in the form of juice.

Those skilled in the art will appreciate that active variants of the genes specifically disclosed herein may be employed to produce plant derived therapeutic compositions. J Exp Med. 1997 May 19; 185(10):1793-801 provides some specific examples of fragments of known antigenic proteins and genes coding therefor.

According to another embodiment, the subject invention pertains to a transformed chloroplast genome that has been transformed with a vector comprising a heterologous gene that expresses a coagulation factor. In a related embodiment, the subject invention pertains to a plant comprising at least one cell transformed to express a coagulation factor.

In one embodiment, coagulation factor polypeptides according to the invention comprise at least 12, 15, 25, 50, 75, 100, 125, 150, 175, 200, 225, 250 or 265 contiguous amino acids of a known coagulation factor sequence. A coagulation factor polypeptide of the invention therefore can be a portion (or fragment) of a coagulation factor, a full-length coagulation factor protein, or a fusion protein comprising all or a portion of coagulation factor protein. Those skilled in the art, equipped with the teachings herein, will be enabled to express and utilize other known coagulation factors. Examples of other coagulation factors that may be used with the present invention include, but are not limited to, those polypeptide sequences associated with the following GenBank or NCBI accession nos. NG_009258.1; NG_008953.1; NG_008107.1; NG_008051.1; NM_001993.3 and NM_00128.3, as provided in the related databases as of the filing date of the present invention.

Coagulation factor polypeptide variants which are biologically active, i.e., confer an ability to increase tolerance against the corresponding factor upon oral administration also are considered coagulation factor polypeptides for purposes of this application. Preferably, naturally or non-naturally occurring coagulation factor polypeptide variants have amino acid sequences which are at least about 55, 60, 65, or 70, preferably about 75, 80, 85, 90, 96, 96, or 98% identical to the amino acid sequence of the known coagulation factor sequence. Percent identity between a putative coagulation factor polypeptide variant and a known amino acid sequence may be determined, for example, by using the Blast2 alignment program (Blosum62, Expect 10, standard genetic codes).

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of an coagulation factor polypeptide can be found using computer programs well known in the art, such as DNASTAR software. Whether an amino acid change results in a biologically active coagulation factor polypeptide can readily be determined by assaying for coagulation factor activity, as described for example, in the specific Examples, below.

A coagulation factor polynucleotide can be single- or double-stranded and comprises a coding sequence or the complement of a coding sequence for an coagulation factor polypeptide. Examples of other coagulation factor polynucleotides that may be used with the present invention include, but are not limited to, those polynucleotide sequences associated with the following GenBank or NCBI accession nos. NG_009258.1; NG_008953.1; NG_008107.1; NG_008051.1; NM_001993.3 and NM_00128.3, as provided in the related databases as of the filing date of the present invention. The codon optimized FVIII and FIX sequences described herein may also be used to increase expression levels of FVIII and FIX.

FVIII is a highly immunogenic molecule that can cause potent antibody responses in hemophilia A patients and in experimental animals at low antigen doses. Under some circumstances, auto-antibodies against FVIII can form in non-hemophilic individuals, resulting in acquired hemophilia A. The majority of inhibitors bind to A2, A3, or C2 domain. These highly immunogenic sequences also contain several CD4+ T cell epitopes. Animal studies suggest that inhibitor formation against FVIII can be prevented by tolerization to parts of the molecule, such as combination of A2 and C2 domains, while a single domain may not be sufficient. It is shown herein that FVIII heavy chain and C2 domain can be expressed as cholera toxin B subunit (CTB) fusion proteins in tobacco. Oral delivery of a mixture of these bioencapsulated antigens suppresses inhibitor formation in hemophilia A mice.

Accordingly, in view of the teachings herein, it is to be appreciated that the full length coagulation factor sequence may be utilized or portions thereof that preserve the epitope peptides. Portions may include polypeptide fragments of at least 15 amino acids with the goal of including and preserving the immunogenic potential of at least one peptide epitope of the sequence. However, ideally, the sequence administered includes as many epitopes as possible, as this would increase the likelihood of successful tolerization. For example, with respect to the FVIII sequence, the full sequence may be expressed, or portions thereof, typically as a fusion protein with CTB. Van Haren et al., Mol Cell Proteomics, 2011) June; 10(6): M110.002246, teaches several sequences pertaining to epitopes (see, e.g., FIG. 2B). Other references teaching the location of different epitopes of the FVIII sequence include Jones et al., Journal of Thrombosis and Haemostasis 2005, 3:991-1000; Reding et al., Journal of Thrombosis and Haemostasis, 2003, 1:1777: 1784; Pratt et al., Thromb Haemost 2004: 92:522-8; and Hu et al., Journal of Thrombosis and Haemostasis 2004, 2:1908-1917. FVIII comprises multiple domains: A1, A2, A3, B, C1 and C2. In certain embodiments, the sequence pertains to the full sequence of at least one of the domains and optionally at least a portion or all of two, three, four, five or six domains. The following is an amino acid sequence of FVIII (*Homo sapiens*), which can be used in a plastid expression scheme (such as by implementing a polynucleotide that codes the full amino acid sequence or portions thereof) or plastid based compositions as taught herein:

MQIELSTCFELCLLRFCFSATRRYYLGAVELSWDYMQSDLGELP

VDAREPPRVPKSFPENTSVVYKKTLFVEFTDHLFNIAKPRPPWMGLLGPT

IQAEVYDTVVITLKNMASHPVSLHAVGVSYWKASEGAEYDDQTSQREKED

DKVFPGGSHTYVWQVLKENGPMASDPLCLTYSYLSHVDLVKDLNSGLIGA

LLVCREGSLAKEKTQTLHKFILLFAVFDEGKSWHSETKNSLMQDRDAASA

RAWPKMHTVNGYVNRSLPGLIGCHRKSVYWHVIGMGTTPEVHSIFLEGHT

FLVRNHRQASLEISPITFLTAQTLLMDLGQFLLFCHISSHQHDGMEAYVK

VDSCPEEPQLRMKNNEEAEDYDDDLTDSEMDVVRFDDDNSPSFIQIRSVA

KKHPKTWVHYIAAEEEDWDYAPLVLAPDDRSYKSQYLNNGPQRIGRKYKK

VRFMAYTDETFKTREAIQHESGILGPLLYGEVGDTLLIIFKNQASRPYNI

YPHGITDVRPLYSRRLPKGVKHLKDFPILPGEIFKYKWTVTVEDGPTKSD

PRCLTRYYSSFVNMERDLASGLIGPLLICYKESVDQRGNQIMSDKRNVIL

FSVFDENRSWYLTENIQRFLPNPAGVQLEDPEFQASNIMHSINGYVFDSL

QLSVCLHEVAYWYILSIGAQTDFLSVFFSGYTFKHKMVYEDTLTLFPFSG

ETVFMSMENPGLWILGCHNSDFRNRGMTALLKVSSCDKNTGDYYEDSYED

ISAYLLSKNNAIEPRSFSQNSRHPSTRQKQFNATTIPENDIEKTDPWFAH

RTPMPKIQNVSSSDLLMLLRQSPTPHGLSLSDLQEAKYETFSDDPSPGAI

DSNNSLSEMTHFRPQLHHSGDMVFTPESGLQLRLNEKLGTTAATELKKLD

FKVSSTSNNLISTIPSDNLAAGTDNTSSLGPPSMPVHYDSQLDTTLFGKK

SSPLTESGGPLSLSEENNDSKLLESGLMNSQESSWGKNVSSTESGRLFKG

KRAHGPALLTKDNALFKVSISLLKTNKTSNNSATNRKTHIDGPSLLIENS

PSVWQNILESDTEFKKVTPLIHDRMLMDKNATALRLNHMSNKTTSSKNME

MVQQKKEGPIPPDAQNPDMSFFKMLFLPESARWIQRTHGKNSLNSGQGPS

PKQLVSLGPEKSVEGQNFLSEKNKVVVGKGEFTKDVGLKEMVFPSSRNLF

LTNLDNLHENNTHNQEKKIQEEIEKKETLIQENVVLPQIHTVTGTKNFMK

NLELLSTRQNVEGSYDGAYAPVLQDFRSLNDSTNRTKKHTAHFSKKGEEE

NLEGLGNQTKQIVEKYACTTRISPNTSQQNFVTQRSKRALKQFRLPLEET

ELEKRIIVDDTSTQWSKNMKHLTPSTLTQIDYNEKEKGAITQSPLSDCLT

RSHSIPQANRSPLPIAKVSSFPSIRPIYLTRVLFQDNSSHLPAASYRKKD

SGVQESSHFLQGAKKNNLSLAILTLEMTGDQREVGSLGTSATNSVTYKKV

ENTVLPKPDLPKTSGKVELLPKVHIYQKDLFPTETSNGSPGHLDLVEGSL

LQGTEGAIKWNEANRPGKVPFLRVATESSAKTPSKLLDPLAWDNHYGTQI

PKEEWKSQEKSPEKTAFKKKDTILSLNACESNHAIAAINEGQNKPEIEVT

WAKQGRTERLCSQNPPVLKRHQREITRTTLQSDQEEIDYDDTISVEMKKE

DFDIYDEDENQSPRSFQKKTRHYFIAAVERLWDYGMSSSPHVLRNRAQSG

SVPQFKKVVFQEFTDGSFTQPLYRGELNEHLGLLGPYIRAEVEDNIMVTF

RNQASRPYSFYSSLISYEEDQRQGAEPRKNFVKPNETKTYFWKVQHHMAP

TKDEFDCKAWAYFSDVDLEKDVHSGLIGPLLVCHTNTLNPAHGRQVTVQE

FALFFTIFDETKSWYFTENMERNCRAPSNIQMEDPTFKENYRFHAINGYI

MDTLPGLVMAQDQRIRWYLLSMGSNENIHSIHFSGHVFTVRKKEEYKMAL

YNLYPGVFETVEMLPSKAGIWRVECLIGEHLHAGMSTLFLVYSNKCQTPL

GMASGHIRDFQITASGQYGQWAPKLARLHYSGSINAWSTKEPFSWIKVDL

LAPMIIHGIKTQGARQKFSSLYISQFIIMYSLDGKKWQTYRGNSTGTLMV

FFGNVDSSGIKHNIFNPPIIARYIRLHPTHYSIRSTLRMELMGCDLNSCS

MPLGMESKAISDAQITASSYFTNMFATWSPSKARLHLQGRSNAWRPQVNN

PKEWLQVDFQKTMKVTGVTTQGVKSLLTSMYVKEFLISSSQDGHQWTLFF

QNGKVKVFQGNQDSFTPVVNSLDPPLLTRYLRIHPQSWVHQIALRMEVLG

CEAQDLY

Degenerate nucleotide sequences encoding coagulation factor polypeptides, as well as homologous nucleotide sequences which are at least about 50, 55, 60, 65, 60, preferably about 75, 90, 96, or 98% identical to the nucleotide sequence encoding a coagulation factor also are coagulation factor polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of coagulation factor polynucleotides which encode biologically active coagulation factor polypeptides also are coagulation factor polynucleotides.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, Science 244: 1081-1085). In the latter technique, mutations are introduced at every positively charged residue in the molecule, and the resultant mutant molecules are tested for activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, Science 255: 306-312; Smith et al., 1992, Journal of Molecular Biology 224: 899-904; Wlodaver et al., 1992, FEBS Letters 309: 59-64).

TABLE 1

| Amino Acid Substitutions<br>Original Residue Exemplary Conservative Substitutions, others are known in the art. |
|---|
| Ala; ser |
| Arg; lys; gln |
| Asn; gln; his |
| Asp; glu |
| Cys; ser |
| Gln; asn; lys |
| Glu; asp |
| Gly; pro |
| His; asn; gln |
| Ile; leu; val |
| Leu; ile; val |
| Lys; arg; gln |
| Met; leu; ile |
| Phe; met; leu; tyr |
| Ser; thr |
| Thr; ser |
| Trp; tyr |
| Tyr; trp; phe |
| Val; ile; leu |

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, are accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, *Proteins: Structure and Molecular Properties*, W. H. Freeman & Co., San Francisco pp 79-86 [1983]), acetylation of the N-terminal amine and, in some instances, amidation of the C-terminal carboxyl.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

Variants and homologs of the coagulation factor polynucleotides described above also are coagulation factor polynucleotides. Typically, homologous coagulation factor polynucleotide sequences can be identified by hybridization of candidate polynucleotides to known coagulation factor polynucleotides under stringent conditions, as is known in the art. For example, using the following wash conditions: 2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes, each homologous sequence can be identified which contain at most about 25-30% basepair mismatches. More preferably, homologous nucleic acid strands contain 15-25% basepair mismatches, even more preferably 5-15% basepair mismatches.

Species homologs of the coagulation factor polynucleotides disclosed herein also can be identified by making suitable probes or primers and screening cDNA expression libraries. It is well known that the Tm of a double-stranded DNA decreases by 1-1.5° C. with every 1% decrease in homology (Bonner et al., *J. Mol. Biol.* 81, 123 (1973). Variants of coagulation factor polynucleotides or polynucleotides of other species can therefore be identified by hybridizing a putative homologous coagulation factor polynucleotide with a polynucleotide having a nucleotide sequence of SEQ ID NO: 1 or the complement thereof to form a test hybrid. The melting temperature of the test hybrid is compared with the melting temperature of a hybrid comprising polynucleotides having perfectly complementary nucleotide sequences, and the number or percent of basepair mismatches within the test hybrid is calculated.

Nucleotide sequences which hybridize to coagulation factor polynucleotides or their complements following stringent hybridization and/or wash conditions also are coagulation factor polynucleotides. Stringent wash conditions are well known and understood in the art and are disclosed, for example, in Sambrook et al., *MOLECULAR CLONING: A LABORATORY MANUAL*, 2nd ed., 1989, at pages 9.50-9.51.

Typically, for stringent hybridization conditions a combination of temperature and salt concentration should be chosen that is approximately 12-20° C. below the calculated Tm of the hybrid under study. The Tm of a hybrid between an coagulation factor polynucleotide having a nucleotide sequence shown in SEQ ID NO: 1 or the complement thereof and a polynucleotide sequence which is at least about 50, preferably about 75, 90, 96, or 98% identical to one of those nucleotide sequences can be calculated, for example, using the equation of Bolton and McCarthy, *Proc. Natl. Acad. Sci. U.S.A.* 48, 1390 (1962): Tm=81.5° C.−16.6 (log 10 [Na+])+0.41(% G+C)−0.63(% formamide)−600/l), where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

In alternative embodiments, the invention pertains to a method of treating a subject having a genetic disease prone and at risk to experiencing an anaphylactic reaction responsive to protein replacement therapy. The method comprises administering to the subject an effective amount of a composition comprising a tolerance factor and a plant remnant, and administering a therapeutically effective amount of a protein corresponding to a defect or deficiency associated with said disease. Typically, a tolerance factor pertains to a coagulation factor (see above) for which sequence information available (See NCBI or GenBank, or Omniprot databases), an acid α-glucosidase (accession nos. NM_001079803.1, NM_001079804.1, NM_0001152.3), α-galactosidase A, (accession no. NM_000169.2) Glucocerebrosidase (accession nos. J03059, J03060), α-L-iduronidase (accession no. NM_000203.3), or sphingomyelinase (accession nos. NM_000543.3, NM_001007593.1). The principles described above with respect to coagulation factor polypeptides and polynucleotides and variants in the preceding eleven paragraphs also apply to the sequences associated with the accession nos. provided in this paragraph. Also, the disease treated typically pertains to Hemophilia A, Hemophilia B, Pompe disease, Fabry disease, Gaucher disease, Mucopolysaccharidosis I, or Niemann-Pick disease. The tolerance factors may be conjugated to a CTB protein (see, e.g., Lai, C Y, Journal of Biological Chemistry, (1977) 252:7249-7256, accession no. DQ523223, and ref. 39) to enhance oral tolerance potential.

The following examples are provided to illustrate certain embodiments of the invention. They are not intended to limit the invention in any way.

EXAMPLE I

Oral Administration of FVIII to Induce Tolerance

While there are currently no prophylactic protocols against inhibitor formation in patients, preclinical experiments in murine models of hemophilia A have provided proof-of-principle that preventive immune tolerance to FVIII can be established.[6-11] However, such protocols utilize genetic manipulation or immune suppressive drugs, raising safety concerns for translation to human treatment. In contrast, oral tolerance could be a more readily acceptable form of prophylactic tolerance induction and may be more readily tested in clinical trials.[12,13] However, effective tolerogenic delivery of coagulation factor antigen to the gut-associated lymphoid tissue (GALT) is a challenge.[14] In accordance with the present invention, we have developed a cost-effective system for production of high levels of protein in chloroplasts of transplastomic tobacco plant cells, which provide bioencapsulation of the antigen through the cellulose containing cell walls.[15,16] Because of the high number of chloroplast genomes per cell and our optimized expression system, transgenic proteins can accumulate in green leaves at much higher levels than this is the case for more traditional transgenic plant technologies.[17,18] Oral delivery of transplastomic plant cells has been effective in prevention of insulitis in non-obese diabetic mice and of inhibitor formation in hemophilia B mice.[19,20]

For FIX inhibitors, ITI is often not sustainable because of anaphylactic reactions and development of nephrotic syndrome. In hemophilia B mice, we demonstrated that repeated oral delivery of bioencapsulated FIX from tobacco plants prevented inhibitor formation and fatal anaphylaxis in subsequent replacement therapy.[20] Encouraged by these results, we sought to develop a protocol for hemophilia A. FVIII is a large protein, comprised of a signal peptide and a 2332 amino acid polypeptide. Structurally, FVIII contains six distinct domains, which are organized in the following order: A1-A2-B-A3-C1-C2.[21] The large, central B domain is highly glycosylated and aids in secretion of the molecule.[22-24] However, recombinant B domain deleted (BDD) FVIII is biologically active, and represents one of the products currently used in the clinic. FVIII is secreted as a heterodimer following at least two intracellular cleavages within the B domain. Consequently, circulating FVIII is comprised of a heavy chain (containing A1-A2-B domains) and a light chain (A3-C1-C2 domains), which are non-covalently linked.[21,23]

FVIII is a highly immunogenic molecule that can cause potent antibody responses in hemophilia A patients and in experimental animals at low antigen doses.[6,25] The majority of inhibitors bind to A2, A3, or C2 domain.[6,26-28] These highly immunogenic sequences also contain several CD4+ T cell epitopes.[6,29-30] Animal studies suggest that inhibitor formation against FVIII can be prevented by tolerization to parts of the molecule, such as combination of A2 and C2 domains, while a single domain may not be sufficient.[14,31] Here, we demonstrate that FVIII heavy chain and C2 domain can be expressed as cholera toxin B subunit (CTB) fusion proteins in tobacco chloroplasts. Oral delivery of a mixture of these bioencapsulated antigens suppressed and also reversed inhibitor formation in a mouse model of hemophilia A.

The following materials and methods are provided to facilitate the practice of the present invention.

Design and Construction of Chloroplast Expression Vectors

Because efficient delivery of bioencapsulated antigen to the GALT is required for tolerance induction and is facilitated by transmucosal carriers, human FVIII antigens were expressed as CTB fusions, a successful strategy for tolerogenic delivery of FIX and pro-insulin.[20,32] Because of the large size of the FVIII molecule and the need for CTB fusions to form pentamers to bind to the GM1 receptor on gut epithelial cells, two separate FVIII chloroplast transformation vectors were constructed to include either the heavy chain (abbreviated as HC, with identical amino acid sequence as in recombinant BDD-FVIII and therefore containing A1 and A2 domains and 5 amino acids of B domain) or the C2 domain. The cDNA fragment of human FVIII-HC was amplified by PCR. PCR products, flanked with a furin cleavage and suitable restriction sites, were cloned into the pCR BluntII Topo vector (Invitrogen), and the sequence was verified. Then, the HC DNA fragment was ligated with pLD-Ctv-5CP chloroplast transformation vector containing the CTB and GPGP hinge sequences to create the pLD-CTB-HC expression vector.[19,33] An analogous pLD-CTB-C2 expression vector was also constructed. Chloroplast vectors pLD-CTB-HC and pLD-CTB-C2 (FIG. 1A) contain homologous flanking sequences 16S/trnI and trnA/23S from tobacco chloroplast genome to facilitate recombination with the native chloroplast genome. Expression of CTB-HC and CTB-C2 is regulated by the highly expressed tobacco chloroplast psbA 5'UTR-promoter and 3'UTR. The CTB-HC and CTB-C2 expression cassettes contain a glycine-proline-glycine-proline (GPGP) hinge between CTB and the HC or C2 element to prevent steric hindrance of the fusion proteins. In addition, a furin cleavage site, Arg-Arg-Lys-Arg, was created at the junction region of the fusion proteins to efficiently release the FVIII domains after internalization by epithelial cells.[34] The expression cassettes include the aadA (aminoglycoside 3' adenylyltransferase) selection marker gene with a GGAG ribosome binding site, driven by a tobacco plastid ribosomal operon promoter (Prrn), to confer spectinomycin resistance. The final chloroplast transformation vectors pLD-CTB-HC and pLD-CTB-C2 (FIG. 1A) were sequenced and used for transformation.[33]

Regeneration of Transplastomic Plants

Tobacco chloroplast transformation vectors pLD-CTB-HC and pLD-CTB-C2 (FIG. 1A) were used to transform tobacco (Nicotiana tabacum) via particle bombardment with gold particles coated with the plasmid DNA.[33] The bombarded leaves were then transferred to selection/regeneration medium. Regeneration of FVIII transplastomic tobacco plants was performed as described earlier.[33,34,35]

Characterization of FVIII Expression in Leaf Tissues of Transplastomic Plants

Immunoblot analysis and quantitation of the CTB-HC and CTB-C2 fusion proteins were performed by previously reported protocols.[18,34] GM1-ganglioside receptor binding assay was performed as reported earlier.[34] The Bis-Tris 3-12% gradient native gel electrophoresis followed by immunoblot analysis was carried out by following the instruction manual of the NativePage Novex Bis-Tris Gel System (Life Technologies).

The cDNA fragment of human FVIII heavy chain (A1-A2 domains plus first 5 amino acids of B domain) is amplified by PCR. PCR products, flanked with a furin cleavage and suitable restriction sites, are cloned into the pCR BluntII Topo vector (Invitrogen), and the sequence is verified. Lettuce expression vector pLsDV-CTB.C2 containing the CTB-C2 DNA fragment was amplified from pLD-CTB.C2 by PCR, and the sequence of the PCR product was confirmed after cloning into pCR BluntII Topo vector. Lettuce expression vector pLs-CTB.C2 was created by subcloning the Ls 5' UTR/CTB-C2/Ls 3' UTR cassette into the pLsDV vector.[34,35] Regeneration of lettuce plants was performed as described earlier.[33,35]

Characterization of the F.VIII Transplastomic Lettuce Plant

To evaluate transgene integration and homoplasmy of the transplastomic lines, PCR and Southern blot analyses were carried out. Immunoblot analysis and quantitation of the CTB-HC and CTB-C2 fusion proteins were performed by previously reported protocols. GM1-ganglioside receptor binding assay was performed as reported earlier. The Bis-Tris 3-12% gradient native gel electrophoresis followed by immunoblot analysis was carried out by following the instruction manual of the NativePage Novex Bis-Tris Gel System (Life Technologies).

Lyophilization and Storage

Lettuce leaves expressing CTB-C2 was lyophilized in Freezone Benchtop Freeze Dry Systems (Labconco) as previously described.[36] Lyophilized leaves were stored at room temperature under vacuum for a few weeks and ground to fine powder in Warring blender. The lyophilized lettuce fine powder was stored dry at room temperature for several months.

Mouse Strains and Experiments

Male hemophilia A mice with targeted deletion of F8 exon 16 ($F8e16^{-/-}$) on a mixed C57BL6/129 or on a pure BALB/c background were housed under special pathogen-free conditions and were ~2 months of age at the onset of experiments.[9,36] Leaf material was ground in liquid nitrogen and stored at −80° C. A mixture of CTB-HC and CTB-C2 material was suspended in sterile PBS (200 μl/dose), homogenized, and delivered via oral gavage using a 20-G bulb-tipped gastric gavage needle. For antigen challenge, mice were administrated 1 IU BBD-human FVIII (Xyntha, Pfizer, New York, N.Y.) into the tail vein once a week. Plasma samples were obtained by tail bleed was as published.[37] ELISA for FVIII antigen and anti-FVIII antibodies, Bethesda assays, and lymphocyte assays were as published.[9,36,37]

Characterization and Quantitation of the CTB-HC and CTB-C2 Fusion Proteins

Tobacco leaves were collected from mature plants at different time points (10 am, 2 pm and 6 pm) on the same day.[1,2] In brief, the leaf samples were frozen and ground in liquid nitrogen. The ground leaf powder was suspended in an extraction buffer (200 mM Tris-HCl, pH 8.0, 100 mM NaCl, 100 mM DTT, 0.1% SDS, 400 mM sucrose, 0.05% Tween 20, 2 mM PMSF and proteinase inhibitor cocktail). The leaf suspension (i.e., homogenate) was either directly used for western blot or underwent an additional centrifugation to separate the supernatant portion. Bradford assay was performed using protein assay dye reagent (Bio-Rad) to determine the protein concentration of the total leaf protein in homogenate fraction and the protein concentration of the total soluble protein in the supernatant portion. To detect the fusion protein expression level in both homogenate fraction and supernatant portion, western blot analysis was performed with anti-CTB antibody as a probe using known concentration of purified CTB protein (Sigma) as the standard. Then, the concentration of CTB-HC or CTB-C2 fusion protein was quantitatively measured by densitometry analysis using Alpha imager 2000. The percentage of fusion protein and amount of transgenic protein (μ/g or mg/g) is calculated according to the formula published earlier.[3]

Lymphocyte Assays

Murine splenocytes were isolated by standard methods and cultured in RPMI 1640 media containing 5 μM β-mercaptoethanol, 100 mM insulin/transferrin/selenium, glutamine and pencillin/streptomycin with or without 10 μg/ml of FVIII for 48 hours at 37° C. and 5% $CO_2$. Cells were then harvested and RNA was extracted using Qiagen RNeasy isolation kit (Valencia, Calif., USA) according to manufacturer's protocol. Quantitative RT-PCR was performed as previously described using SABiosciences kit.[4] Frequencies of IL-10 secreting cells in hemophilia A C57BL6/129 mice in each group were determined by ELISpot assay (R&D System, Minneapolis, Minn., USA) according to manufacturer's protocol. Spots were counted using the CTL-ImmunoSpotH S5 UV analyzer (Cellullar Technology, Shaker Heights, Ohio, USA). Each sample was run in duplicate. $CD4^-$, $CD4^+CD25^-$, and $CD4^+CD25^-$ cells were purified from spleens and MLN using a magnetic isolation kit (Miltenyi Biotech, Bergisch Gladbach, Germany). The cells were then pooled for each experimental group and adoptively transferred to naïve BALB/c mice at $10^6$ cells per mouse via tail vein injection. Recipient mice were challenged 24 hours later via subcutaneous injection of 1 IU FVIII in adjuvant (Sigma Adjuvant System, Sigma, St. Louis, Mo., USA).

Antibody and Antigen Assays

Antibody responses to FVIII were measured via ELISA for anti-FVIII IgG1, IgG2a, and IgG2b, and by Bethesda assay for inhibitor formation as described before.[4-6] Human FVIII HC antigen in circulation was detected via ELISA. Mice were fed with CTB-HC (250 mg) twice per day for 2 days, and bled and sacrificed 5 hours after the last gavage. Harvested liver was washed with cold PBS and homogenized in RIPA buffer (PBS with 1% Nonidet P-40, 0.5% sodium deoxycholate, and 0.1% SDS, pH 7.5) with complete protease inhibitor mixture (Roche Diagnostics, Indianapolis, Ind., USA) for 30 min on ice. After centrifugation for 20 min at 14,000×g at 4° C., the supernatant was collected. For HC-specific ELISA, plate was coated with 2 μg/ml GMA-012 (Green Mountain Antibodies, Burlington, Vt., USA) overnight. BBD-FVIII (Xyntha, Pfizer, New York, N.Y., USA) was used as the standard. Sheep anti-human FVIII (Haematologic Technologies Inc, Essex Junction, Vt., USA) was diluted to 0.3 μg/ml, and HRP-rabbit anti-sheep IgG (Invitrogen, Camarillo, Calif., USA0 was used at 1:2000 dilution. Antibody responses to CTB were measured via ELISA as published.[7]

Flow Cytometry

Spleens, mesenteric lymph nodes, Peyer's patches, and inguinal lymph nodes were harvested, and single cell suspensions were prepared using 70-nm cell strainer in cold PBS buffer, followed by Fc blocker for 5 min at room temperature. Cells were surface stained for CD4-eFluor 450, CD25-PE, LAP-Perp at 4° C. for 30 min in PBS, followed by viability dye eFluor 506 stain at 4° C. for 30 min in PBS.

Fixation and Foxp3 Alexa Fluor 647 stain was performed using the transcriptional factor staining buffer set. Other cells were surface stained with CD4-eFluor 450, CD49b-APC, and LAG3-PE (Tr1 staining) at 4° C. for 30 min in PBS, followed by viability dye eFluor 506. Controls included isotype control, single positive, and unstained cells. All kits and antibodies were purchased form eBiosciences (San Diego, Calif.). Flow cytometry was performed on a LSR II system (BD Bioscience, San Jose, Calif.), and data were analyzed with FCSExpress software (De Novo Software, Los Angeles, Calif.).

Immunohistochemistry

Mice were fed with CTB-C2 (250 mg) twice per day for 2 days and sacrificed 5 hours after the last gavage. Tissue was collected, frozen, cryo-sectioned, and stained as described.[19] The following antibodies were used: rabbit anti-FVIII light chain (1:200, Santa Cruz Biotechnology, Dallas, Tex.); biotin anti-mouse CD11c (1:200, BD Biosciences, San Jose, Calif.; Alexa Fluor-488 donkey anti-rabbit IgG (1:400, Jackson ImmunoResearch Laboratories, West Grove, Pa.), and streptavidin Alexa Fluor-568 (1:400, Invitrogen, Grand Island, N.Y.). Images were captured using Nikon Eclipse 80i fluorescence microscope, Retiga 2000R digital camera (QImaing, Surrey, BC, Canada), and Nikon Elements software.

Results

Characterization of FVIII Transplastomic Lines

Figure 1B:
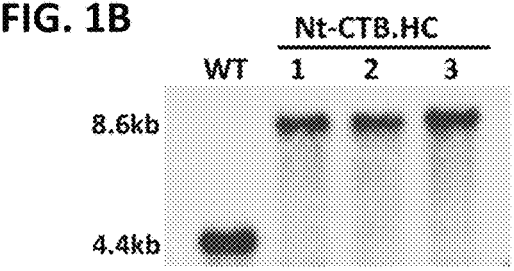
Figure 1C:
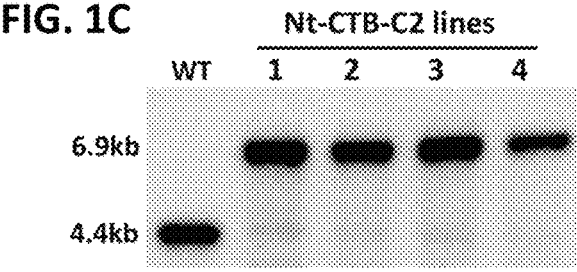

Putative transplastomic tobacco lines obtained after bombardment of chloroplast vectors were first screened by PCR analysis. Site-specific transgene integration into the chloroplast genome was confirmed with two specific primer sets 3P/3M and 5P/2M, which anneal specifically to complementary sequences of transgene cassette and the chloroplast genome.[33] Three independent tobacco lines from pLD-CTB-HC transformation and four independent lines from pLD-CTB-C2 transformation showed positive PCR products of correct sizes (data not shown). The CTB-HC- and CTB-C2-transplastomic tobacco lines were further examined by Southern blot analysis for site-specific stable integration and homoplasmy. Homoplasmy is achieved when all copies of the chloroplast genomes have stably integrated transgenes. The results showed that all 3 tested lines of CTB-HC transplastomic lines had integrated transgenes at specific sites and were homoplasmic, showing only the larger genome fragment (8.6 kb) with the transgene insert when compared with the 4.4 kb fragment in the untransformed control genome (FIG. 1B). The CTB-C2-transplastomic tobacco lines also showed integration of transgenes into the chloroplast genome and homoplasmy (FIG. 1C).

Figure 2A:
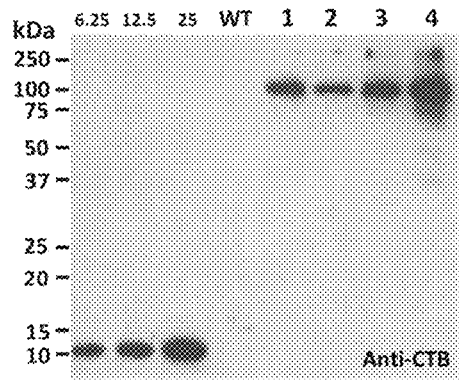
Figure 2B:
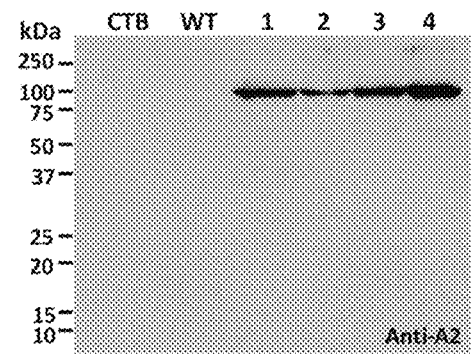
Figure 2C:
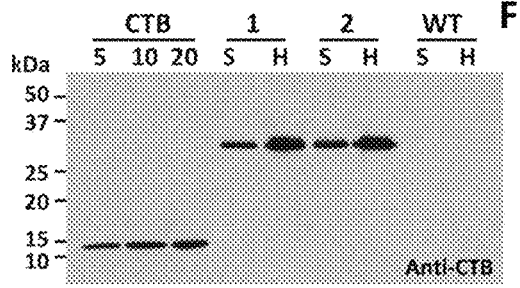
Figure 2D:
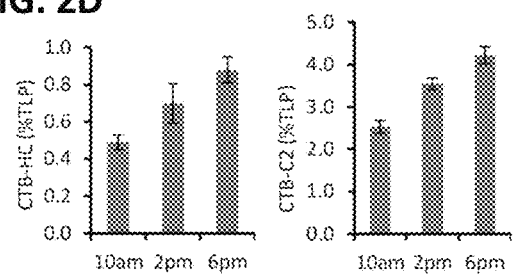

Expression of CTB-HC and CTB-C2 fusion proteins in protein extracts from leaves of transplastomic tobacco plants was evaluated by western blot analysis. Under fully denatured and reducing conditions, blots probed with anti-CTB polyclonal antibody revealed full-length CTB-HC fusion protein with the expected molecular mass of 98 kDa (FIG. 2A) in all transplastomic lines. No cleaved products were observed even after solubilization of pentamers and destabilization of disulfide bonds with reducing agents. A similar banding pattern was observed in a parallel blot probed with an anti-A2 domain specific monoclonal antibody. In addition, there was no cross-reactivity of CTB standard protein or any other plant protein in untransformed leaf extracts (both used as negative controls) with the anti-A2 antibody (FIG. 2B). Quantitation of the fusion protein was performed by densitometry on western blots of leaf extracts using known amounts of purified CTB protein as the standard. The CTB-HC fusion protein was found to accumulate up to 0.8% total leaf protein or 80 μg/g fresh leaf tissue (FIGS. 2A and 2D). The CTB-C2 fusion protein was similarly analyzed with anti-CTB polyclonal antibody in tobacco plants. As shown in FIG. 2C, a 31 kDa polypeptide representing the correct size of CTB-C2 fusion protein was detected in both fractions (supernatant and homogenate) of independent transplastomic lines. The CTB-C2 fusion protein accumulated up to 4.2% in the homogenate (i.e., 4.2% TLP or 370 μg per g of fresh leaf, FIG. 2D).

Pentamer Assembly of CTB-HC and CTB-C2 in Transgenic Chloroplasts

Figure 2E:
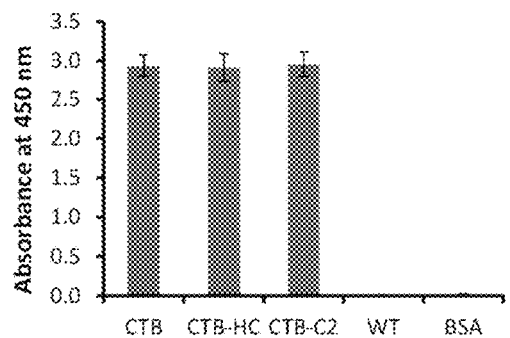
Figure 2F:
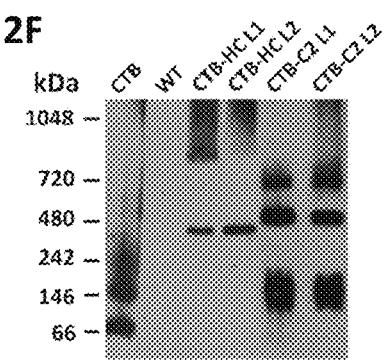

A plasma membrane receptor (GM1-ganglioside) binds CTB in vivo, and a pentameric structure is required for binding to GM1 receptor.[38-40] To evaluate receptor binding ability of CTB-HC and CTB-C2 fusion proteins produced in tobacco chloroplasts, GM1-binding ELISA was performed. As observed in FIG. 2E, CTB-HC and CTB-C2 fusion protein extracts along with purified CTB protein showed strong binding affinity to GM1. Therefore, CTB-HC and CTB-C2 fusion proteins assembled properly to form pentameric structures within transformed chloroplasts. To further evaluate the pentamer assembly directly, we ran blue native gels, and the blots were probed with anti-CTB polyclonal antibody. These results indicate that the pentameric structure (CTB-HC, 490 kDa; CTB-C2, 155 kDa) was formed in both CTB-HC and CTB-C2-transformed tobacco chloroplasts. In addition, other oligomeric forms larger than pentamers were also observed (FIG. 2F). Lack of cleaved products confirmed stability of assembled pentamers or multimers within transformed chloroplasts.

Figure 3A:
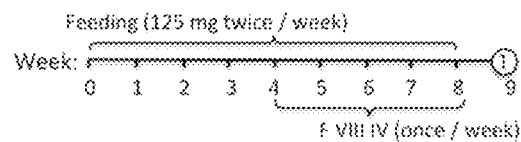
Figure 3B:
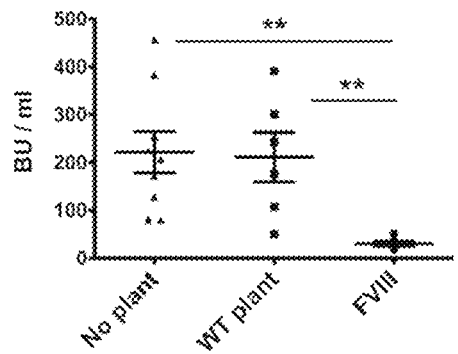
Figure 3C:
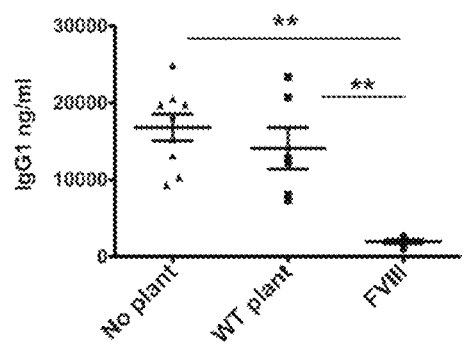
Figure 3D:
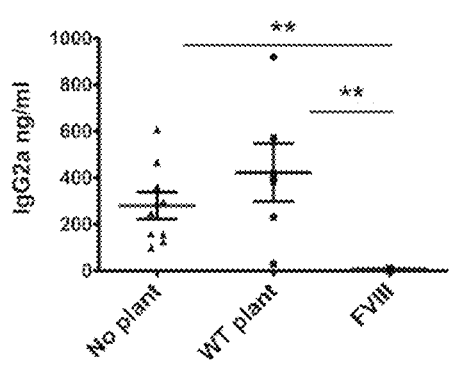
Figure 3E:
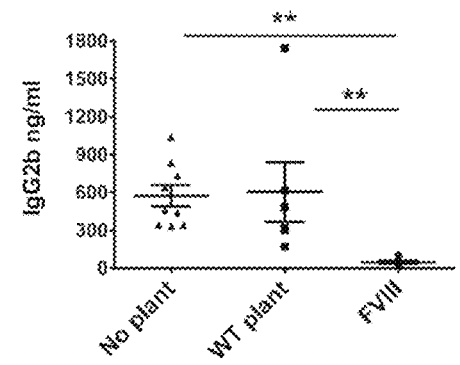

Oral Delivery of Bioencapsulated FVIII Suppresses Inhibitor Formation in Hemophilic Mice Plant leaf materials were ground in liquid nitrogen as published.[19] CTB-HC and CTB-C2 materials were mixed and suspended in PBS buffer so that the final product contained approximately equal amounts of both fusion proteins (~5 μg HC/6 μg C2 per dose/mouse). Male hemophilia A mice (F8e16$^{-/-}$) on C57BL6/129 genetic background received oral gavage of 125 mg mixed material per dose, twice per week for 2 months (FIG. 3A). During the second month, FVIII concentrate (recombinant BDD-FVIII) was given IV once per week at 1 IU/mouse. As expected based on prior findings, control mice that received no gavage (n=9) or were fed with wild type (WT) plant material (n=6) formed very high-titer inhibitors (50-391 BU/ml; FIG. 3B).[9,36] These were predominantly IgG1 with substantially less IgG2a and IgG2b formation (FIG. 3C-3E). In contrast, inhibitor formation was significantly suppressed (on average 7-fold) in those mice that had been fed with FVIII plant material (n=6). These differences in BU correlated with the level of suppression of FVIII-specific IgG1 formation (FIG. 3C). IgG2a and IgG2b anti-FVIII became undetectable in FVIII-fed mice (FIG. 3D-3E).

Figure 3F:
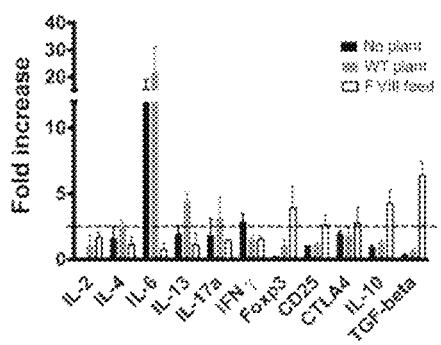

To address the effect of oral antigen delivery on T cell responses to FVIII, we harvested splenocytes from C57BL6/129 F8e16$^{-/-}$ mice that had been fed with WT or FVIII expressing plant material and treated with FVIII. In vitro re-stimulation with FVIII induced expression of several cytokines associated with different T helper cell responses in cultures from WT fed mice (FIG. 3F). IL-6 was the most highly and consistently expressed cytokine, which we have previously shown to be expressed by CD4$^+$ T cells of this strain in response to FVIII.[2] These control mice lacked expression of immune suppressive cytokines or Treg markers. In contrast, splenocytes from FVIII-fed did not show expression of IL-6 or other cytokines associated with Th1 (IL-2, IFN-γ), Th2 (IL-4, IL-13), or Th17 (IL-17) responses.

Figure 3G:
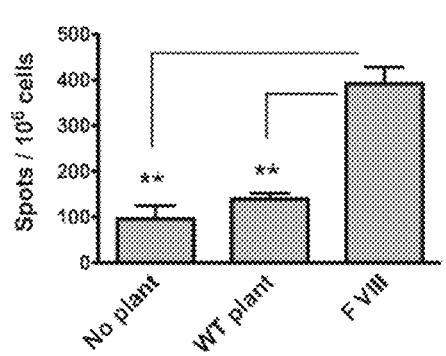

Instead, up-regulation of Treg markers (CD25, FoxP3, CTLA-4) and, more markedly, of suppressive cytokines IL-10 and TGF-β was observed. Hence, the response was shifted from an effector to a suppressive/regulated response. These results were further supported by an increase in IL-10 producing splenocytes in ELISpot assay (FIG. 3G).

Figure 4A:
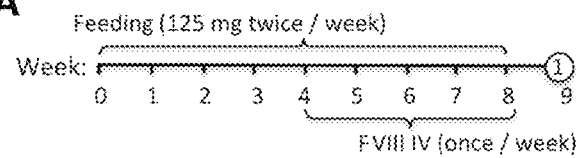
Figure 4B:
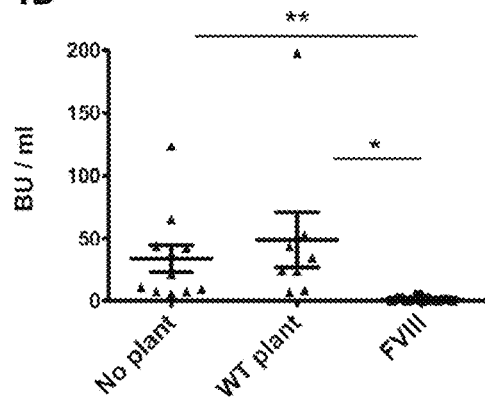
Figure 4C:
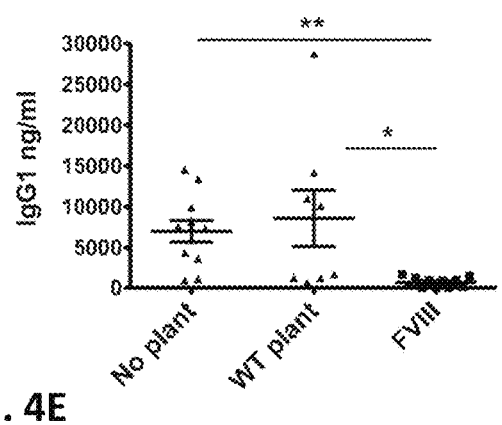
Figure 4D:
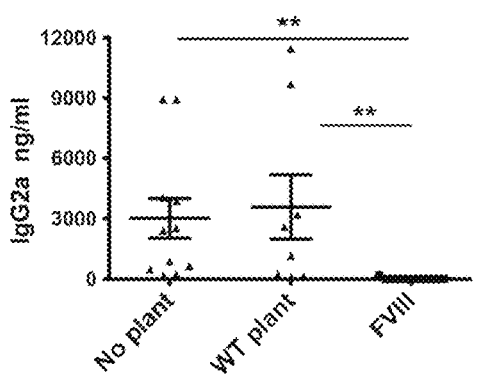
Figure 4E:
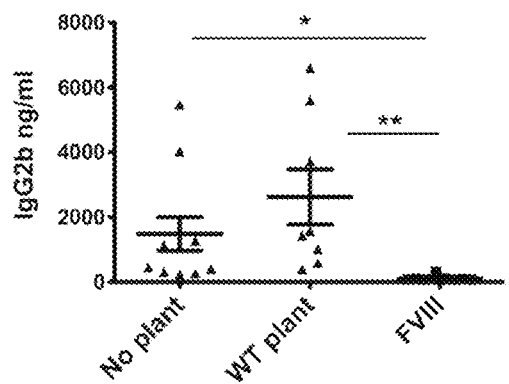
Figure 5B:
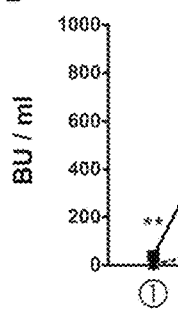
Figure 5C:
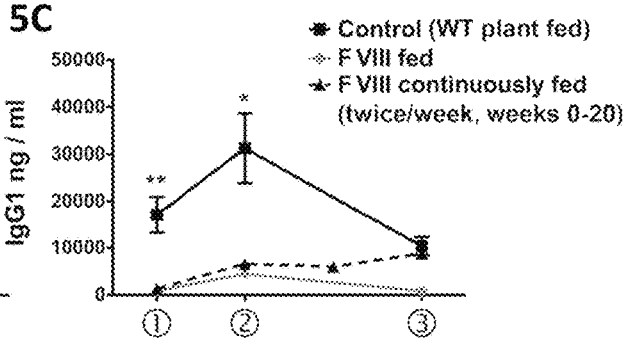

Suppression of Inhibitor Formation is Successful in Different Strain Backgrounds The identical experiment was performed in hemophilia A mice with the same F8 mutation but backcrossed on a BALB/c background. Inhibitor formation in this strain is not as brisk.[36,41] Nonetheless, control mice (n=8-11/group) invariably formed high-titer inhibitors (8-200 BU/ml) after 4 weekly IV injections of FVIII (FIG. 4A-4B). The response was again dominated by IgG1, albeit that IgG2a and IgG2b responses were also observed at substantial titers in some of the animals (FIG. 4C-4E). Among FVIII-fed mice, 7 had undetectable inhibitors and 4 formed low-titer inhibitors (1-4 BU/ml), indicating more complete suppression in this strain by oral antigen administration (FIG. 4B). Total IgG formation was suppressed by approximately 1 log, with absent IgG2a and IgG2b and IgG1 reduced to low-titer (FIG. 4C-4D). Next, we extended weekly IV administration of FVIII (without additional feeding) for another month in 5 animals previously fed with FVIII plant material (3 of which had initially undetectable inhibitors). All 5 mice showed an increase in Bethesda titers to 35-138 BU/ml after 1 month (FIG. 5B). As expected, inhibitor and anti-FVIII IgG titers further increased in control animals treated with FVIII in parallel, reaching levels substantially higher (on average 9-fold) than those in initially FVIII-fed mice (445-998 BU/ml, FIG. 5B). Control mice were subsequently fed with WT plant material for 2 months without further exposure to FVIII (FIG. 5A). These animals maintained their Bethesda titers and showed a modest decline in IgG1 anti-FVIII (FIG. 5B-5C). In animals initially tolerized to FVIII, further oral delivery of FVIII plant material for 2 more months reversed inhibitor titers to an average of 11 BU/ml, ranging from undetectable to 20 BU/ml, which correlated with a reversal of IgG1 formation (FIG. 5A-5C). An additional experimental group (n=7) was orally tolerized, again followed by weekly IV injections of FVIII starting 1 month after initiation of oral tolerance. However, in this case the oral tolerance regimen was continued along with replacement therapy ("FVIII continuously fed" group in FIG. 5A-5B), which resulted in further suppression of the average inhibitor titer at time point #2, (1.7-fold compared to mice with discontinued oral delivery and 15-fold compared to control mice), and suppression was again sustained (FIG. 5B). Reminiscent of our published data on FIX, binding antibodies against FVIII remained detectable by ELISA in this group (FIG. 5C).[20]

Reversal of Inhibitor Formation

Figure 5D:
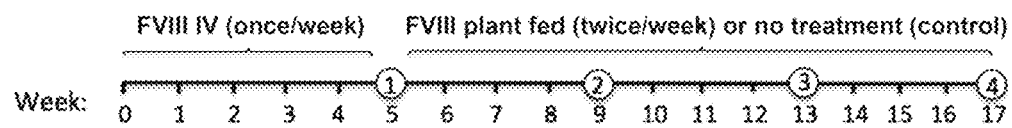
Figure 5E:
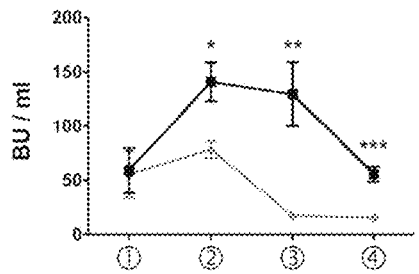
Figure 5F:
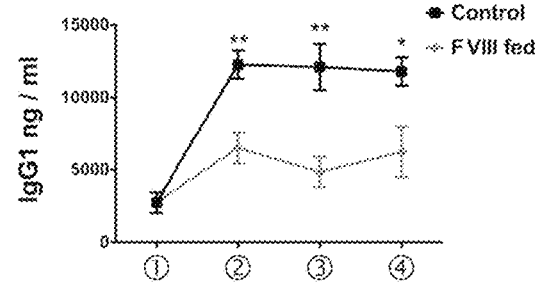

To test whether the oral protocol is effective in pre-immune mice, we treated hemophilia A BALB/c mice with FVIII and divided them into two groups (n=4-5) with similar average Bethesda titers (~60 BU). One group (control) was not further exposed to FVIII antigen, while the other group was subjected to the oral tolerance regimen (FIG. 5D). Inhibitor titers in control animals spontaneously rose further to an average of nearly 150 BU and eventually contracted to the original titer of ~60 BU (FIG. 5E). IgG1 anti-FVIII titers showed a substantial further increase to a level that was subsequently maintained (FIG. 5F). In contrast, oral FVIII delivery slowed and then reversed inhibitor formation, resulting in a 3- to 7-fold decrease compared to controls after 2-3 months of feeding (FIG. 5E). IgG1 formation was also significantly decreased by approximately 2.5-fold (FIG. 5F).

Oral Antigen Delivery Induces a Treg Response Against FVIII

Lymphocyte assays in the C57BL6/129 strain suggested Treg induction. We sought to obtain more direct evidence for induction of active immune suppression using adoptive transfer studies, which was possible in the pure BALB/c background. Lymphocytes were isolated from spleens and mesenteric lymph nodes (MLN) of FVIII-fed hemophilic BALB/c mice at the end of the experiment outlined in FIG. 5A. Upon adoptive transfer to naïve mice of the same strain, CD4$^+$CD25$^+$ T cells, and even more so CD4$^+$CD25$^-$ T cells (but not CD4$^-$ cells) were able to significantly suppress antibody formation to FVIII (FIG. 6A). From previous studies, it has become clear that CD4$^+$CD25$^+$FoxP3$^+$ Treg are critical in tolerance induction to coagulation factors.[8,42] In order to identify potential suppressor cells in the CD4$^+$CD25$^-$ T cell population, we performed flow cytometric analyses of various lymphatic tissues in tolerized versus control mice (FIG. 6B). We found significant induction of CD4$^+$CD25$^-$LAP$^+$ T cells (which express high levels of TGF-β) in spleens, MLN, and Peyer's patches, but no induction of type 1 regulatory T (Tr1) cells (which express high levels of IL-10 and are LAG-3$^+$CD49b$^+$).[12,13,43] Consistent with in vitro RT-PCR array data and our previous findings, overall frequencies of CD4$^+$CD25$^+$FoxP3$^+$ Treg showed only a subtle increase as antigen-specific cells of this subset function at low cell numbers.[42,44]

Local and Systemic Delivery of Bioencapsulated FVIII

Delivery of FVIII antigen to the GALT was demonstrated by immunostaining, which showed presence of fed FVIII antigen in epithelial cells and delivery to dendritic cells (DC) in the lamina propria and Peyer's patches of the small intestine (FIG. 7A-7C). Presence of a furin cleavage site between CTB and FVIII sequences should facilitate systemic delivery of FVIII antigen following uptake in the gut. Indeed, we found HC antigen in plasma samples and liver protein extracts from samples obtained from hemophilia A mice 5 hrs following the last gavage (FIG. 7D). Delivery of CTB-HC/CTB-C2 only infrequently elicited systemic antibody responses to CTB, and there was no correlation between anti-CTB and FVIII inhibitor titers (FIG. 8A-8C and data not shown). The reason for anti-CTB formation in a subset of C57BL6/129 mice is unclear but may relate to processing of the receptor-bound CTB antigen (that is cleaved off FVII sequences) or strength of B or T cell epitopes for this antigen/strain combination.

EXAMPLE II

Generation of Lettuce Transplastomics to Induce Oral Tolerance to FVIII

In order to facilitate clinical translational studies, antigens should be developed in an edible crop. Therefore, we generated lettuce (*Lactuca sativa*) CTB-C2 transplastomic plants. The lettuce chloroplast expression vector pLs-CTB.C2 was created by introducing lettuce flanking sequences 16S/trnI and trnA/23S, and 5' UTR and promoter of psbA gene from lettuce (FIG. 9A). Transplastomic plants were obtained after 3-4 months of selection and regeneration following bombardment of lettuce leaves. Southern blot analysis indicated that homoplasmy was achieved in most transplastomic lines (FIG. 9B). Up to 1.7% TLP (or 102 μg/g fresh leaves) of CTB-C2 fusion protein was expressed in lettuce chloroplasts as observed in western blot analysis (FIG. 9C). The pentamer form of lettuce-made CTB-C2 was also verified by GM1 binding assay and by blue native gel electrophoresis/immunoblot analysis (FIGS. 9D and 9E). No cleaved products were observed even after dissolution of pentamers and destabilization of disulfide bonds by reducing agents (FIG. 9C). The C2 antigen concentration per gram of leaf tissue increased 20 fold after lyophilization. Up to 2004 μg CTB-C2 protein per gram of lyophilized leaf materials was observed (FIG. 9F-9G) when compared to 102 μg/g in fresh leaves, which was detected with a parallel immunoblot assay. The lyophilized and ground lettuce CTB-C2 powder can be prepared as capsules (or in a different formulation more suitable for pediatric patients) and stored at room temperature for long periods to facilitate oral delivery in clinical studies (FIG. 9G).

In order to scale up biomass of CTB-HC leaf materials, more than 200 T1 plants from the CTB-HC transplastomics were transplanted into soils in the greenhouse (FIG. 10A). Western blot analysis to screen the positive plants was first performed (FIG. 10B). Lettuce leaves with high-level expression of CTB-HC fusion protein were harvested. More than 10 kg of fresh CTB-HC lettuce leaves have been collected. Approximately 200 g (dry weight) of lyophilized CTB-HC lettuce leaf powders were obtained from 4 kg of fresh CTB-HC leaves. The concentration of CTB-HC protein in the lyophilized leaf powders was 101 μg per g of dry weight.

Likewise, plants from the CTB-C2 transplastomics were transplanted (FIG. 11A) and screened to verify expression of CTB-C2 (FIG. 11B). Approximately 5 kg of CTB-C2 fresh lettuce leaves were harvested to obtain 150 g of lyophilized CTB-C2 leaf materials. The concentration of CTB-C2 in the lyophilized leaf materials was 3.32 mg per g of dry weight.

Prevention of Inhibitor Formation Against FVIII Using Transplastomic Lettuce

Lyophilized lettuce CTB-HC/CTB-C2 was tested in an oral tolerance protocol to determine its effectiveness in preventing inhibitor formation. Hemophilia A BALB/c mice were assigned to experimental groups (n=7-11) as indicated in Table 2 and fed lyophilized CTB-FVIII lettuce (or tobacco for comparison) for four weeks. Mice were gavaged twice per week for a total of eight weeks (FIG. 12A) and, in the case of the lettuce CTB-FVIII, received varying doses. An additional control group did not receive plant CTB-FVIII. During weeks 5-8, 1IU BDD-FVIII was administered intravenously (IV) once a week to mice in all groups.

One week following the last IV injections, mice were bled and blood samples were analyzed for inhibitors measured in BU/ml (FIG. 12B) and anti-FVIII IgG1 titers (FIG. 12C). At doses of 0.15 μg and 0.5 μg per antigen, the lettuce-fed mice showed 3- to 5-fold lower antibody formation against FVIII compared to control mice. In this study, the transgenic lettuce CTB-FVIII was at least as effective as tobacco and suppressed antibody formation at low doses of fed antigen.

Reversing Existing Inhibitors Using CTB-FVIII from Lettuce

To determine whether an oral protocol using lettuce CTB-FVIII is effective in pre-immune mice, an experiment similar to that depicted in FIG. 5E-5 was conducted. Hemophilia A BALB/c mice were immunized by administering four weekly injections of 1IU recombinant FVIII. During week 5 (i.e., one week following last IV injection) mice were bled. After analyzing blood samples, mice were split into two groups: reversal (n=13) and control (no further treatment, n=9). Both groups had very similar BU measurements and anti-FVIII IgG1 titers after initial IV injections of recombinant FVIII. Each mouse in the reversal group received an oral gavage (twice/week) of a CTB-FVIII mixture (0.5 μg each of C2 and HC in 200 μl of PBS) for the remainder of the study. The control group did not receive CTB-FVIII.

Figure 13B:
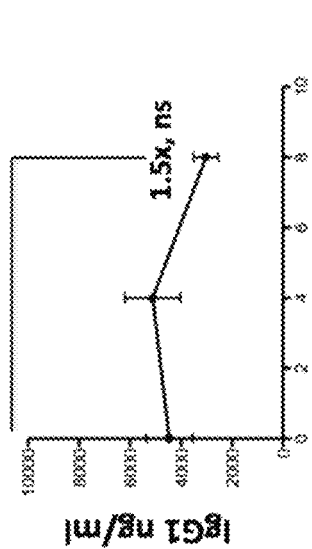
Figure 13D:
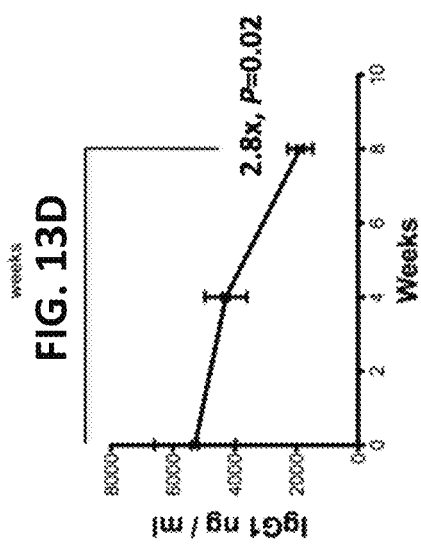
Figure 13A:
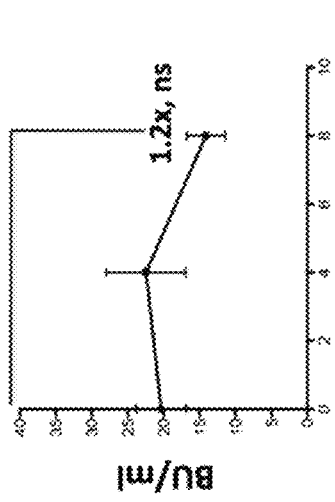
Figure 13C:
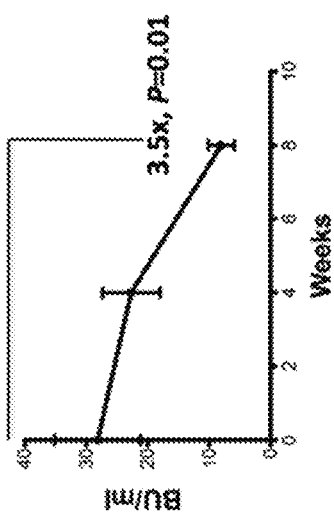

Blood samples obtained during weeks 4 and 8 following the immunization period were analyzed for BU and anti-FVIII IgG1 titers. Only a minor drop in average antibody titers was observed in control mice during the two months following IV injection with recombinant FVIII (FIG. 13A-B). In contrast, anti-FVIII formation in the lettuce fed animals declined approximately 3-fold (FIG. 13C-D).

Induction of Suppressive CD4$^+$ T Cell Responses

Adoptive transfer studies demonstrate that oral FVIII delivery induced multiple subsets of CD4$^+$ T cells that actively suppress antibody formation. Therefore, this mechanism is distinct from immune tolerance induced by hepatocyte-derived antigen, which primarily induces CD4$^+$CD25$^+$FoxP3$^+$ Treg.[44,48,49] Antigen presented in the GALT additionally induced a strongly suppressive CD4$^+$CD25$^-$ T cell response. We do not believe this reflects memory effector T cell activity, as transfer of such FVIII-experienced cells from mice that had not received oral delivery increases rather than suppresses anti-FVIII formation (X Wang, unpublished observations). Rather, flow cytometric analyses of CD4$^+$ T cells suggests induction of CD4$^+$CD25$^-$LAP$^+$ Treg, which are known to be inducible by antigen presentation in the gut and suppress by expression of large amounts of TGF-β, a cytokine that is also required for peripheral induction of CD4$^+$CD25$^+$FoxP3$^+$ Treg. Consistent with tologenic oral antigen delivery, induction of CD4$^+$CD25$^-$LAP$^+$ was observed in Peyer's patches and MLN, which drain the gut, but not non-draining lymph nodes. Increased frequency in the spleen is consistent with suppression of a systemic response, which is required to control inhibitor formation against IV delivered FVIII antigen. We found no evidence

TABLE 2

| Plant material | Dose | Frequency of feeding/duration | IV challenge, 1IU of BDD FVIII |
|---|---|---|---|
| Lyophilized CTB-FVIII tobacco | 0.5 μg of CTB-C2 and CTB-HC each in 100 μl of PBS | Twice per week for two months | Once per week, total of 4 injections |
| Lyophilized CTB-FVIII lettuce | 0.15 μg of CTB-C2 and CTB-HC each in 100 μl of PBS | Twice per week for two months | Once per week, total of 4 injections |
| Lyophilized CTB-FVIII lettuce | 0.5 μg of CTB-C2 and CTB-HC each in 100 μl of PBS | Twice per week for two months | Once per week, total of 4 injections |
| Lyophilized CTB-FVIII lettuce | 1.7 μg of CTB-C2 and CTB-HC each in 100 μl of PBS | Twice per week for two months | Once per week, total of 4 injections |
| Control group | No feeding | | Once per week, total of 4 injections | for induction of Tr1 cells. Nonetheless, there was induction of IL-10, a critical anti-inflammatory cytokine in the GALT. Both FoxP3+ Treg and LAP+ Treg are potential sources of IL-10 expression. Co-delivery of HC and C2 domain was sufficient to suppress inhibitor formation against the entire FVIII molecule in the BALB/c strain. In humans, additional T cell epitopes in other domains likely exist. However, efficient induction of Treg may provide sufficient suppression so that not all epitopes have to be covered by the orally delivered antigens.

In conclusion, oral delivery of modified plant cells induces Tregs that suppress antibody formation to IV delivered FVIII and therefore represents a promising approach to control formation of inhibitors.

Advantages of the Plant-based Platform for Oral Tolerance in Hemophilia

An oral tolerance protocol would be ideal for induction of antigen-specific tolerance while avoiding use of genetic manipulation of patient cells or of immune suppressive drugs, which have undesired side effects, increase the risk of infection, and may impact development of the immune system.[12,14,16,20] Therefore, oral delivery of FVIII antigen may be an acceptable form of prophylactic tolerance induction in pediatric patients. Our current study demonstrates that multiple domains of FVIII can be expressed in plant chloroplasts. Moreover, oral administration of a mixture of bioencapsulated HC and C2 domain antigens substantially suppressed inhibitor formation in subsequent replacement therapy or animals with pre-existing response to FVIII infusion. Thus, new oral tolerance protocols for prevention of inhibitor formation in high-risk patients can be used as an alternative or addition to current ITI.

Oral delivery of plant-made pharmaceutical proteins is emerging as an effective approach. Bioencapsulation of therapeutic proteins within plant cells protects them from harsh environment of the gastrointestinal tract.[15,45,46] In addition, elimination of highly expensive purification, cold storage, transportation and sterile injections significantly reduces their costs.

EXAMPLE III

Expression of FIX in Lettuce and Prevention of Inhibitor Formation Against FIX in Hemophilia B Dogs by Administering Lettuce CTB-FIX In this Example, FIX-transplastomic lettuce plants in an edible system ideal for oral delivery are described. We also describe evaluation of therapeutic efficacy in animal models using a wide dose range and FIX product stability.

To construct the lettuce chloroplast CTB-FIX expression vector, PCR was first performed to amplify the CTB-FIX fusion gene with the primer set NdeI-CTB-Fw (5' TTCAT ATGACACCTCAAAATATTACTGATT 3', the underlined nucleotides represent the start codon of CTB fusion tag) and XbaI-FIX-Rv (5' GATCTAGA TTAAGTGAGCTTTGTTTTTTCCT 3', the underlined nucleotides indicate the stop codon of FIX) from a template plasmid pLD CTB-FFIX[20]. The CTB-FIX PCR products were cloned into pCR-Blunt II-TOPO Vector (Life Technologies Co., Carlsbad, Calif.). After verification of nucleotide sequence, the NdeI-CTB-FIX-XbaI fragment was subcloned into an NdeI-XbaI digested intermediate vector pDVI-1 harboring a lettuce psbA promoter-5' UTR and lettuce psbA 3' UTR. The CTB-FIX expression cassette including the lettuce psbApromoter-5' UTR/CTB-FIX/lettuce psbA 3' UTR was obtained by SalI-NotI digestion and then cloned into SalI-NotI digested pLS-LF vector to create the CTB-FIX lettuce chloroplast expression vector pLS-CTB-FIX which is essentially identical to the vector construct shown in FIGS. 9A and 9B with an FIX encoding nucleic acid.

Transformation and Characterization of Lettuce Transplastomic Lines

Lettuce (*Lactuca sativa*) cv. Simpson Elite leaves were bombarded with the CTB-FIX expression vector and the chloroplast transformants were selected on spectinomycin as previously described. In order to identify the site specific integration of the CTB-FIX transgene into the chloroplast genome and to verify the homoplasmic plants, PCR analysis and Southern blot assays were performed according to previous reports from our laboratory.

Lyophilization of the CTB-FIX Transplastomic Leaves

Frozen lettuce leaves expressing CTB-FIX fusion proteins were freeze-dried in a lyophilizer (Genesis 35XL, SP Scientific, Stone Ridge, N.Y.) at −40° C., −30° C., −20° C., −15° C., −10° C., −5° C. and 25° C. for a total of 72 h under vacuum 400 mTorr. The lyophilized leaves were ground in a coffee grinder (Hamilton Beach, Southern Pines, N.C.) at maximum speed for 3 times (each time, pulse on 6 s and off 90 s). The fine powder or lyophilized leaves were stored in moisture free containers at room temperature with silica gels up to 2 years.

Analysis of CTB-FIX Expression in Transplastomic Lettuce Leaves

Immunoblot analysis and quantitation of the CTB-FIX fusion protein were carried out as described for FVIII in the previous examples. In order to analyze the pentameric structure of CTB-FIX fusion protein expressed in the transformed lettuce chloroplasts, GM1-ganglioside receptor binding ELISA and non-reducing gel-western blot assays were performed as reported earlier.

Hemophilia B Mouse Experiments

Hemophilia B mice with F9 gene deletion on C3H/HeJ background (C3H/HeJ F9$^{-/-}$) were bred as previously published. Male mice approximately 2 months of age were used at the onset of experiments and housed under special pathogen-free conditions at the University of Florida under institutionally approved protocols. Lyophilized plant cells were rehydrated in sterile PBS to a final volume of 200 µl per gavage dose (containing 1.5-15 µg of CTB-FIX antigen) and briefly vortexed for 3-4 seconds. Oral delivery was performed twice per week for 8 weeks by gavage using a 20-G bulb-tipped gastric gavage needle. For FIX replacement therapy, mice were administrated 1 IU hFIX (Benefix, Pfizer, New York, N.Y.) into the tail vein once per week for 8 weeks. Blood was collected by tail bleed into citrate buffer. To prevent fatal anaphylaxis in control animals (that did not receive oral tolerance), anti-histamine and anti-platelet activating factor (anti-PAF) were administered starting at the 4th injection. Antibody formation against FIX in murine plasma was measured by Bethesda assay (using a fibrometer from Stago, Pasippany, N.J.) and by immunoglobulin-specific ELISA as published. Frozen tissue sections from small intestine were prepared for immunohistochemistry and stained for FIX and CD11c antigens as previously documented.

Lettuce CTB-FIX Chloroplast Expression Vector

Edible leafy crop plant (lettuce) capable of producing adequate levels of FIX antigen in chloroplasts have been created for use in the clinic. In order to enhance transformation efficiency, lettuce species specific chloroplast vector was constructed using endogenous full length (~2 kb/flank) flanking sequences. Likewise, we used lettuce psbA promoter, 5'UTR and 3' UTR to enhance transgene expression. These concepts formed the basis for design and construction of pLS-CTB-FIX expression vector (See FIGS. 9A and 9B where vector comprises a FVIII coding region). For expression of FIX antigen, an N-terminal truncated version (47th-461$^{st}$ amino acids) of human FIX cDNA (NCBI database no. FR846240.1) excluding the signal peptide (1st-28th) and propeptide (29th-46th) was used to generate the CTB-FIX expression vector. The vector contained the spectinomycin selection marker gene aadA which could be removed by direct repeats (see discussion section). In addition, a glycine-proline-glycine-proline (GPGP) hinge to prevent steric hindrance was created between CTB and FIX fusion elements. A furin cleavage site (RRKR) was also included in this CTB-FIX expression vector. While this construct lacks the FIX propeptide (which is required for γ-carboxylation) and thus cannot produce functional FIX, the entire amino acid sequence of mature FIX is included, covering all potential CD4$^+$ T cell epitopes for tolerance induction.

Characterization of CTB-FIX Transplastomic Lettuce Lines

CTB-FIX transplastomic lettuce lines were created by biolistic particle bombardment of lettuce leaves from a commercial cultivar (Simpson Elite) with the expression vector pLS-CTB-FIX. PCR results showed the correct sizes of amplicons, 2.77 kb with primer set 16S-Fw/3M, 3.60 kb with 5P/2M and 1.34 kb with CTB-Fw/FIX-Rv1. The site-specific integration of the CTB-FIX gene into the chloroplast genome was further confirmed by Southern blot analysis probed with the lettuce trnI and trnA flanking sequence. All three independent transplastomic lines showed distinct hybridizing fragments in Southern blots with the expected size of 12.6 kb but not the 9.1 kb fragment from untransformed wild type plants, confirming that all three CTB-FIX transplastomic lines were homoplasmic (in which all chloroplast genome have been transformed with insertion of the transgene cassette).

Folding, Stability and CTB-FIX Pentamer Assembly in Lyophilized Lettuce Leaves

Total leaf proteins were extracted with a fully denatured and reducing buffer to analyze CTB-FIX protein. The monomer CTB-FIX fusion protein with the correct molecular mass of 59.2 kDa was detected with anti-CTB or FIX antibody. All transplastomic lettuce lines expressing CTB-FIX were fertile and set seeds. In T1 plants, CTB-FIX expression levels of the young, mature and old leaves were 0.63%, 0.58% and 0.48% of total leaf protein (TLP) respectively. The CTB-FIX concentration of the frozen mature leaves was up to 58.38 μg per g of fresh leaves. CTB-FIX pentamer (296.0 kDa) properly assembled in the transgenic lettuce chloroplasts. Absence of any cleaved products affirms stability of assembled pentamers in plant extracts.

Frozen CTB-FIX lettuce mature leaves were freeze-dried using a lyophilizer as described above for FVIII. A direct comparison of protein concentrations in lyophilized and frozen leaf samples by weight (5-200 μg, 1-40×dilution) was performed and an increase of 18-21 fold CTB-FIX protein concentration was observed after lyophilization. The intact monomer band of CTB-FIX fusion protein was observed without any detectable degradation of CTB-FIX in all tested lyophilized samples after storage for 2, 6, 12 and 24 months, at ambient temperature, confirming that CTB-FIX protein is stable in the freeze-dried lettuce leaves up to 2 years. The stability of the CTB-FIX fusion protein concentrations was similar in all tested samples when normalized for total protein concentration. CTB-FIX concentrations were 0.59% TLP (equivalent to 1478.54 μg/gDW) after 2 month storage, 0.56% TLP (equivalent to 1155.60 μg/gDW) after 6 month storage, 0.54% TLP (equivalent to 846.43 μg/gDW) after 12 month storage and 0.57% TLP (equivalent to 927.02 μg/gDW) after 24 month storage. The results of Paired student's t-test indicated absence of any significant difference in % TLP of CTB-FIX among lyophilized samples stored for different durations at ambient temperature.

A plasma membrane receptor (GM1-ganglioside) binds CTB in vivo, and pentamer formation of CTB is required for binding to GM1 receptor as described above in the previous examples. To further test if the pentameric structure with disulfide bonds was maintained in lyophilized lettuce leaves, GM1-ganglioside receptor binding ELISA was carried out using the lyophilized leaves after long term storage at ambient temperature. CTB-FIX fusion protein extracts from all tested samples showed strong binding affinity to GM1, demonstrating the presence and functional stability of the CTB-FIX pentamers in lyophilized leaves even after long term storage (~2 years).

Scale Up of Biomass and CTB-FIX Dose Evaluation in Capsules

CTB-FIX lettuce plants were transplanted into potted soils in the greenhouse to set seeds. For production of CTB-FIX in a scalable hydroponic system, CTB-FIX seeds were germinated on rockwool or in Petri dishes on filter paper with the nutrient solution. The germination rate of CTB-FIX lettuce seeds on rockwool was 93% when compared to 100% in Petri dishes on filter paper with the nutrient solution. After 32 days of growth, the WT Simpson Elite plants produced more leaf biomass (236.72 g per flat) than CTB-FIX plants (144.89 g per flat). This difference in biomass accumulation was anticipated based on the additional burden of constitutively synthesizing a foreign human protein. The CTB-FIX protein concentration in the lyophilized lettuce leaves collected from the hydroponic system contained 0.38% TLP (equivalent to 1007.55 μg/gDW) which is lower than 0.56% TLP (equivalent to 1459.59 μg/gDW) in lyophilized CTB-FIX lettuce leaves harvested from the Daniell lab greenhouse at the University of Pennsylvania. Two batches of leaves from different harvests at Fraunhofer (32, 51 days old) and UPenn greenhouse (66, 86 days old) samples were analyzed. Based on the current yield of FIX-lettuce production in the hydroponic system, ~870 kg of fresh FIX-lettuce leaves (~43.5 kg dry weight) can be harvested per thousand ft$^2$ of growth room annually. Up to 43.5 g of FIX can be produced from 43.5 kg of dry FIX-lettuce leaves, yielding 24,000-36,000 doses for 20-kg pediatric patients (based on the lowest or highest effective dose for induction of oral tolerance). After lyophilization, the freeze-dried FIX lettuce leaves were ground into fine powder and used to prepare FIX-lettuce capsules.

Oral Delivery of CTB-FIX Lettuce Cells Suppressed Inhibitor Formation Against FIX in Hemophilia B Mice First, we wanted to confirm that oral administration of CTB-FIX bioencapsulated in lettuce cells results in delivery of the FIX antigen to the gut immune system. Lyophilized lettuce (after storage for eight months at ambient temperature) plant cells (containing 10 μg CTB-FIX) were resuspended in sterile PBS and delivered to hemophilia B mice by oral gavage. Five hours later, the small intestine was removed. Immunohistochemical staining of cryosections confirmed delivery of FIX antigen to the gut epithelium and to Peyer's patches, with efficiency similar to our previous observations on FVIII and FIX delivery of tobacco cells. Uptake of FIX antigen to dendritic cells (DC) was demonstrated by co-localization with CD11c$^+$ cells (DCs). Systemic delivery of FIX antigen was observed 2 and 5 h after gavage of lettuce cells at levels similar to those achieved from feeding of identical antigen doses contained in tobacco cells.

Next, hemophilia B mice received oral gavages of the lettuce material twice per week for 2 months. A ten-fold dose escalation (1.5 µg or 15 µg) of CTB-FIX (in 1.9 or 19 mg lyophilized lettuce cells) was investigated. Control mice received WT untransformed lettuce. During the second month of this regimen, all mice (n=11 for control and low dose, n=7 for high dose) were additionally i.v. injected with recombinant FIX (1 IU) once per week. This replacement therapy was continued for 1 month after oral gavages had been stopped. Blood samples were collected 1 week after the last FIX injection. FIX inhibitor titer was robustly suppressed by oral delivery of CTB-FIX expressing lettuce cells for both doses. Average titers were 15-fold lower, and 10 of 11 mice in the low-dose and 5 of 7 mice in the high-dose group had very low (<2 BU) to undetectable inhibitor titers. In contrast, control mice formed high-titer inhibitors (11/11>5BU, with 9/11>10 BU). IgG1 was the dominant subclass of IgG produced against FIX. Average IgG1 titers were suppressed by 3-fold, and—in contrast to control mice—no titers >20,000 ng/ml were measured. Because repeated i.v. delivery of FIX causes not only inhibitor formation but also fatal anaphylaxis in the C3H/HeJ $F9^{-/-}$ strain, control mice were additionally treated with drugs that prevent anaphylactic reactions. Mice that had received oral tolerance using high- or low-dose CTB-FIX in lettuce, despite not being treated with these drugs, did not develop anaphylaxis, consistent with suppression of IgE formation. At the end of these experiments, different organs were analyzed for induction of $LAP^+$ Treg by flow cytometry. A significant increase in the frequency of $LAP^+CD25^-CD4^+$ Treg was found in the spleen, mesenteric lymph nodes, and Peyer's patches (but not in control lymph node) of FIX fed mice.

The demonstration of growing CTB-FIX and WT lettuce (cv. Simpson Elite) plants in a controlled environment hydroponic system illustrates that transformed plants performed well using scalable production methods that are translatable to cGMP (current Good Manufacturing Practices). There was no need to germinate seeds in the presence of antibiotic. The indoor hydroponic system does not require use of pesticides and herbicides. This system can also avoid soil borne diseases. The fast growth rate is another unique advantage of the hydroponic system and one-month-old FIX-lettuce leaves were ready for the first harvest. This opens a path towards human clinical use of CTB-FIX, as well as other similarly expressed proteins. For example, existing plant-based biopharmaceutical production facilities operated under the FDA's GMP guidelines can be modified to accommodate lettuce biomass production.

Prevention of Inhibitor Formation Against FIX in Hemophilia B Dogs by Administering Lettuce CTB-FIX Two one-year old hemophilia B dogs (S14 and S15) received lyophilized lettuce cells containing CTB-FIX as described above, mixed into their food twice per week for thirteen weeks at a dose of 0.3 mg antigen/kg. Starting during the ninth week of oral treatment, recombinant FIX was IV injected at a dose of 10 IU/kg once per week for eight weeks, starting in the ninth week of oral treatment. A control dog, S13, received IV injections but no oral delivery of lettuce CTB-FIX. A second, identical oral tolerance experiment was also performed using dogs S12 (1 year old) and P44 (3 years old), with dog P05 (3 years old) serving as control.

In the absence of inhibitors, IV injection of recombinant FIX would be expected to reduce whole blood clotting time (WBCT), which in an uncorrected hemophilia B dog is greater than 60 minutes. All animals showed correction of WBCT after the first three IV injections. In the first experiment, dog S14 showed correction of WBCT after all eight IV injections (Table 3), indicating that no inhibitor had formed. In contrast, control dog S13 and fed dog S15 did not show correction of the WBCT after the fourth and all subsequent injections. In the second experiment, control dog P05 showed marginal correction of the WBCT after the fourth injection and no correction following subsequent injections. In contrast, both CTB-FIX-fed dogs (P44 and S12) showed correction of WBCT after all 8 injections.

TABLE 3

WBCT (in min) of blood samples obtained 5 min after IV injection of recombinant FIX. Results are shown for each dog.

| IV Injection # | S13 (control) | S14 | S15 | P05 (control) | P44 | S12 |
|---|---|---|---|---|---|---|
| 1 | 14 min | 14 min | 12.5 min | 21.5 min | 20 min | 19 min |
| 2 | 15 min | 12 min | 15.5 min | 24 min | 25.5 min | 20 min |
| 3 | 18.5 min | 15 min | 14.5 min | 20.5 min | 22 min | 20.5 min |
| 4 | >60 min* | 15 min | >60 min | 32.5 min | 20 min | 22 min |
| 5 | >60 min | 15 min | >60 min | >60 min | 23.5 min | 20 min |
| 6 | >60 min | 15 min | >60 min | >60 min | 19.5 min | 18 min |
| 7 | >60 min | 10.5 min | >60 min | >60 min | 21.5 | 21 min |
| 8 | >60 min | 14.5 min | >60 min | >60 min | 25.5 | 23 min |

In the first experiment, control dog S13 formed a very high-titer inhibitor that was first detectable by Bethesda assay four weeks after the first IV injection of recombinant FIX (FIG. 14C). This antibody was primarily comprised of IgG2 (FIG. 14A) but also included IgG1 for some of the time points (FIG. 14B). Dog S14 failed to form an inhibitor (except for a single, late time point of week 12, FIG. 14C), had only low-titer IgG2 (FIG. 14A) and no IgG1 (FIG. 14B). Dog S15 had an intermediate response, which was characterized by similar (albeit lower-titer) inhibitor formation as control dog S14, low-titer IgG2, and no IgG1 formation (FIG. 14A-14C). Although not visible in FIG. 14A because of the scale, dog S15 had a pre-existing antibody against human FIX that was detectable by IgG2 ELISA. Since this dog had not been exposed to human FIX before, the history of this antibody is unknown. Additionally, control dog S13 developed a severe allergic reaction against the infused FIX at the fourth IV injection and was given anti-histamine. Anti-histamine was also administered after all subsequent IV injections. For consistency, this was also done for the fed dogs S14 and S15. In subsequent analysis, S13 and S15, but not S14, were found to have formed IgE against FIX (FIG. 15).

Figure 16A:
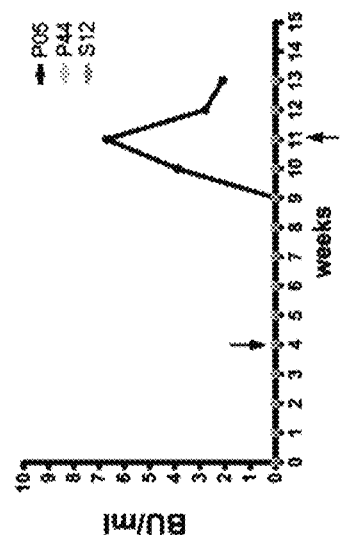
Figure 16B:
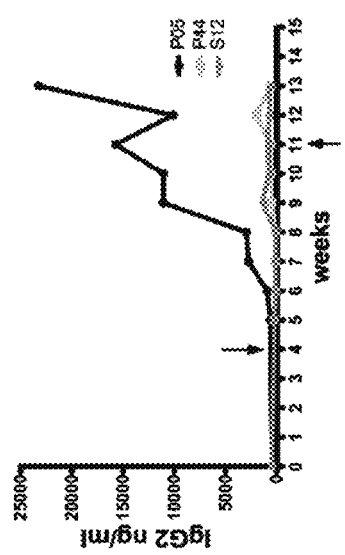
Figure 16C:
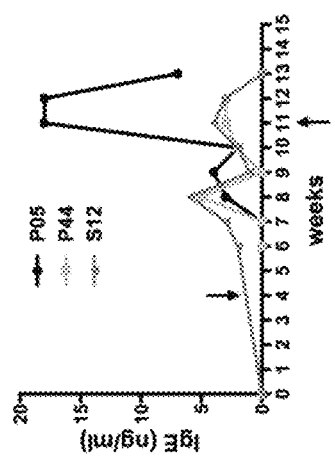
Figure 16D:
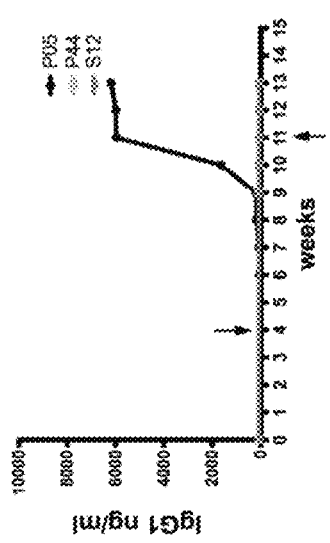

In the second experiment, control dog P05 developed IgG2 by week 8 of the experiment (i.e. four weeks after the first IV injection), followed by a Bethesda titer two weeks later (FIGS. 16A and 16B). P05 also formed IgG1 (FIG. 16C) and showed an allergic reaction to FIX after the seventh IV injection (which was not seen for the two lettuce-fed animals), consistent with data on IgE formation (FIG. 16D). Importantly, lettuce-fed dogs P44 and S12 had no detectable antibody against FIX, which is consistent with their correction of the WBCT, as depicted in Table 3 and FIG. 17A. Throughout the course of the experiments, blood was analyzed for additional hematologic parameters, including clot formation (thromboelastography; FIG. 17B), platelet count (FIG. 17C), and white blood cell count (FIG. 17D).

In summary, the two control dogs treated with recombinant FIX in these studies formed inhibitors that prevented correction of coagulation, starting with the fourth or fifth injection. These animals also had severe allergic reactions to FIX, likely a consequence of IgE formation. Of the four dogs that received CTB-FIX bioencapsulated in lettuce cells, three showed correction of coagulation for all eight IV injections of FIX, lack of inhibitor formation, and lack of or very strong suppression of IgG formation against FIX. One animal, with a pre-existing antibody against FIX of unknown origin, showed only a partial response to the oral tolerance regiment. In summary, these data demonstrate the effectiveness of lettuce-based oral tolerance induction in a large animal model of hemophilia.

EXAMPLE IV

Codon Optimized Expression of FVIII and FIV

We have provided proof-of-principle for suppression of FVIII and FIX inhibitors by oral delivery of transplastomic plant material comprising these molecules in animal models of disease. As has been observed for several other human genes, codon optimization can be employed to increase expression in chloroplasts.[18,32] Previous studies indicated that the C2 domain of FVIII is expressed 3.6-fold higher than the heavy chain because of higher codon compatibility, underscoring the need for codon optimization to achieve optimal levels of expression in chloroplasts. Additionally, the ratio of FVIII domains used in an oral tolerance protocol can alter effectiveness. For example, we observed only a 3-fold reduction in inhibitor titers in hemophilic C57BL6/129 mice when the ratio of FVIII HC:C2 used was 1:3 (instead of 1:1) (data not shown). The tolerogenic antigen mix may be further optimized by preparing different ratios of domains or subunits or by addition of more domains such as A3.

Figure 21:
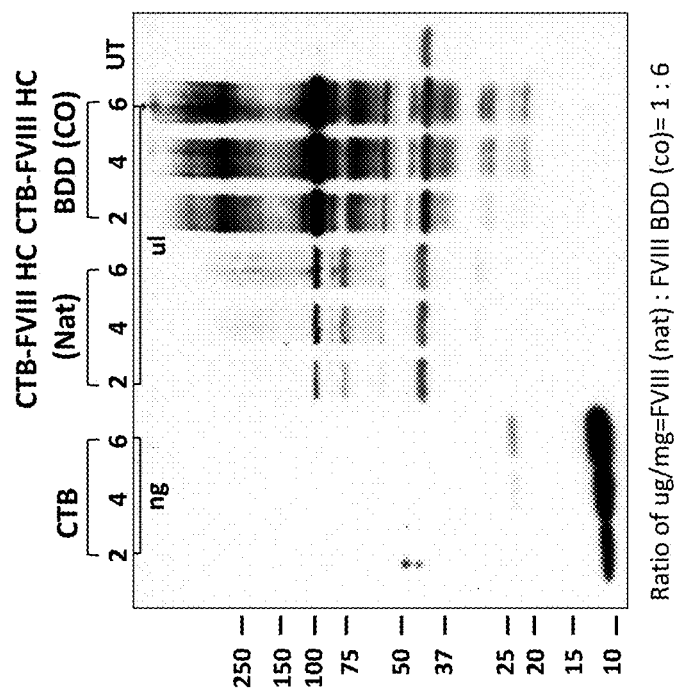

We have developed codon optimized forms of human FVIII HC (FIG. 18A), FVIII LC (FIG. 18B), as well as a codon optimized single-chain (SC) FVIII construct (FIG. 18C). Expression of the codon optimized constructs in *E. coli* was verified by western blot analysis (FIG. 19). Next, codon optimized synthetic genes for FVIII HC (BDD and N8), LC, and SC were inserted into transformation vectors and used to generate homoplasmic lettuce plants (FIG. 20A-20C). Relative expression levels of native and codon optimized genes in lettuce plants were evaluated by western blot (FIG. 21 and FIG. 22). In addition, we generated homoplasmic tobacco plants using the codon optimized LC and HC constructs and measured expression of the proteins in these plants by western blot analysis (FIG. 23). Amounts of plant material obtained from the plants expressing the codon optimized FVIII HC and LC genes are indicated in FIG. 24. Homoplamic lettuce plants were also generated using the codon optimized SC construct (FIG. 21).

A codon optimized version of FIX was also created (FIG. 26A-26B) for increasing expression levels of this transgene in transplastomic plants. This molecule can be expressed with or without the signal peptide for inducing oral tolerance to FIX in hemophilia patients. Notably, FIX cannot be gamma carboxylated when lacking the pro peptide sequence, thus FIX produced from such a construct is a non-functional coagulation factor, but effective to induce tolerance.

REFERENCES

1. Berntorp E, Shapiro A D. Modern haemophilia care. *Lancet.* 2012; 379(9824):1447-1456.
2. Graw J, Brackmann H H, Oldenburg J, Schneppenheim R, Spannagl M, Schwaab R. Haemophilia A: from mutation analysis to new therapies. *Nat Rev Genet.* 2005; 6(6):488-501.
3. Jayandharan G R, Srivastava A. Hemophilia: Disease, Diagnosis and Treatment. *J Genet Syndr Gene Ther* 2011; S 1005.
4. DiMichele D M. Immune tolerance in haemophilia: the long journey to the fork in the road. *Br J Haematol.* 2012; 159(2):123-134.
5. Ehrenforth S, Kreuz W, Scharrer I, et al. Incidence of development of factor VIII and factor IX inhibitors in haemophiliacs. *Lancet.* 1992; 339(8793):594-598.
6. Scott D W, Pratt K P, Miao C H. Progress toward inducing immunologic tolerance to factor VIII. *Blood.* 2013; 121 (22):4449-4456.
7. Adair P, Su Y, Scott D W. Tolerance induction in hemophilia A animal models: battling inhibitors with antigen-specific immunotherapies. *Discov Med.* 2013; 15(84): 275-282.
8. Miao C H. Immunomodulation for inhibitors in hemophilia A: the important role of Treg cells. *Expert Rev Hematol.* 2010; 3(4):469-483.
9. Moghimi B, Sack B K, Nayak S, Markusic D M, Mah C S, Herzog R W. Induction of tolerance to factor VIII by transient co-administration with rapamycin. *J Thromb Haemost.* 2011; 9(8):1524-1533.
10. Oliveira V G, Agua-Doce A, Curotto de Lafaille M A, Lafaille J J, Graca L. Adjuvant facilitates tolerance induction to factor VIII in hemophilic mice through a Foxp3-independent mechanism that relies on IL-10. *Blood.* 2013; 121(19):3936-3945, S3931.
11. Sabatino D E, Nichols T C, Merricks E, Bellinger D A, Herzog R W, Monahan P E. Animal models of hemophilia. *Prog Mol Biol Transl Sci.* 2012; 105151-209.
12. Wang X, Sherman A, Liao G, et al. Mechanism of oral tolerance induction to therapeutic proteins. *Adv Drug Deliv Rev.* 2013; 65(6):759-773.
13. Weiner H L, da Cunha A P, Quintana F, Wu H. Oral tolerance. *Immunol Rev.* 2011; 241(1):241-259.
14. Rawle F E, Pratt K P, Labelle A, Weiner H L, Hough C, Lillicrap D. Induction of partial immune tolerance to factor VIII through prior mucosal exposure to the factor VIII C2 domain. *J Thromb Haemost.* 2006; 4(10):2172-2179.
15. Daniell H, Singh N D, Mason H, Streatfield S J. Plant-made vaccine antigens and biopharmaceuticals. *Trends Plant Sci.* 2009; 14(12):669-679.
16. Kwon K C, Verma D, Singh N D, Herzog R, Daniell H. Oral delivery of human biopharmaceuticals, autoantigens and vaccine antigens bioencapsulated in plant cells. *Adv Drug Deliv Rev.* 2013; 65(6):782-799.
17. Clarke J L, Daniell H. Plastid biotechnology for crop production: present status and future perspectives. *Plant Mol Biol.* 2011; 76(3-5):211-220.
18. Ruhlman T, Verma D, Samson N, Daniell H. The role of heterologous chloroplast sequence elements in transgene integration and expression. *Plant Physiol.* 2010; 152(4): 2088-2104.
19. Ruhlman T, Ahangari R, Devine A, Samsam M, Daniell H. Expression of cholera toxin B-proinsulin fusion protein in lettuce and tobacco chloroplasts—oral administration protects against development of insulitis in non-obese diabetic mice. *Plant Biotechnol J.* 2007; 5(4):495-510.
20. Verma D, Moghimi B, LoDuca P A, et al. Oral delivery of bioencapsulated coagulation factor IX prevents inhibitor formation and fatal anaphylaxis in hemophilia B mice. *Proc Natl Acad Sci USA.* 2010; 107(15):7101-7106.
21. Vehar G A, Keyt B, Eaton D, et al. Structure of human factor VIII. *Nature.* 1984; 312(5992):337-342.
22. Dorner A J, Bole D G, Kaufman R J. The relationship of N-linked glycosylation and heavy chain-binding protein association with the secretion of glycoproteins. *J Cell Biol.* 1987; 105(6 Pt 1):2665-2674.
23. Pipe S W. Functional roles of the factor VIII B domain. *Haemophilia.* 2009; 15(6): 1187-1196.
24. Roberts S A, Dong B, Firrman J A, Moore A R, Sang N, Xiao W. Engineering factor VIII for hemophilia gene therapy. *J Genet Syndr Gene Ther.* 2011; S1006.
25. Wroblewska A, Reipert B M, Pratt K P, Voorberg J. Dangerous liaisons: how the immune system deals with factor VIII. *J Thromb Haemost.* 2013; 11(1):47-55.
26. Markovitz R C, Healey J F, Parker E T, Meeks S L, Lollar P. The diversity of the immune response to the A2 domain of human factor VIII. *Blood.* 2013; 121(14):2785-2795.
27. Meeks S L, Healey J F, Parker E T, Barrow R T, Lollar P. Antihuman factor VIII C2 domain antibodies in hemophilia A mice recognize a functionally complex continuous spectrum of epitopes dominated by inhibitors of factor VIII activation. *Blood.* 2007; 110(13):4234-4242.
28. Pratt K P. Inhibitory antibodies in hemophilia A. *Curr Opin Hematol.* 2012; 19(5):399-405.
29. Pratt K P, Thompson A R. B-cell and T-cell epitopes in anti-factor VIII immune responses. *Clin Rev Allergy Immunol.* 2009; 37(2): 80-95.
30. Steinitz K N, van Helden P M, Binder B, et al. CD4+ T-cell epitopes associated with antibody responses after intravenously and subcutaneously applied human FVIII in humanized hemophilic E17 HLA-DRB1*1501 mice. *Blood.* 2012; 119(17):4073-4082.
31. Lei T C, Scott D W. Induction of tolerance to factor VIII inhibitors by gene therapy with immunodominant A2 and C2 domains presented by B cells as Ig fusion proteins. *Blood.* 2005; 105(12):4865-4870.
32. Boyhan D, Daniell H. Low-cost production of proinsulin in tobacco and lettuce chloroplasts for injectable or oral delivery of functional insulin and C-peptide. *Plant Biotechnol J.* 2011; 9(5):585-598.
33. Verma D, Samson N P, Koya V, Daniell H. A protocol for expression of foreign genes in chloroplasts. *Nat Protoc.* 2008; 3(4):739-758.
34. Kwon K C, Nityanandam R, New J S, Daniell H. Oral delivery of bioencapsulated exendin-4 expressed in chloroplasts lowers blood glucose level in mice and stimulates insulin secretion in beta-TC6 cells. *Plant Biotechnol J.* 2013; 11(1):77-86.
35. Lakshmi P S, Verma D, Yang X, Lloyd B, Daniell H. Low cost tuberculosis vaccine antigens in capsules: expression in chloroplasts, bio-encapsulation, stability and functional evaluation in vitro. *PLoS One.* 2013; 8(1):e54708.
36. Sack B K, Merchant S, Markusic D M, et al. Transient B cell depletion or improved transgene expression by codon optimization promote tolerance to factor VIII in gene therapy. *PLoS One.* 2012; 7(5):e37671.
37. Cao O, Loduca P A, Hoffman B E, et al. Impact of the underlying mutation and the route of vector administration on immune responses to factor IX in gene therapy for hemophilia B. *Mol Ther.* 2009; 17(10):1733-1742.
38. Daniell H, Lee S B, Panchal T, Wiebe P O. Expression of the native cholera toxin B subunit gene and assembly as functional oligomers in transgenic tobacco chloroplasts. *J Mol Biol.* 2001; 311(5):1001-1009.
39. de Haan L, Verweij W R, Feil I K, et al. Role of GM1 binding in the mucosal immunogenicity and adjuvant activity of the *Escherichia coli* heat-labile enterotoxin and its B subunit. *Immunology.* 1998; 94(3):424-430.
40. Tsuji T, Watanabe K, Miyama A. Monomer of the B subunit of heat-labile enterotoxin from enterotoxigenic *Escherichia coli* has little ability to bind to GM1 ganglioside compared to its coligenoid. *Microbiol Immunol.* 1995; 39(10):817-819.
41. Qadura M, Waters B, Burnett E, et al. Immunoglobulin isotypes and functional anti-FVIII antibodies in response to FVIII treatment in Balb/c and C57BL/6 haemophilia A mice. *Haemophilia.* 2011; 17(2):288-295.
42. Markusic D M, Hoffman B E, Perrin G Q, et al. Effective gene therapy for haemophilic mice with pathogenic factor IX antibodies. *EMBO Mol Med.* 2013; 5(11): 1698-1709.
43. Gagliani N, Magnani C F, Huber S, et al. Coexpression of CD49b and LAG-3 identifies human and mouse T regulatory type 1 cells. *Nat Med.* 2013; 19(6):739-746.
44. Hoffman B E, Martino A T, Sack B K, et al. Nonredundant roles of IL-10 and TGF-beta in suppression of immune responses to hepatic AAV-factor IX gene transfer. *Mol Ther.* 2011; 19(7):1263-1272.
45. Kohli N, Westerveld D R, Ayache A C, et al. Oral delivery of bioencapsulated proteins across blood-brain and blood-retinal barriers. *Mol Ther.* 2014; 22(3):535-546.
46. Limaye A, Koya V, Samsam M, Daniell H. Receptor-mediated oral delivery of a bioencapsulated green fluorescent protein expressed in transgenic chloroplasts into the mouse circulatory system. *FASEB J.* 2006; 20(7):959-961.
47. Kumar S, Hahn F M, Baidoo E, et al. Remodeling the isoprenoid pathway in tobacco by expressing the cytoplasmic mevalonate pathway in chloroplasts. *Metab Eng.* 2012; 14(1):19-28.
48. Cao O, Dobrzynski E, Wang L, et al. Induction and role of regulatory CD4+CD25+ T cells in tolerance to the transgene product following hepatic in vivo gene transfer. *Blood.* 2007; 110(4):1132-1140.
49. Cao O, Armstrong E, Schlachterman A, et al. Immune deviation by mucosal antigen administration suppresses gene-transfer-induced inhibitor formation to factor IX. *Blood.* 2006; 108(2):480-486.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated recombinantly produced nucleic acid encoding Factor VIII having the sequence of SEQ ID NO: 15 or a sequence having 90% identity therewith.

2. The nucleic acid of claim 1, present in a plastid transformation vector.

3. An isolated recombinantly produced nucleic acid encoding Factor IX having the sequence of SEQ ID NO:21 or a sequence having 90% identity therewith.

4. The nucleic acid of claim 3, present in a plastid transformation vector.

5. An isolated recombinantly produced nucleic acid encoding a fragment of Factor VIII selected from the group consisting of a heavy chain (HC) fragment encoding by SEQ ID NO: 10, and/or a light chain (LC) fragment encoded by SEQ ID NO: 14, each fused to cholera non-toxic B subunit (CTB) of SEQ ID NO: 6.

6. The nucleic acid of claim 5, present in a plastid transformation vector.

7. The vector of claim 2, present in an edible plant, selected from the group consisting of lettuce, carrot, cauliflower, cabbage, low-nicotine tobacco, spinach, kale and cilantro.

8. The vector of claim 4, present in an edible plant, selected from the group consisting of lettuce, carrot, cauliflower, cabbage, low-nicotine tobacco, spinach, kale and cilantro.

9. The vector of claim 6, present in an edible plant, selected from the group consisting of lettuce, carrot, cauliflower, cabbage, low-nicotine tobacco, spinach, kale and cilantro.

10. A method for the treatment of Hemophilia A in a subject in need thereof comprising administration of an effective amount of the plant of claim 7 to a subject in need thereof, said composition being effective to suppress formation of inhibitors of FVIII in said subject and induce expression of TGF-β producing $CD4^+CD25^-LAP+$ regulatory T cells in spleen, MLN, and Peyer's patches.

11. A method for the treatment of Hemophilia A in a subject in need thereof comprising administration of an effective amount of the plant of claim 9 to a subject in need thereof, said composition being effective to suppress formation of inhibitors of FVIII in said subject and induce expression of TGF-β producing $CD4^+CD25^-LAP+$ regulatory T cells in spleen, MLN, and Peyer's patches.

12. A method for the treatment of Hemophilia B in a subject in need thereof comprising administration of an effective amount of the plant of claim 8 to a subject in need thereof, said composition being effective to suppress formation of inhibitors of FIX in said subject and induce expression of TGF-β producing $CD4^+CD25^-LAP+$ regulatory T cells in spleen, MLN, and Peyer's patches.

13. The method of claim 10, wherein said subject has pre-existing antibody inhibitors to said FVIII.

14. The method of claim 11, wherein said subject has pre-existing antibody inhibitors to said FVIII.

15. The method of claim 12, wherein said subject has pre-existing antibody inhibitors to said FIX.

* * * * *